(12) United States Patent
Bertin

(10) Patent No.: US 6,936,690 B2
(45) Date of Patent: Aug. 30, 2005

(54) MOLECULES OF THE CARD-RELATED PROTEIN FAMILY AND USES THEREOF

(75) Inventor: John Bertin, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 237 days.

(21) Appl. No.: 09/767,215

(22) Filed: Jan. 22, 2001

(65) Prior Publication Data

US 2002/0081636 A1 Jun. 27, 2002

Related U.S. Application Data

(60) Provisional application No. 60/181,159, filed on Feb. 9, 2000.

(51) Int. Cl.$^7$ .............................................. C07K 14/00
(52) U.S. Cl. ................. 530/350; 424/184.1; 424/185.1; 424/192.1; 424/193.1; 424/194.1; 435/7.1
(58) Field of Search ........................ 530/350; 424/184.1, 424/185.1, 192.1, 193.1, 194.1; 435/7.1

(56) References Cited

PUBLICATIONS

Shiozaki E N, 2002, Proceed Natl Acad Sci, USA, 99 (7): 4197–202.*
Lee S H et al, 2001, J Biol Chem, 276(37): 34495–500.*
Willis et al, 1999, Cell 96: 35–45.*
Bowie et al (Science, 1990, 257: 1306–1310).*
Burgess et al. Journal of Cell Biology, 1990, 11: 2129–2138.*
Lazar et al. Molecular and Cell Biology, 1988, 8: 1247–1252.*
Tao. et al. The Journal of Immunology, 1989, 143(8): 2595–2601.*
Gillies et al. Human Antibodies and Hybridomas, 1990, 1(1): 47–54.*
Thornberry et al., Science, 281:1312–1316.*
Hofmann "The modular nature of apoptotic signaling proteins," CMLS Cellular and Molecular Life Sciences, Birkhauser Verlag, Basel CH, 55:1113–1128 (1999).
Bertin et al. "CARD11 and CARD14 are novel caspase recruitment domain (CARD)/membrane–associated guanylate kinase (MAGUK) family members that interact with BCL10 and activate NF–kappaβ," Journal of Biological Chemistry 276(15):11877–11882 (2001).
Abraham, "NF–κB Activation," Critical Care Medicine, 28(4 Supp.):N100–N104 (2000).
Barnes et al., "Nuclear Factor–κB—A Pivotal Transcription Factor in Chronic Inflammatory Diseases," The New England Journal of Medicine, 336(14):1066–1071 (Apr. 3, 1997).
Hofmann et al., "The CARD domain: a new apoptotic signalling motif," TIBS, 22:155–156 (1997).

Imai et al., "The CED–4–homologous protein FLASH is involved in Fas–mediated activation of caspase–8 during apoptosis," NATURE, 398:777–785 (Apr. 29, 1999).
Koseki et al., "CIPER, a Novel NF κB–activating Protein Containing a Caspase Recruitment Domain with Homology to Herpesvirus–2 Protein E10," Journal of Biological Chemistry, 274(15):9955–9961 (Apr. 9, 1999).
Navab et al., "Pathogenesis of Atherosclerosis," The American Journal of Cardiology, 76:18C–23C (Sep. 28, 1995).
Srinivasula et al., "CLAP, a Novel Caspase Recruitment Domain–containing Protein in the Tumor Necrosis Factor Receptor Pathway, Regulates NF–κB Activation and Apoptosis," Journal of Biological Chemistry, 274(25):17946–17954 (Jun. 18, 1999).
Thome et al., "Equine Herpesvirus–2 E10 Gene Product, but Not Its Cellular Homologue, Activates NF–κB Transcription Factor and c–Jun N–terminal Kinase," Journal of Biological Chemistry, 274(15):9962–9968 (Apr. 9, 1999).
Wang et al., "NF–κB Antiapoptosis: Induction of TRAF1 and TRAF2 and c–IAP1 and c–IAP2 to Suppress Caspase–8 Activation," SCIENCE 281:1680–1683 (Sep. 11, 1998).
Willis et al., "BCl10 Is Involved in t(1;14(p22;q32) of MALT B Cell Lymphoma and Mutated in Multiple Tumor Types," CELL, 96:35–45 (Jan. 8, 1999).
Yan et al., "mE10, a Novel Caspase Recruitment Domain––containing Proapoptotic Molecule," Journal of Biological Chemistry, 274(15):10287–10292 (Apr. 9, 1999).
Zhang et al., "Inactivating mutations and overexpression of BCL10, a caspase recruitment domain–containing gene, in MALT lymphoma with t(1;14)(p22;q32)," Nature Genetics 22:63:68 (May 1999).
GenBank™ Accession No. AC015559, Jan. 21, 2000.
GenBank™ Accession No. AK002138, Feb. 22, 2000.
GenBank™ Accession No. AL121229, Feb. 25, 2000.
GenBank™ Accession No. U30894, Feb. 2, 1996.
GenBank™ Accession No. U60111, Sep. 27, 2001.
GenBank™ Accession No. AI188883 (Oct. 28, 1998).
GenBank™ Accession No. BE891229 (Oct. 20, 2000).

* cited by examiner

Primary Examiner—Susan Ungar
Assistant Examiner—Minhtam Davis
(74) Attorney, Agent, or Firm—Millennium Pharmaceuticals, Inc.

(57) ABSTRACT

Novel CARD-14 polypeptides, proteins, and nucleic acid molecules are disclosed. In addition to isolated CARD-14 proteins, the invention further provides CARD-14 fusion proteins, antigenic peptides and anti-CARD-14 antibodies. The invention also provides CARD-14 nucleic acid molecules, recombinant expression vectors containing a nucleic acid molecule of the invention, host cells into which the expression vectors have been introduced and non-human transgenic animals in which a CARD-14 gene has been introduced or disrupted. Diagnostic, screening and therapeutic methods utilizing compositions of the invention are also provided.

16 Claims, 17 Drawing Sheets

```
attcggctcg agttcacctg gtgctgcttt gacttcaggc tcttccttct gcccagctcc    60
gtcccaccca gcagcccgca gagaaaggag gcagctggca ccacactggg ctttggagac   120
actgcgggga ctgtggaccc caccctgctg cacggagctc ctgcaaaagc aaacctgaga   180
accttgggtc ctcccagcgc ccagcc atg ggg gaa ctg tgc cgc agg gac tcc    233
               Met Gly Glu Leu Cys Arg Arg Asp Ser
                 1               5 gca ctc acg gca ctg gac gag gag aca ctg tgg gag atg atg gag agc    281
Ala Leu Thr Ala Leu Asp Glu Glu Thr Leu Trp Glu Met Met Glu Ser
 10              15              20              25 cac cgc cac agg atc gta cgc tgc atc tgc ccc agc cgc ctc acc ccc    329
His Arg His Arg Ile Val Arg Cys Ile Cys Pro Ser Arg Leu Thr Pro
                30              35              40 tac ctg cgc cag gcc aag gtg ctg tgc cag ctg gac gag gag gag gtg    377
Tyr Leu Arg Gln Ala Lys Val Leu Cys Gln Leu Asp Glu Glu Glu Val
             45              50              55 ctg cac agc ccc cgg ctc acc aac agc gcc atg cgg gcc ggg cac ttg    425
Leu His Ser Pro Arg Leu Thr Asn Ser Ala Met Arg Ala Gly His Leu
         60              65              70 ctg gat ttg ctg aag act cga ggg aag aac ggg gcc atc gcc ttc ctg    473
Leu Asp Leu Leu Lys Thr Arg Gly Lys Asn Gly Ala Ile Ala Phe Leu
     75              80              85 gag agc ctg aag ttc cac aac cct gac gtc tac acc ctg gtc acc ggg    521
Glu Ser Leu Lys Phe His Asn Pro Asp Val Tyr Thr Leu Val Thr Gly
 90              95             100             105 ctg cag cct gat gtt gac ttc agt aac ttt agc ggt ctc atg gag aca    569
Leu Gln Pro Asp Val Asp Phe Ser Asn Phe Ser Gly Leu Met Glu Thr
                110             115             120 tcc aag ctg acc gag tgc ctg gct ggg gcc atc ggc agc ctg cag gag    617
Ser Lys Leu Thr Glu Cys Leu Ala Gly Ala Ile Gly Ser Leu Gln Glu
            125             130             135 gag ctg aac cag gaa aag ggg cag aag gag gtg ctg ctg cgg cgg tgc    665
Glu Leu Asn Gln Glu Lys Gly Gln Lys Glu Val Leu Leu Arg Arg Cys
        140             145             150 cag cag ctg cag gag cac ctg ggc ctg gcc gag acc cgt gcc gag ggc    713
Gln Gln Leu Gln Glu His Leu Gly Leu Ala Glu Thr Arg Ala Glu Gly
    155             160             165 ctg cac cag ctg gag gct gac cac agc cgc atg aag cgt gag gtt agc    761
Leu His Gln Leu Glu Ala Asp His Ser Arg Met Lys Arg Glu Val Ser
170             175             180             185 gca cac ttc cat gag gtg ctg agg ctg aag gac gag atg ctc agc ctc    809
Ala His Phe His Glu Val Leu Arg Leu Lys Asp Glu Met Leu Ser Leu
                190             195             200
```

FIG. 1A

```
tcg ctg cac tat agc aat gcg ctg cag gag aag gag ctg gcc gcc tca    857
Ser Leu His Tyr Ser Asn Ala Leu Gln Glu Lys Glu Leu Ala Ala Ser
            205                 210                 215 cgc tgc cgc agc ctg cag gag gag ctg tat cta ctg aag cag gag ctg    905
Arg Cys Arg Ser Leu Gln Glu Glu Leu Tyr Leu Leu Lys Gln Glu Leu
        220                 225                 230 cag cga gcc aac atg gtt tcc tcc tgt gag ctg aaa ttg caa gag cag    953
Gln Arg Ala Asn Met Val Ser Ser Cys Glu Leu Glu Leu Gln Glu Gln
    235                 240                 245 tcc ctg agg aca gcc agc gac cag gag tcc ggg gat gag gag ctg aac    1001
Ser Leu Arg Thr Ala Ser Asp Gln Glu Ser Gly Asp Glu Glu Leu Asn
250                 255                 260                 265 cgc ctg aag gag gag aat gag aaa ctg cgc tcg ctg act ttc agc ctg    1049
Arg Leu Lys Glu Glu Asn Glu Lys Leu Arg Ser Leu Thr Phe Ser Leu
                270                 275                 280 gcg gag aag gac att ctg gag cag agc ctg gac gag gcg cgg ggg agc    1097
Ala Glu Lys Asp Ile Leu Glu Gln Ser Leu Asp Glu Ala Arg Gly Ser
            285                 290                 295 cga cag gag ctg gtg gag cgc atc cac tcg ctg cgg gag cgg gcc gtg    1145
Arg Gln Glu Leu Val Glu Arg Ile His Ser Leu Arg Glu Arg Ala Val
        300                 305                 310 gct gcc gag agg cag cga gag cag tac tgg gaa gag aag gaa cag acc    1193
Ala Ala Glu Arg Gln Arg Glu Gln Tyr Trp Glu Glu Lys Glu Gln Thr
    315                 320                 325 ctg ctg cag ttc cag aag agt aag atg gcc tgc caa ctc tac agg gag    1241
Leu Leu Gln Phe Gln Lys Ser Lys Met Ala Cys Gln Leu Tyr Arg Glu
330                 335                 340                 345 aag gtg aat gcg ctg cag gcc cag gtg tgc gag ctg cag aag gag cga    1289
Lys Val Asn Ala Leu Gln Ala Gln Val Cys Glu Leu Gln Lys Glu Arg
                350                 355                 360 gac cag gcg tac tcc gcg agg gac agt gct cag agg gag att tcc cag    1337
Asp Gln Ala Tyr Ser Ala Arg Asp Ser Ala Gln Arg Glu Ile Ser Gln
            365                 370                 375 agc ctg gtg gag aag gac tcc ctc cgc agg cag gtg ttc gag ctg acg    1385
Ser Leu Val Glu Lys Asp Ser Leu Arg Arg Gln Val Phe Glu Leu Thr
        380                 385                 390 gac cag gtc tgc gag ctg cgc aca cag ctt cgc cag ctg cag gca gag    1433
Asp Gln Val Cys Glu Leu Arg Thr Gln Leu Arg Gln Leu Gln Ala Glu
    395                 400                 405 cct ccg ggt gtg ctc aag cag gaa gcc agg acc agg gag ccc tgt cca    1481
Pro Pro Gly Val Leu Lys Gln Glu Ala Arg Thr Arg Glu Pro Cys Pro
410                 415                 420                 425
```

FIG. 1B

```
cgg gag aag cag cgg ctg gtg cgg atg cat gcc atc tgc ccc aga gac    1529
Arg Glu Lys Gln Arg Leu Val Arg Met His Ala Ile Cys Pro Arg Asp
            430                 435                 440 gac agc gac tgc agc ctc gtc agc tcc aca gag tct cag ctc ttg tcg    1577
Asp Ser Asp Cys Ser Leu Val Ser Ser Thr Glu Ser Gln Leu Leu Ser
            445                 450                 455 gac ctg agt gcc acg tcc agc cgc gag ctg gtg gac agc ttc cgc tcc    1625
Asp Leu Ser Ala Thr Ser Ser Arg Glu Leu Val Asp Ser Phe Arg Ser
            460                 465                 470 agc agc ccc gcg ccc ccc agc cag cag tcc ctg tac aag cgg gtg gcc    1673
Ser Ser Pro Ala Pro Pro Ser Gln Gln Ser Leu Tyr Lys Arg Val Ala
            475                 480                 485 gag gac ttc ggg gaa gaa ccc tgg tct ttc agc agc tgc ctg gag atc    1721
Glu Asp Phe Gly Glu Glu Pro Trp Ser Phe Ser Ser Cys Leu Glu Ile
490                 495                 500                 505 ccg gag gga gac ccg gga gcc ctg ccg gga gct aag gca ggc gac cca    1769
Pro Glu Gly Asp Pro Gly Ala Leu Pro Gly Ala Lys Ala Gly Asp Pro
                    510                 515                 520 cac ctg gat tat gag ctc cta gac acg gca gac ctt ccg cag ctg gaa    1817
His Leu Asp Tyr Glu Leu Leu Asp Thr Ala Asp Leu Pro Gln Leu Glu
                525                 530                 535 agc agc ctg cag cca gtc tcc cct gga agg ctt gat gtc tcg gag agc    1865
Ser Ser Leu Gln Pro Val Ser Pro Gly Arg Leu Asp Val Ser Glu Ser
            540                 545                 550 ggc gtc ctc atg cgg cgg agg cca gcc cgc agg atc ctg agc cag gtc    1913
Gly Val Leu Met Arg Arg Arg Pro Ala Arg Arg Ile Leu Ser Gln Val
            555                 560                 565 acc atg ctg gcg ttc cag ggg gat gca ttg ctg gag cag atc agc gtc    1961
Thr Met Leu Ala Phe Gln Gly Asp Ala Leu Leu Glu Gln Ile Ser Val
570                 575                 580                 585 atc ggc ggg aac ctc acg ggc atc ttc atc cac cgg gtc acc ccg ggc    2009
Ile Gly Gly Asn Leu Thr Gly Ile Phe Ile His Arg Val Thr Pro Gly
                590                 595                 600 tcg gcg gcg gac cag atg gcc ttg cgc ccg ggc acc cag att gtg atg    2057
Ser Ala Ala Asp Gln Met Ala Leu Arg Pro Gly Thr Gln Ile Val Met
                605                 610                 615 gtt gat tac gaa gcc tca gag ccc ttg ttc aag gca gtc ctg gag gac    2105
Val Asp Tyr Glu Ala Ser Glu Pro Leu Phe Lys Ala Val Leu Glu Asp
            620                 625                 630 acg acc ctg gag gag gcc gtg ggg ctt ctc agg agg gtg gac ggc ttc    2153
Thr Thr Leu Glu Glu Ala Val Gly Leu Leu Arg Arg Val Asp Gly Phe
            635                 640                 645
```

FIG. 1C

```
tgc tgc ctg tct gtg aag gtc aac acg gac ggt tat aag agg cta ctc    2201
Cys Cys Leu Ser Val Lys Val Asn Thr Asp Gly Tyr Lys Arg Leu Leu
650             655             660             665 cag gac ctg gag gcc aaa gtg gcg acc tcg ggg gac tca ttc tac atc    2249
Gln Asp Leu Glu Ala Lys Val Ala Thr Ser Gly Asp Ser Phe Tyr Ile
            670             675             680 cgg gtc aac ctg gcc atg gag ggc agg gcc aaa ggg gag ctg cag gtg    2297
Arg Val Asn Leu Ala Met Glu Gly Arg Ala Lys Gly Glu Leu Gln Val
        685             690             695 cat tgc aac gag gtc ctg cac gtc acc gac acc atg ttc cag ggc tgc    2345
His Cys Asn Glu Val Leu His Val Thr Asp Thr Met Phe Gln Gly Cys
    700             705             710 ggc tgc tgg cat gcc cac cgc gtg aac tct tac acc atg aag gat act    2393
Gly Cys Trp His Ala His Arg Val Asn Ser Tyr Thr Met Lys Asp Thr
715             720             725 gcc gcg cac ggc acc atc ccc aac tac tcc agg gct cag cag cag ctc    2441
Ala Ala His Gly Thr Ile Pro Asn Tyr Ser Arg Ala Gln Gln Gln Leu
730             735             740             745 ata gcc ctc atc cag gac atg act cag cag tgc acc gtg acc cgc aag    2489
Ile Ala Leu Ile Gln Asp Met Thr Gln Gln Cys Thr Val Thr Arg Lys
            750             755             760 cca tct tct ggg gga cca cag aag ctg gtc cgc atc gtc agt atg gac    2537
Pro Ser Ser Gly Gly Pro Gln Lys Leu Val Arg Ile Val Ser Met Asp
        765             770             775 aaa gcc aag gcc agc cct ctg cgt ttg tcc ttt gac agg ggc cag ttg    2585
Lys Ala Lys Ala Ser Pro Leu Arg Leu Ser Phe Asp Arg Gly Gln Leu
    780             785             790 gac ccc agc agg atg gag ggc tcc agc acg tgc ttc tgg gcc gag agc    2633
Asp Pro Ser Arg Met Glu Gly Ser Ser Thr Cys Phe Trp Ala Glu Ser
795             800             805 tgc ctc acc ctg gtg ccc tat acc ctg gtg tgg ccc cat cga ccc gcc    2681
Cys Leu Thr Leu Val Pro Tyr Thr Leu Val Trp Pro His Arg Pro Ala
810             815             820             825 cgg ccc cgg cct gtg ctc ctc gtg ccc agg gcg gtt ggg aag atc ctg    2729
Arg Pro Arg Pro Val Leu Leu Val Pro Arg Ala Val Gly Lys Ile Leu
            830             835             840 agc gag aaa ctg tgc ctc ctc caa ggg ttt aag aag tgc ctg gca gag    2777
Ser Glu Lys Leu Cys Leu Leu Gln Gly Phe Lys Lys Cys Leu Ala Glu
        845             850             855 tac ttg agc cag gag gag tat gag gcc tgg agc cag aga ggg gac atc    2825
Tyr Leu Ser Gln Glu Glu Tyr Glu Ala Trp Ser Gln Arg Gly Asp Ile
860             865             870
```

FIG. 1D

```
atc cag gag gga gag gtg tcc ggg ggc cgc tgc tgg gtg acc cgc cat      2873
Ile Gln Glu Gly Glu Val Ser Gly Gly Arg Cys Trp Val Thr Arg His
        875                 880                 885 gct gtg gag tcc ctc atg gaa aag aac acc cat gcc ctc ctg gac gtc      2921
Ala Val Glu Ser Leu Met Glu Lys Asn Thr His Ala Leu Leu Asp Val
890                 895                 900                 905 cag ctg gac agt gtc tgc acc ctg cac agg atg gac atc ttc ccc atc      2969
Gln Leu Asp Ser Val Cys Thr Leu His Arg Met Asp Ile Phe Pro Ile
                910                 915                 920 gtc atc cac gtc tct gtc aac gag aag atg gca aag aag ctc aag aag      3017
Val Ile His Val Ser Val Asn Glu Lys Met Ala Lys Lys Leu Lys Lys
        925                 930                 935 ggc cta cag cgg ttg ggc acc tca gag gag cag ctc ctg gag gct gcg      3065
Gly Leu Gln Arg Leu Gly Thr Ser Glu Glu Gln Leu Leu Glu Ala Ala
        940                 945                 950 agg cag gag gag gga gac ctg gac cgg gcg ccc tgt cta tac agc agc      3113
Arg Gln Glu Glu Gly Asp Leu Asp Arg Ala Pro Cys Leu Tyr Ser Ser
        955                 960                 965 ctg gct cct gac ggc tgg agc gac ctg gac ggc ctg ctc agc tgt gtc      3161
Leu Ala Pro Asp Gly Trp Ser Asp Leu Asp Gly Leu Leu Ser Cys Val
970                 975                 980                 985 cgc cag gcc atc gcc gac gag cag aag aag gtg gtg tgg acg gag cag      3209
Arg Gln Ala Ile Ala Asp Glu Gln Lys Lys Val Val Trp Thr Glu Gln
                990                 995                 1000 agc ccc cga tga tgcaccgtgc cccttccgg gactgtgggg gcttctgtgt           3261
Ser Pro Arg
```

```
gcctgttaat gcagtcctgt tcctcagccc aggccctctt ggcacagctg tgggctcctt    3321
ggcacatgag gccggctctc cccactggct ggggtctaac cttgaaccct caccacgtgc    3381
aggtcacaca cagtgaagcc acttgtaact gcacactttt ctgtggaaac atcttcaccc    3441
tttaccaggc ttggcatggt ctgaactgga aaccctgaga atgtttctgc agtaggacag    3501
gagggacatc ttcccatgcc ttccctagaa ccggaggccc cggacttctc tggaaaaccg    3561
cctgtctgca ggcccgattc aaatctatgg gggctgcact tccctttac attttgatgt     3621
gtcaaaggct tttggagtga ccaaaagcac agaggcagcg ggtggggcgc ctgggtggtc    3681
cccaaggtcg ctgccaccct tgcccggggc agaggcataa gcccacatat gctgtgacgc    3741
tggccacctt ttctcagctt ctgaggctgc gatgcctcag gaactccagt ttacagagac    3801
cagtgtgttt acttgtaaat aaagcctctg ggtggtggag acgtactttt cagtgggtct    3861
gtgcccgtg gcccctgtgc ctgttcggtg ggggtgtccc agagaagcct ggcaccagta     3921
ccccgtcaa                                                           3931
```

FIG. 1E

```
  M   G   E   L   C   R   R   D   S   A   L   T   A   L   D   E   E   T   L   W      20
ATG GGG GAA CTG TGC CGC AGG GAC TCC GCA CTC ACG GCA CTG GAC GAG GAG ACA CTG TGG      60

E   M   M   E   S   H   R   H   R   I   V   R   C   I   C   P   S   R   L   T      40
GAG ATG ATG GAG AGC CAC CGC CAC AGG ATC GTA CGC TGC ATC TGC CCC AGC CGC CTC ACC     120

P   Y   L   R   Q   A   K   V   L   C   Q   L   D   E   E   E   V   L   H   S      60
CCC TAC CTG CGC CAG GCC AAG GTG CTG TGC CAG CTG GAC GAG GAG GAG GTG CTG CAC AGC     180

P   R   L   T   N   S   A   M   R   A   G   H   L   L   D   L   L   K   T   R      80
CCC CGG CTC ACC AAC AGC GCC ATG CGG GCC GGG CAC TTG CTG GAT TTG CTG AAG ACT CGA     240

G   K   N   G   A   I   A   F   L   E   S   L   K   F   H   N   P   D   V   Y     100
GGG AAG AAC GGG GCC ATC GCC TTC CTG GAG AGC CTG AAG TTC CAC AAC CCT GAC GTC TAC     300

T   L   V   T   G   L   Q   P   D   V   D   F   S   N   F   S   G   E   S   S     120
ACC CTG GTC ACC GGG CTG CAG CCT GAT GTT GAC TTC AGT AAC TTT AGC GGT GAG AGC TCC     360

D   F   D   G   L   A   G   T   S   R   N   L   R   L   L   V   T   P   G   L     140
GAC TTT GAC GGT TTG GCA GGC ACT TCT AGG AAC CTC AGG CTC CTG GTA ACC CCA GGT CTC     420

M   E   T   S   K   L   T   E   C   L   A   G   A   I   G   S   L   Q   E   E     160
ATG GAG ACA TCC AAG CTG ACC GAG TGC CTG GCT GGG GCC ATC GGC AGC CTG CAG GAG GAG     480

L   N   Q   E   K   G   Q   K   E   V   L   L   R   R   C   Q   Q   L   Q   E     180
CTG AAC CAG GAA AAG GGG CAG AAG GAG GTG CTG CTG CGG CGG TGC CAG CAG CTG CAG GAG     540

H   L   G   L   A   E   T   R   A   E   G   L   H   Q   L   E   A   D   H   S     200
CAC CTG GGC CTG GCC GAG ACC CGT GCC GAG GGC CTG CAC CAG CTG GAG GCT GAC CAC AGC     600

R   M   K   R   E   V   S   A   H   F   H   E   V   L   R   L   K   D   E   M     220
CGC ATG AAG CGT GAG GTT AGC GCA CAC TTC CAT GAG GTG CTG AGG CTG AAG GAC GAG ATG     660

L   S   L   S   L   H   Y   S   N   A   L   Q   E   K   E   L   A   A   S   R     240
CTC AGC CTC TCG CTG CAC TAT AGC AAT GCG CTG CAG GAG AAG GAG CTG GCC GCC TCA CGC     720

C   R   S   L   Q   E   E   L   Y   L   L   K   Q   E   L   Q   R   A   N   M     260
TGC CGC AGC CTG CAG GAG GAG CTG TAT CTA CTG AAG CAG GAG CTG CAG CGA GCC AAC ATG     780

V   S   S   C   E   L   E   L   Q   E   Q   S   L   R   T   A   S   D   Q   E     280
GTT TCC TCC TGT GAG CTG GAA TTG CAA GAG CAG TCC CTG AGG ACA GCC AGC GAC CAG GAG     840

S   G   D   E   E   L   N   R   L   K   E   E   N   E   K   L   R   S   L   T     300
TCC GGG GAT GAG GAG CTG AAC CGC CTG AAG GAG GAG AAT GAG AAA CTG CGC TCG CTG ACT     900

F   S   L   A   E   K   D   I   L   E   Q   S   L   D   E   A   R   G   S   R     320
TTC AGC CTG GCG GAG AAG GAC ATT CTG GAG CAG AGC CTC GAC GAG GCG CGG GGG AGC CGA     960

Q   E   L   V   E   R   I   H   S   L   R   E   R   A   V   A   A   E   R   Q     340
CAG GAG CTG GTG GAG CGC ATC CAC TCG CTG CGG GAG CGG GCC GTG GCT GCC GAG AGG CAG    1020

R   E   Q   A   R   P   S   E   L   L   S   F   T   V   H   V   S   H   S   V     360
CGA GAG CAG GCC AGA CCC TCA GAG CTG CTG AGC TTC ACG GTC CAT GTG TCC CAC TCT GTC    1080

Q   Y   W   E   E   K   E   Q   T   L   L   Q   F   Q   K   S   K   M   A   C     380
CAG TAC TGG GAA GAG AAG GAA CAG ACC CTG CTG CAG TTC CAG AAG AGT AAG ATG GCC TGC    1140

Q   L   Y   R   E   K   V   N   A   L   Q   A   Q   V   C   E   L   Q   K   E     400
CAA CTC TAC AGG GAG AAG GTG AAT GCG CTG CAG GCC CAG GTG TGC GAG CTG CAG AAG GAG    1200

R   D   Q   A   Y   S   A   R   D   S   A   Q   R   E   I   S   Q   S   L   V     420
CGA GAC CAG GCG TAC TCC GCG AGG GAC AGT GCT CAG AGG GAG ATT TCC CAG AGC CTG GTG    1260

E   K   D   S   L   R   R   Q   V   F   E   L   T   D   Q   V   C   E   L   R     440
GAG AAG GAC TCC CTC CGC AGG CAG GTG TTC GAG CTG ACG GAC CAG GTC TGC GAG CTG CGC    1320
```

FIG. 2A

```
      T   Q   L   R   Q   L   Q   A   E   P   P   G   V   L   K   Q   E   A   R   T   460
     ACA CAG CTT CGC CAG CTG CAG GCA GAG CCT CCG GGT GTG CTC AAG CAG GAA GCC AGG ACC 1380

R   E   P   C   P   R   E   K   Q   R   L   V   R   M   H   A   I   C   P   R   480
     AGG GAG CCC TGT CCA CGG GAG AAG CAG CGG CTG GTG CGG ATG CAT GCC ATC TGC CCC AGA 1440

D   D   S   D   C   S   L   V   S   S   T   E   S   Q   L   L   S   D   L   S   500
     GAC GAC AGC GAC TGC AGC CTC GTC AGC TCC ACA GAG TCT CAG CTC TTG TCG GAC CTG AGT 1500

A   T   S   S   R   E   L   V   D   S   F   R   S   S   P   A   P   P   S   520
     GCC ACG TCC AGC CGC GAG CTG GTG GAC AGC TTC CGC TCC AGC AGC CCC GCG CCC CCC AGC 1560

Q   Q   S   L   Y   K   R   V   A   E   D   F   G   E   E   P   W   S   F   S   540
     CAG CAG TCC CTG TAC AAG CGG GTG GCC GAG GAC TTC GGG GAA GAA CCC TGG TCT TTC AGC 1620

S   C   L   E   I   P   E   G   D   P   G   A   L   P   G   A   K   A   G   D   560
     AGC TGC CTG GAG ATC CCG GAG GGA GAC CCG GGA GCC CTG CCG GGA GCT AAG GCA GGC GAC 1680

P   H   L   D   Y   E   L   L   D   T   A   D   L   P   Q   L   E   S   S   L   580
     CCA CAC CTG GAT TAT GAG CTC CTA GAC ACG GCA GAC CTT CCG CAG CTG GAA AGC AGC CTG 1740

Q   P   V   S   P   G   R   L   D   V   S   E   S   A   Q   A   G   R   L   P   600
     CAG CCA GTC TCC CCT GGA AGG CTT GAT GTC TCG GAG AGT GCA CAA GCC GGT CGT CTC CCG 1800

A   C   S   G   V   L   M   R   R   R   P   A   R   R   I   L   S   Q   V   T   620
     GCC TGC AGC GGC GTC CTC ATG CGG CGG AGG CCA GCC CGC AGG ATC CTG AGC CAG GTC ACC 1860

M   L   A   F   Q   G   D   A   L   L   E   Q   I   S   V   I   G   G   N   L   640
     ATG CTG GCG TTC CAG GGG GAT GCA TTG CTG GAG CAG ATC AGC GTC ATC GGC GGG AAC CTC 1920

T   G   I   F   I   H   R   V   T   P   G   S   A   A   D   Q   M   A   L   R   660
     ACG GGC ATC TTC ATC CAC CGG GTC ACC CCG GGC TCG GCG GCG GAC CAG ATG GCC TTG CGC 1980

P   G   T   Q   I   V   M   V   D   Y   E   A   S   E   P   L   F   K   A   V   680
     CCG GGC ACC CAG ATT GTG ATG GTT GAT TAC GAA GCC TCA GAG CCC TTG TTC AAG GCA GTC 2040

L   E   D   T   T   L   E   E   A   V   G   L   L   R   R   V   D   G   F   C   700
     CTG GAG GAC ACG ACC CTG GAG GAG GCC GTG GGG CTT CTC AGG AGG GTG GAC GGC TTC TGC 2100

C   L   S   V   K   V   N   T   D   G   Y   K   R   L   L   Q   D   L   E   A   720
     TGC CTG TCT GTG AAG GTC AAC ACG GAC GGT TAT AAG AGG CTA CTC CAG GAC CTG GAG GCC 2160

K   V   A   T   S   G   D   S   F   Y   I   R   V   N   L   A   M   E   G   R   740
     AAA GTG GCG ACC TCG GGG GAC TCA TTC TAC ATC CGG GTC AAC CTG GCC ATG GAG GGC AGG 2220

A   K   G   E   L   Q   V   H   C   N   E   V   L   H   V   T   D   T   M   F   760
     GCC AAA GGG GAG CTG CAG GTG CAT TGC AAC GAG GTC CTG CAC GTC ACC GAC ACC ATG TTC 2280

Q   G   C   G   C   W   H   A   H   R   V   N   S   Y   T   M   K   D   T   A   780
     CAG GGC TGC GGC TGC TGG CAT GCC CAC CGC GTG AAC TCT TAC ACC ATG AAG GAT ACT GCC 2340

A   H   G   T   I   P   N   Y   S   R   A   Q   Q   Q   L   I   A   L   I   Q   800
     GCG CAC GGC ACC ATC CCC AAC TAC TCC AGG GCT CAG CAG CAG CTC ATA GCC CTC ATC CAG 2400

D   M   T   Q   Q   C   T   V   T   R   K   P   S   S   G   G   P   Q   K   L   820
     GAC ATG ACT CAG CAG TGC ACC GTG ACC CGC AAG CCA TCT TCT GGG GGA CCA CAG AAG CTG 2460

V   R   I   V   S   M   D   K   A   K   A   S   P   L   R   L   S   F   D   R   840
     GTC CGC ATC GTC AGT ATG GAC AAA GCC AAG GCC AGC CCT CTG CGT TTG TCC TTT GAC AGG 2520

G   Q   L   D   P   S   R   M   E   G   S   S   T   C   F   W   A   E   S   C   860
     GGC CAG TTG GAC CCC AGC AGG ATG GAG GGC TCC AGC ACG TGC TTC TGG GCC GAG AGC TGC 2580

L   T   L   V   P   Y   T   L   V   R   P   H   R   P   A   R   P   R   P   V   880
     CTC ACC CTG GTG CCC TAT ACC CTG GTG CGG CCC CAT CGA CCC GCC CGG CCC CGG CCT GTG 2640

L   L   V   P   R   A   V   G   K   I   L   S   E   K   L   C   L   L   Q   G   900
     CTC CTC GTG CCC AGG GCG GTT GGG AAG ATC CTG AGC GAG AAA CTG TGC CTC CTC CAA GGG 2700

F   K   K   C   L   A   E   Y   L   S   Q   E   E   Y   E   A   W   S   Q   R   920
     TTT AAG AAG TGC CTG GCA GAG TAC TTG AGC CAG GAG GAG TAT GAG GCC TGG AGC CAG AGA 2760
```

FIG. 2B

```
      G   D   I   I   Q   E   G   E   V   S   G   G   R   C   W   V   T   R   H   A    940
     GGG GAC ATC ATC CAG GAG GGA GAG GTG TCC GGG GGC CGC TGC TGG GTG ACC CGC CAT GCT   2820

V   E   S   L   M   E   K   N   T   H   A   L   L   D   V   Q   L   D   S   V    960
     GTG GAG TCC CTC ATG GAA AAG AAC ACC CAT GCC CTC CTG GAC GTC CAG CTG GAC AGT GTC   2880

C   T   L   H   R   M   D   I   F   P   I   V   I   H   V   S   V   N   E   K    980
     TGC ACC CTG CAC AGG ATG GAC ATC TTC CCC ATC GTC ATC CAC GTC TCT GTC AAC GAG AAG   2940

M   A   K   K   L   K   K   G   L   Q   R   L   G   T   S   E   E   Q   L   L   1000
     ATG GCA AAG AAG CTC AAG AAG GGC CTA CAG CGG TTG GGC ACC TCA GAG GAG CAG CTC CTG   3000

E   A   R   Q   E   E   G   D   L   D   R   A   P   C   L   Y   S   S   L   1020
     GAG GCT GCG AGG CAG GAG GAG GGA GAC CTG GAC CGG GCG CCC TGT CTA TAC AGC AGC CTG   3060

A   P   D   G   W   S   D   L   D   G   L   L   S   C   V   R   Q   A   I   A   1040
     GCT CCT GAC GGC TGG AGC GAC CTG GAC GGC CTG CTC AGC TGT GTC CGC CAG GCC ATC GCC   3120

D   E   Q   K   K   V   Q   R   R   H   P   R   I   N   P   S   Q   R   T   1060
     GAC GAG CAG AAG AAG GTG CAA CGC CGA CGT CAT CCA AGA ATT AAC CCA AGC CAG AGG ACG   3180

G   I   A   T   Q   Q   R   Q   C   H   R   R   I   N   P   R   Q   R   M   G   1080
     GGC ATC GCC ACC CAG CAA CGC CAG TGT CAC CGA AGA ATT AAC CCA AGG CAG AGG ATG GGC   3240

I   A   T   Q   Q   R   Q   C   H   R   R   I   N   P   S   Q   R   T   G   I   1100
     ATT GCC ACC CAG CAA CGC CAG TGT CAC CGA AGA ATT AAC CCA AGC CAG AGG ACG GGC ATC   3300

T   T   Q   Q   C   Q   C   H   R   R   I   N   P   S   Q   R   T   G   I   A   1120
     ACC ACC CAG CAA TGC CAG TGT CAC CGA AGA ATT AAC CCA AGC CAG AGG ACG GGC ATC GCC   3360

M   P   S   S   S   D   T   L   K   K   D   K   L   L   P   R   N   T   T       1139
     ATG CCT TCA TCT TCG GAC ACT CTC AAA AAA GAT AAG CTT CTG CCC AGA AAC ACC ACA       3417
```

FIG. 2C

CARD: domain 1 of 1, from 16 to 107: score -4.1, E = 0.94
\*->aeddrrllrknrlelIgeltlsglldhLleknvLteeeeEkikaknt
+e + + +r + + +++s l +L++++vL + +eE++ +
CARD14    16    EETLWEMMESHRHRIVRCICPSRLTPYLRQAKVLCQLDEEEVLHSPR    62 trr..dkareLiDsvqkkGnqAfqiFlqaLretdgelladllde<-\*
+ + +a L+D ++++G + + +Fl++L+ +++ + + +
CARD14    63    LTNsaMRAGHLLDLLKTRGKNGAIAFLESLKFHNPDVYTLVTGLQ    107

FIG. 5A

PDZ: domain 1 of 1, from 568 to 659: score 5.3, E = 0.39
\*->eitlekevkrgglGfsikggsdk..givvsevlpGsgaAeagGrLke
++t+ ++ l +i++ + + +gi++ +v pG +aA++ L++
CARD14    568    QVTMLAF-QGDALLEQISVIGGNltGIFIHRVTPG-SAADQMA-LRP    611

GDvIlsvNG.......qdvenmsheravlaikgsgg..evtLtvlRd<--
G +I+ v+ + +++ + +e+ ++e+av +++ g ++++v d
CARD14    612    GTQIVMVDYeaseplfkAVLEDTTLEEAVGLLRRVDGfcCLSVKVNTD    659

CARD14    -    -    \*        -    -

FIG. 5B

SH3_2: domain 1 of 1, from 679 to 744: score -4.5, E = 3.8

```
              *->eyvvAlYDyeaqnedELsFkkGDiitvleks..ddgwweGelnr...
                 +y ++ + e++ +EL ++ +++++V++       ++ g w+ + ++ +
CARD14   679     FYIRVNLAMEGRAKGELQVHCNEVLHVTDTMfgGCGCWHAHRVNsyt   725

...tGkeGlfPsnYVeeie<-*
                 ++t  G +P   + ++
CARD14   726     mkdTAAHGTIPNYSRAQQQ   744
```

FIG. 5C

Guanylate_kin: domain 1 of 1, from 856 to 948: score -24.2, E = 0.073

```
              *->TRpVPRpgEvdGkdYhFVssrEemekdIaaneFlEygefggnYYGTs
                 +++s Ee e+ ++++ +  ge++g          +
CARD14   856     --A-------EYLS-QEEYEAWSQRGDIIQEGEVSGGRCWVT   887 letvrqvakqgKiciLDvepQgvkrlrtaelsNPivvFlaPpsl..qele
                 +++v+    +++ +++LDv ++ v l + Piv+   +  + l+
CARD14   888     RHAVESLMEKNTHALLDVQLDSVCTLHRMDIF-PIVIHVSVNEKmaKKLK   936 krLegrnkesEes<-*
                 k L+++++ sEe+
CARD14   937     KGLQRLGT-SEEQ   948
```

FIG. 5D

```
K-box: domain 1 of 1, from 239 to 325: score -36.5, E = 2.9
          *->dsyqkssgnss..lwesnyqnwqgEaaKLkaqienLQnNrnqRhllG
             s+ ++++    ++    +s++++   +E+++Lk+++e+L+  +
CARD14  239  VSSCELELQEQslRTASDQESGDEELNRLKEENEKLR--SL------  277

EdLgsLslKElqqLEgqLekgLkhIRsrKngllldgieelqkKErelqee
             + sl E    LEg L+++     R   + l+ i+ ++ + +  +
CARD14  278  ----TFSLAEKDILEQSLDEA----RGSRQE-LVERIHSLRERAVAAERQ  318

NkaLrkKiee<-*
             +   + +ee
CARD14  319  RE---QYWEE    325
```

FIG. 5E

SEQUENCE LISTING

```
<160> NUMBER OF SEQ ID NOS: 10

<210> SEQ ID NO 1
<211> LENGTH: 3931
<212> TYPE: DNA
<213> ORGANISM: Homo sapiens
<220> FEATURE:
<221> NAME/KEY: CDS
<222> LOCATION: (207)...(3218)

<400> SEQUENCE: 1
attcggctcg agttcacctg gtgctgcttt gacttcaggc tcttccttct gcccagctcc      60
gtcccaccca gcagcccgca gagaaaggag gcagctggca ccacactggg ctttggagac     120
actgcgggga ctgtggaccc cacccttgctg cacggagctc ctgcaaaagc aaacctgaga    180
accttgggtc ctcccagcgc ccagcc atg ggg gaa ctg tgc cgc agg gac tcc     233
                              Met Gly Glu Leu Cys Arg Arg Asp Ser
```

-continued

```
                1             5
gca ctc acg gca ctg gac gag gag aca ctg tgg gag atg atg gag agc      281
Ala Leu Thr Ala Leu Asp Glu Glu Thr Leu Trp Glu Met Met Glu Ser
 10              15                  20                  25 cac cgc cac agg atc gta cgc tgc atc tgc ccc agc cgc ctc acc ccc      329
His Arg His Arg Ile Val Arg Cys Ile Cys Pro Ser Arg Leu Thr Pro
             30                  35                  40 tac ctg cgc cag gcc aag gtg ctg tgc cag ctg gac gag gag gag gtg      377
Tyr Leu Arg Gln Ala Lys Val Leu Cys Gln Leu Asp Glu Glu Glu Val
         45                  50                  55 ctg cac agc ccc cgg ctc acc aac agc gcc atg cgg gcc ggg cac ttg      425
Leu His Ser Pro Arg Leu Thr Asn Ser Ala Met Arg Ala Gly His Leu
             60                  65                  70 ctg gat ttg ctg aag act cga ggg aag aac ggg gcc atc gcc ttc ctg      473
Leu Asp Leu Leu Lys Thr Arg Gly Lys Asn Gly Ala Ile Ala Phe Leu
 75                  80                  85 gag agc ctg aag ttc cac aac cct gac gtc tac acc ctg gtc acc ggg      521
Glu Ser Leu Lys Phe His Asn Pro Asp Val Tyr Thr Leu Val Thr Gly
 90                  95                 100                 105 ctg cag cct gat gtt gac ttc agt aac ttt agc ggt ctc atg gag aca      569
Leu Gln Pro Asp Val Asp Phe Ser Asn Phe Ser Gly Leu Met Glu Thr
             110                 115                 120 tcc aag ctg acc gag tgc ctg gct ggg gcc atc ggc agc ctg cag gag      617
Ser Lys Leu Thr Glu Cys Leu Ala Gly Ala Ile Gly Ser Leu Gln Glu
         125                 130                 135 gag ctg aac cag gaa aag ggg cag aag gag gtg ctg ctg cgg cgg tgc      665
Glu Leu Asn Gln Glu Lys Gly Gln Lys Glu Val Leu Leu Arg Arg Cys
         140                 145                 150 cag cag ctg cag gag cac ctg ggc ctg gcc gag acc cgt gcc gag ggc      713
Gln Gln Leu Gln Glu His Leu Gly Leu Ala Glu Thr Arg Ala Glu Gly
         155                 160                 165 ctg cac cag ctg gag gct gac cac agc cgc atg aag cgt gag gtt agc      761
Leu His Gln Leu Glu Ala Asp His Ser Arg Met Lys Arg Glu Val Ser
 170                 175                 180                 185 gca cac ttc cat gag gtg ctg agg ctg aag gac gag atg ctc agc ctc      809
Ala His Phe His Glu Val Leu Arg Leu Lys Asp Glu Met Leu Ser Leu
             190                 195                 200 tcg ctg cac tat agc aat gcg ctg cag gag aag gag ctg gcc gcc tca      857
Ser Leu His Tyr Ser Asn Ala Leu Gln Glu Lys Glu Leu Ala Ala Ser
         205                 210                 215 cgc tgc cgc agc ctg cag gag gag ctg tat cta ctg aag cag gag ctg      905
Arg Cys Arg Ser Leu Gln Glu Glu Leu Tyr Leu Leu Lys Gln Glu Leu
         220                 225                 230 cag cga gcc aac atg gtt tcc tcc tgt gag ctg gaa ttg caa gag cag      953
Gln Arg Ala Asn Met Val Ser Ser Cys Glu Leu Glu Leu Gln Glu Gln
 235                 240                 245 tcc ctg agg aca gcc agc gac cag gag tcc ggg gat gag gag ctg aac      1001
Ser Leu Arg Thr Ala Ser Asp Gln Glu Ser Gly Asp Glu Glu Leu Asn
250                 255                 260                 265 cgc ctg aag gag gag aat gag aaa ctg cgc tcg ctg act ttc agc ctg      1049
Arg Leu Lys Glu Glu Asn Glu Lys Leu Arg Ser Leu Thr Phe Ser Leu
             270                 275                 280 gcg gag aag gac att ctg gag cag agc ctg gac gag gcg cgg ggg agc      1097
Ala Glu Lys Asp Ile Leu Glu Gln Ser Leu Asp Glu Ala Arg Gly Ser
         285                 290                 295 cga cag gag ctg gtg gag cgc atc cac tcg ctg cgg gag cgg gcc gtg      1145
Arg Gln Glu Leu Val Glu Arg Ile His Ser Leu Arg Glu Arg Ala Val
         300                 305                 310 gct gcc gag agg cag cga gag cag tac tgg gaa gag aag gaa cag acc      1193
```

-continued

| | |
|---|---|
| Ala Ala Glu Arg Gln Arg Glu Gln Tyr Trp Glu Glu Lys Glu Gln Thr<br>315 320 325 | |
| ctg ctg cag ttc cag aag agt aag atg gcc tgc caa ctc tac agg gag<br>Leu Leu Gln Phe Gln Lys Ser Lys Met Ala Cys Gln Leu Tyr Arg Glu<br>330 335 340 345 | 1241 |
| aag gtg aat gcg ctg cag gcc cag gtg tgc gag ctg cag aag gag cga<br>Lys Val Asn Ala Leu Gln Ala Gln Val Cys Glu Leu Gln Lys Glu Arg<br>350 355 360 | 1289 |
| gac cag gcg tac tcc gcg agg gac agt gct cag agg gag att tcc cag<br>Asp Gln Ala Tyr Ser Ala Arg Asp Ser Ala Gln Arg Glu Ile Ser Gln<br>365 370 375 | 1337 |
| agc ctg gtg gag aag gac tcc ctc cgc agg cag gtg ttc gag ctg acg<br>Ser Leu Val Glu Lys Asp Ser Leu Arg Arg Gln Val Phe Glu Leu Thr<br>380 385 390 | 1385 |
| gac cag gtc tgc gag ctg cgc aca cag ctt cgc cag ctg cag gca gag<br>Asp Gln Val Cys Glu Leu Arg Thr Gln Leu Arg Gln Leu Gln Ala Glu<br>395 400 405 | 1433 |
| cct ccg ggt gtg ctc aag cag gaa gcc agg acc agg gag ccc tgt cca<br>Pro Pro Gly Val Leu Lys Gln Glu Ala Arg Thr Arg Glu Pro Cys Pro<br>410 415 420 425 | 1481 |
| cgg gag aag cag cgg ctg gtg cgg atg cat gcc atc tgc ccc aga gac<br>Arg Glu Lys Gln Arg Leu Val Arg Met His Ala Ile Cys Pro Arg Asp<br>430 435 440 | 1529 |
| gac agc gac tgc agc ctc gtc agc tcc aca gag tct cag ctc ttg tcg<br>Asp Ser Asp Cys Ser Leu Val Ser Ser Thr Glu Ser Gln Leu Leu Ser<br>445 450 455 | 1577 |
| gac ctg agt gcc acg tcc agc cgc gag ctg gtg gac agc ttc cgc tcc<br>Asp Leu Ser Ala Thr Ser Ser Arg Glu Leu Val Asp Ser Phe Arg Ser<br>460 465 470 | 1625 |
| agc agc ccc gcg ccc ccc agc cag cag tcc ctg tac aag cgg gtg gcc<br>Ser Ser Pro Ala Pro Pro Ser Gln Gln Ser Leu Tyr Lys Arg Val Ala<br>475 480 485 | 1673 |
| gag gac ttc ggg gaa gaa ccc tgg tct ttc agc agc tgc ctg gag atc<br>Glu Asp Phe Gly Glu Glu Pro Trp Ser Phe Ser Ser Cys Leu Glu Ile<br>490 495 500 505 | 1721 |
| ccg gag gga gac ccg gga gcc ctg ccg gga gct aag gca ggc gac cca<br>Pro Glu Gly Asp Pro Gly Ala Leu Pro Gly Ala Lys Ala Gly Asp Pro<br>510 515 520 | 1769 |
| cac ctg gat tat gag ctc cta gac acg gca gac ctt ccg cag ctg gaa<br>His Leu Asp Tyr Glu Leu Leu Asp Thr Ala Asp Leu Pro Gln Leu Glu<br>525 530 535 | 1817 |
| agc agc ctg cag cca gtc tcc cct gga agg ctt gat gtc tcg gag agc<br>Ser Ser Leu Gln Pro Val Ser Pro Gly Arg Leu Asp Val Ser Glu Ser<br>540 545 550 | 1865 |
| ggc gtc ctc atg cgg cgg agg cca gcc cgc agg atc ctg agc cag gtc<br>Gly Val Leu Met Arg Arg Arg Pro Ala Arg Arg Ile Leu Ser Gln Val<br>555 560 565 | 1913 |
| acc atg ctg gcc ttc cag ggg gat gca ttg ctg gag cag atc agc gtc<br>Thr Met Leu Ala Phe Gln Gly Asp Ala Leu Leu Glu Gln Ile Ser Val<br>570 575 580 585 | 1961 |
| atc ggc ggg aac ctc acg ggc atc ttc atc cac cgg gtc acc ccg ggc<br>Ile Gly Gly Asn Leu Thr Gly Ile Phe Ile His Arg Val Thr Pro Gly<br>590 595 600 | 2009 |
| tcg gcg gcg gac cag atg gcc ttg cgc ccg ggc acc cag att gtg atg<br>Ser Ala Ala Asp Gln Met Ala Leu Arg Pro Gly Thr Gln Ile Val Met<br>605 610 615 | 2057 |
| gtt gat tac gaa gcc tca gag ccc ttg ttc aag gca gtc ctg gag gac<br>Val Asp Tyr Glu Ala Ser Glu Pro Leu Phe Lys Ala Val Leu Glu Asp<br>620 625 630 | 2105 |

```
acg acc ctg gag gag gcc gtg ggg ctt ctc agg agg gtg gac ggc ttc    2153
Thr Thr Leu Glu Glu Ala Val Gly Leu Leu Arg Arg Val Asp Gly Phe
        635                 640                 645 tgc tgc ctg tct gtg aag gtc aac acg gac ggt tat aag agg cta ctc    2201
Cys Cys Leu Ser Val Lys Val Asn Thr Asp Gly Tyr Lys Arg Leu Leu
650                 655                 660                 665 cag gac ctg gag gcc aaa gtg gcg acc tcg ggg gac tca ttc tac atc    2249
Gln Asp Leu Glu Ala Lys Val Ala Thr Ser Gly Asp Ser Phe Tyr Ile
                670                 675                 680 cgg gtc aac ctg gcc atg gag ggc agg gcc aaa ggg gag ctg cag gtg    2297
Arg Val Asn Leu Ala Met Glu Gly Arg Ala Lys Gly Glu Leu Gln Val
            685                 690                 695 cat tgc aac gag gtc ctg cac gtc acc gac acc atg ttc cag ggc tgc    2345
His Cys Asn Glu Val Leu His Val Thr Asp Thr Met Phe Gln Gly Cys
        700                 705                 710 ggc tgc tgg cat gcc cac cgc gtg aac tct tac acc atg aag gat act    2393
Gly Cys Trp His Ala His Arg Val Asn Ser Tyr Thr Met Lys Asp Thr
715                 720                 725 gcc gcg cac ggc acc atc ccc aac tac tcc agg gct cag cag cag ctc    2441
Ala Ala His Gly Thr Ile Pro Asn Tyr Ser Arg Ala Gln Gln Gln Leu
730                 735                 740                 745 ata gcc ctc atc cag gac atg act cag cag tgc acc gtg acc cgc aag    2489
Ile Ala Leu Ile Gln Asp Met Thr Gln Gln Cys Thr Val Thr Arg Lys
                750                 755                 760 cca tct tct ggg gga cca cag aag ctg gtc cgc atc gtc agt atg gac    2537
Pro Ser Ser Gly Gly Pro Gln Lys Leu Val Arg Ile Val Ser Met Asp
            765                 770                 775 aaa gcc aag gcc agc cct ctg cgt ttg tcc ttt gac agg ggc cag ttg    2585
Lys Ala Lys Ala Ser Pro Leu Arg Leu Ser Phe Asp Arg Gly Gln Leu
        780                 785                 790 gac ccc agc agg atg gag ggc tcc agc acg tgc ttc tgg gcc gag agc    2633
Asp Pro Ser Arg Met Glu Gly Ser Ser Thr Cys Phe Trp Ala Glu Ser
795                 800                 805 tgc ctc acc ctg gtg ccc tat acc ctg gtg tgg ccc cat cga ccc gcc    2681
Cys Leu Thr Leu Val Pro Tyr Thr Leu Val Trp Pro His Arg Pro Ala
810                 815                 820                 825 cgg ccc cgg cct gtg ctc ctc gtg ccc agg gcg gtt ggg aag atc ctg    2729
Arg Pro Arg Pro Val Leu Leu Val Pro Arg Ala Val Gly Lys Ile Leu
                830                 835                 840 agc gag aaa ctg tgc ctc ctc caa ggg ttt aag aag tgc ctg gca gag    2777
Ser Glu Lys Leu Cys Leu Leu Gln Gly Phe Lys Lys Cys Leu Ala Glu
            845                 850                 855 tac ttg agc cag gag gag tat gag gcc tgg agc cag aga ggg gac atc    2825
Tyr Leu Ser Gln Glu Glu Tyr Glu Ala Trp Ser Gln Arg Gly Asp Ile
        860                 865                 870 atc cag gag gga gag gtg tcc ggg ggc cgc tgc tgg gtg acc cgc cat    2873
Ile Gln Glu Gly Glu Val Ser Gly Gly Arg Cys Trp Val Thr Arg His
875                 880                 885 gct gtg gag tcc ctc atg gaa aag aac acc cat gcc ctc ctg gac gtc    2921
Ala Val Glu Ser Leu Met Glu Lys Asn Thr His Ala Leu Leu Asp Val
890                 895                 900                 905 cag ctg gac agt gtc tgc acc ctg cac agg atg gac atc ttc ccc atc    2969
Gln Leu Asp Ser Val Cys Thr Leu His Arg Met Asp Ile Phe Pro Ile
                910                 915                 920 gtc atc cac gtc tct gtc aac gag aag atg gca aag aag ctc aag aag    3017
Val Ile His Val Ser Val Asn Glu Lys Met Ala Lys Lys Leu Lys Lys
            925                 930                 935 ggc cta cag cgg ttg ggc acc tca gag gag cag ctc ctg gag gct gcg    3065
Gly Leu Gln Arg Leu Gly Thr Ser Glu Glu Gln Leu Leu Glu Ala Ala
        940                 945                 950
```

-continued

```
agg cag gag gag gga gac ctg gac cgg gcg ccc tgt cta tac agc agc    3113
Arg Gln Glu Glu Gly Asp Leu Asp Arg Ala Pro Cys Leu Tyr Ser Ser
    955                 960                 965 ctg gct cct gac ggc tgg agc gac ctg gac ggc ctg ctc agc tgt gtc    3161
Leu Ala Pro Asp Gly Trp Ser Asp Leu Asp Gly Leu Leu Ser Cys Val
970                 975                 980                 985 cgc cag gcc atc gcc gac gag cag aag aag gtg gtg tgg acg gag cag    3209
Arg Gln Ala Ile Ala Asp Glu Gln Lys Lys Val Val Trp Thr Glu Gln
                990                 995                 1000 agc ccc cga tgatgcaccg tgcccttcc cgggactgtg ggggcttctg              3258
Ser Pro Arg tgtgcctgtt aatgcagtcc tgttcctcag cccaggccct cttggcacag ctgtgggctc   3318
cttggcacat gaggccggct ctccccactg gctgggtct aaccttgaac cctcaccacg    3378
tgcaggtcac acacagtgaa gccacttgta actgcacact tttctgtgga aacatcttca   3438
ccctttacca ggcttggcat ggtctgaact ggaaaccctg agaatgtttc tgcagtagga   3498
caggagggac atcttcccat gccttcccta aaccggagg ccccggactt ctctggaaaa    3558
ccgcctgtct gcaggcccga ttcaaatcta tgggggctgc acttcccttt tacatttga    3618 tgtgtcaaag gcttttggag tgaccaaaag cacagaggca gcgggtgggg cgcctgggtg   3678
gtccccaagg tcgctgccac ccttgccggg ggcagaggca taagcccaca tatgctgtga   3738
cgctggccac ctttctcag cttctgaggc tgcgatgcct caggaactcc agtttacaga    3798
gaccagtgtg tttacttgta ataaagcct ctggtggtg gagacggtac tttcagtggg     3858
tctgtgcccc gtggcccctg tgcctgttcg gtggggtgt cccagagaag cctggcacca    3918 gtaccccgt caa                                                      3931
```

<210> SEQ ID NO 2
<211> LENGTH: 1004
<212> TYPE: PRT
<213> ORGANISM: Homo sapiens

<400> SEQUENCE: 2

```
Met Gly Glu Leu Cys Arg Arg Asp Ser Ala Leu Thr Ala Leu Asp Glu
1               5                   10                  15

Glu Thr Leu Trp Glu Met Met Glu Ser His Arg His Arg Ile Val Arg
            20                  25                  30

Cys Ile Cys Pro Ser Arg Leu Thr Pro Tyr Leu Arg Gln Ala Lys Val
        35                  40                  45

Leu Cys Gln Leu Asp Glu Glu Glu Val Leu His Ser Pro Arg Leu Thr
    50                  55                  60

Asn Ser Ala Met Arg Ala Gly His Leu Leu Asp Leu Leu Lys Thr Arg
65                  70                  75                  80

Gly Lys Asn Gly Ala Ile Ala Phe Leu Glu Ser Leu Lys Phe His Asn
                85                  90                  95

Pro Asp Val Tyr Thr Leu Val Thr Gly Leu Gln Pro Asp Val Asp Phe
            100                 105                 110

Ser Asn Phe Ser Gly Leu Met Glu Thr Ser Lys Leu Thr Glu Cys Leu
        115                 120                 125

Ala Gly Ala Ile Gly Ser Leu Gln Glu Glu Leu Asn Gln Glu Lys Gly
    130                 135                 140

Gln Lys Glu Val Leu Leu Arg Arg Cys Gln Gln Leu Gln Glu His Leu
145                 150                 155                 160

Gly Leu Ala Glu Thr Arg Ala Glu Gly Leu His Gln Leu Glu Ala Asp
```

```
                  165                 170                 175
His Ser Arg Met Lys Arg Glu Val Ser Ala His Phe His Glu Val Leu
            180                 185                 190
Arg Leu Lys Asp Glu Met Leu Ser Leu Ser Leu His Tyr Ser Asn Ala
        195                 200                 205
Leu Gln Glu Lys Glu Leu Ala Ala Ser Arg Cys Arg Ser Leu Gln Glu
    210                 215                 220
Glu Leu Tyr Leu Leu Lys Gln Glu Leu Gln Arg Ala Asn Met Val Ser
225                 230                 235                 240
Ser Cys Glu Leu Glu Leu Gln Glu Gln Ser Leu Arg Thr Ala Ser Asp
                245                 250                 255
Gln Glu Ser Gly Asp Glu Leu Asn Arg Leu Lys Glu Asn Glu
            260                 265                 270
Lys Leu Arg Ser Leu Thr Phe Ser Leu Ala Glu Lys Asp Ile Leu Glu
        275                 280                 285
Gln Ser Leu Asp Glu Ala Arg Gly Ser Arg Gln Glu Leu Val Glu Arg
    290                 295                 300
Ile His Ser Leu Arg Glu Arg Ala Val Ala Ala Glu Arg Gln Arg Glu
305                 310                 315                 320
Gln Tyr Trp Glu Glu Lys Glu Gln Thr Leu Leu Gln Phe Gln Lys Ser
                325                 330                 335
Lys Met Ala Cys Gln Leu Tyr Arg Glu Lys Val Asn Ala Leu Gln Ala
            340                 345                 350
Gln Val Cys Glu Leu Gln Lys Glu Arg Asp Gln Ala Tyr Ser Ala Arg
        355                 360                 365
Asp Ser Ala Gln Arg Glu Ile Ser Gln Ser Leu Val Glu Lys Asp Ser
    370                 375                 380
Leu Arg Arg Gln Val Phe Glu Leu Thr Asp Gln Val Cys Glu Leu Arg
385                 390                 395                 400
Thr Gln Leu Arg Gln Leu Gln Ala Glu Pro Pro Gly Val Leu Lys Gln
                405                 410                 415
Glu Ala Arg Thr Arg Glu Pro Cys Pro Arg Glu Lys Gln Arg Leu Val
            420                 425                 430
Arg Met His Ala Ile Cys Pro Arg Asp Asp Ser Asp Cys Ser Leu Val
        435                 440                 445
Ser Ser Thr Glu Ser Gln Leu Leu Ser Asp Leu Ser Ala Thr Ser Ser
    450                 455                 460
Arg Glu Leu Val Asp Ser Phe Arg Ser Ser Pro Ala Pro Pro Ser
465                 470                 475                 480
Gln Gln Ser Leu Tyr Lys Arg Val Ala Glu Asp Phe Gly Glu Pro
                485                 490                 495
Trp Ser Phe Ser Ser Cys Leu Glu Ile Pro Glu Gly Asp Pro Gly Ala
            500                 505                 510
Leu Pro Gly Ala Lys Ala Gly Asp Pro His Leu Asp Tyr Glu Leu Leu
        515                 520                 525
Asp Thr Ala Asp Leu Pro Gln Leu Glu Ser Ser Leu Gln Pro Val Ser
    530                 535                 540
Pro Gly Arg Leu Asp Val Ser Glu Ser Gly Val Leu Met Arg Arg
545                 550                 555                 560
Pro Ala Arg Arg Ile Leu Ser Gln Val Thr Met Leu Ala Phe Gln Gly
                565                 570                 575
Asp Ala Leu Leu Glu Gln Ile Ser Val Ile Gly Gly Asn Leu Thr Gly
            580                 585                 590
```

-continued

```
Ile Phe Ile His Arg Val Thr Pro Gly Ser Ala Ala Asp Gln Met Ala
            595                 600                 605

Leu Arg Pro Gly Thr Gln Ile Val Met Val Asp Tyr Glu Ala Ser Glu
            610                 615                 620

Pro Leu Phe Lys Ala Val Leu Glu Asp Thr Thr Leu Glu Glu Ala Val
625                 630                 635                 640

Gly Leu Leu Arg Arg Val Asp Gly Phe Cys Cys Leu Ser Val Lys Val
                    645                 650                 655

Asn Thr Asp Gly Tyr Lys Arg Leu Leu Gln Asp Leu Glu Ala Lys Val
            660                 665                 670

Ala Thr Ser Gly Asp Ser Phe Tyr Ile Arg Val Asn Leu Ala Met Glu
            675                 680                 685

Gly Arg Ala Lys Gly Glu Leu Gln Val His Cys Asn Glu Val Leu His
            690                 695                 700

Val Thr Asp Thr Met Phe Gln Gly Cys Gly Cys Trp His Ala His Arg
705                 710                 715                 720

Val Asn Ser Tyr Thr Met Lys Asp Thr Ala Ala His Gly Thr Ile Pro
                    725                 730                 735

Asn Tyr Ser Arg Ala Gln Gln Leu Ile Ala Leu Ile Gln Asp Met
            740                 745                 750

Thr Gln Gln Cys Thr Val Thr Arg Lys Pro Ser Ser Gly Gly Pro Gln
            755                 760                 765

Lys Leu Val Arg Ile Val Ser Met Asp Lys Ala Lys Ala Ser Pro Leu
            770                 775                 780

Arg Leu Ser Phe Asp Arg Gly Gln Leu Asp Pro Ser Arg Met Glu Gly
785                 790                 795                 800

Ser Ser Thr Cys Phe Trp Ala Glu Ser Cys Leu Thr Leu Val Pro Tyr
                    805                 810                 815

Thr Leu Val Trp Pro His Arg Pro Ala Arg Pro Arg Pro Val Leu Leu
            820                 825                 830

Val Pro Arg Ala Val Gly Lys Ile Leu Ser Glu Lys Leu Cys Leu Leu
            835                 840                 845

Gln Gly Phe Lys Lys Cys Leu Ala Glu Tyr Leu Ser Gln Glu Glu Tyr
            850                 855                 860

Glu Ala Trp Ser Gln Arg Gly Asp Ile Ile Gln Glu Gly Glu Val Ser
865                 870                 875                 880

Gly Gly Arg Cys Trp Val Thr Arg His Ala Val Glu Ser Leu Met Glu
                    885                 890                 895

Lys Asn Thr His Ala Leu Leu Asp Val Gln Leu Asp Ser Val Cys Thr
            900                 905                 910

Leu His Arg Met Asp Ile Phe Pro Ile Val Ile His Val Ser Val Asn
            915                 920                 925

Glu Lys Met Ala Lys Lys Leu Lys Lys Gly Leu Gln Arg Leu Gly Thr
            930                 935                 940

Ser Glu Glu Gln Leu Leu Glu Ala Ala Arg Gln Glu Glu Gly Asp Leu
945                 950                 955                 960

Asp Arg Ala Pro Cys Leu Tyr Ser Ser Leu Ala Pro Asp Gly Trp Ser
                    965                 970                 975

Asp Leu Asp Gly Leu Leu Ser Cys Val Arg Gln Ala Ile Ala Asp Glu
            980                 985                 990

Gln Lys Lys Val Val Trp Thr Glu Gln Ser Pro Arg
            995                 1000
```

-continued

```
<210> SEQ ID NO 3
<211> LENGTH: 3012
<212> TYPE: DNA
<213> ORGANISM: Homo sapiens

<400> SEQUENCE: 3
atgggggaac tgtgccgcag ggactccgca ctcacggcac tggacgagga gacactgtgg      60
gagatgatgg agagccaccg ccacaggatc gtacgctgca tctgcccag  ccgcctcacc     120 ccctacctgc gccaggccaa ggtgctgtgc cagctggacg aggaggagt  gctgcacagc     180 ccccggctca ccaacagcgc catgcgggcc ggcacttgc  tggatttgct gaagactcga     240
gggaagaacg gggccatcgc cttcctggag agcctgaagt tccacaaccc tgacgtctac     300
accctggtca ccgggctgca gcctgatgtt gacttcagta actttagcgg tctcatggag     360
acatccaagc tgaccgagtg cctggctggg gccatcggca gcctgcagga ggagctgaac     420
caggaaaagg gcagaagga  ggtgctgctg cggcggtgcc agcagctgca ggagcacctg     480
ggcctggccg agacccgtgc cgagggcctg caccagctgg aggctgacca gccgcatg      540 aagcgtgagg ttagcgcaca cttccatgag gtgctgaggc tgaaggacga gatgctcagc     600
ctctcgctgc actatagcaa tgcgctgcag gagaaggagc tggccgcctc acgctgccgc     660
agcctgcagg aggagctgta tctactgaag caggagctgc agcgagccaa catggtttcc     720
tcctgtgagc tggaattgca agagcagtcc ctgaggacag ccagcgacca ggagtccggg     780
gatgaggagc tgaaccgcct gaaggaggag aatgagaaac tgcgctcgct gactttcagc     840
ctggcggaga aggacattct ggagcagagc ctggacgagg cgcgggggag ccgacaggag     900
ctggtggagc gcatccactc gctgcgggag cgggccgtgg ctgccgagag cagcgagag     960 cagtactggg aagagaagga acagaccctg ctgcagttcc agaagagtaa gatggcctgc    1020
caactctaca gggagaaggt gaatgcgctg caggcccagg tgtgcgagct gcagaaggag    1080
cgagaccagg cgtactccgc gagggacagt gctcagaggg agatttccca gagcctggtg    1140
gagaaggact ccctccgcag gcaggtgttc gagctgacgg accaggtctg cgagctgcgc    1200
acacagcttc gccagctgca ggcagagcct ccgggtgtgc tcaagcagga agccaggacc    1260
agggagccct gtccacggga gaagcagcgg ctggtgcgga tgcatgccat ctgccccaga    1320
gacgacagcg actgcagcct cgtcagctcc acagagtctc agctcttgtc ggacctgagt    1380
gccacgtcca gccgcgagct ggtggacagc ttccgctcca gcagccccgc gcccccagc    1440 cagcagtccc tgtacaagcg ggtggccgag gacttcgggg aagaaccctg gtctttcagc    1500
agctgcctgg agatcccgga gggagacccg ggagccctgc cgggagctaa ggcaggcgac    1560
ccacacctgg attatgagct cctagacacg gcagaccttc gcagctgga  aagcagcctg    1620 cagccagtct cccctggaag gcttgatgtc tcggagagcg gcgtcctcat gcggcggagg    1680
ccagcccgca ggatcctgag ccaggtcacc atgctggcgt tccaggggga tgcattgctg    1740
gagcagatca gcgtcatcgg cgggaacctc acgggcatct tcatccaccg ggtcaccccg    1800
ggctcggcgg cggaccagat ggccttgcgc ccgggcaccc agattgtgat ggttgattac    1860
gaagcctcag agcccttgtt caaggcagtc ctggaggaca cgaccctgga ggaggccgtg    1920
gggcttctca ggagggtgga cggcttctgc tgcctgtctg tgaaggtcaa cacggacggt    1980
tataagaggc tactccagga cctggaggcc aaagtggcga cctcggggga ctcattctac    2040
atccgggtca acctggccat ggagggcagg gccaaagggg agctgcaggt gcattgcaac    2100
gaggtcctgc acgtcaccga caccatgttc cagggctgcg gctgctggca tgcccaccgc    2160
```

-continued

```
gtgaactctt acaccatgaa ggatactgcc gcgcacggca ccatcccaa ctactccagg      2220 gctcagcagc agctcatagc cctcatccag gacatgactc agcagtgcac cgtgacccgc      2280
aagccatctt ctgggggacc acagaagctg gtccgcatcg tcagtatgga caaagccaag      2340
gccagccctc tgcgtttgtc ctttgacagg ggccagttgg accccagcag gatggagggc      2400
tccagcacgt gcttctgggc cgagagctgc ctcaccctgg tgccctatac cctggtgtgg      2460
ccccatcgac ccgcccggcc ccggcctgtg ctcctcgtgc ccagggcggt tgggaagatc      2520
ctgagcgaga aactgtgcct cctccaaggg tttaagaagt gcctggcaga gtacttgagc      2580
caggaggagt atgaggcctg gagccagaga ggggacatca tccaggaggg agaggtgtcc      2640
gggggccgct gctgggtgac cgccatgct gtggagtccc tcatggaaaa gaacacccat      2700
gccctcctgg acgtccagct ggacagtgtc tgcaccctgc acaggatgga catcttcccc      2760
atcgtcatcc acgtctctgt caacgagaag atggcaaaga agctcaagaa gggcctacag      2820
cggttgggca cctcagagga gcagctcctg gaggctgcga ggcaggagga gggagacctg      2880
gaccgggcgc cctgtctata cagcagcctg gctcctgacg gctggagcga cctggacggc      2940
ctgctcagct gtgtccgcca ggccatcgcc gacgagcaga agaaggtggt gtggacggag      3000
cagagccccc ga                                                          3012
```

```
<210> SEQ ID NO 4
<211> LENGTH: 3417
<212> TYPE: DNA
<213> ORGANISM: Homo sapiens
<220> FEATURE:
<221> NAME/KEY: CDS
<222> LOCATION: (1)...(3417)

<400> SEQUENCE: 4
```

```
atg ggg gaa ctg tgc cgc agg gac tcc gca ctc acg gca ctg gac gag       48
Met Gly Glu Leu Cys Arg Arg Asp Ser Ala Leu Thr Ala Leu Asp Glu
 1               5                  10                  15 gag aca ctg tgg gag atg atg gag agc cac cgc cac agg atc gta cgc       96
Glu Thr Leu Trp Glu Met Met Glu Ser His Arg His Arg Ile Val Arg
             20                  25                  30 tgc atc tgc ccc agc cgc ctc acc ccc tac ctg cgc cag gcc aag gtg      144
Cys Ile Cys Pro Ser Arg Leu Thr Pro Tyr Leu Arg Gln Ala Lys Val
         35                  40                  45 ctg tgc cag ctg gac gag gag gag gtg ctg cac agc ccc cgg ctc acc      192
Leu Cys Gln Leu Asp Glu Glu Glu Val Leu His Ser Pro Arg Leu Thr
     50                  55                  60 aac agc gcc atg cgg gcc ggg cac ttg ctg gat ttg ctg aag act cga      240
Asn Ser Ala Met Arg Ala Gly His Leu Leu Asp Leu Leu Lys Thr Arg
 65                  70                  75                  80 ggg aag aac ggg gcc atc gcc ttc ctg gag agc ctg aag ttc cac aac      288
Gly Lys Asn Gly Ala Ile Ala Phe Leu Glu Ser Leu Lys Phe His Asn
                 85                  90                  95 cct gac gtc tac acc ctg gtc acc ggg ctg cag cct gat gtt gac ttc      336
Pro Asp Val Tyr Thr Leu Val Thr Gly Leu Gln Pro Asp Val Asp Phe
            100                 105                 110 agt aac ttt agc ggt gag agc tcc gac ttt gac ggt ttg gca ggc act      384
Ser Asn Phe Ser Gly Glu Ser Ser Asp Phe Asp Gly Leu Ala Gly Thr
        115                 120                 125 tct agg aac ctc agg ctc ctg gta acc cca ggt ctc atg gag aca tcc      432
Ser Arg Asn Leu Arg Leu Leu Val Thr Pro Gly Leu Met Glu Thr Ser
    130                 135                 140 aag ctg acc gag tgc ctg gct ggg gcc atc ggc agc ctg cag gag gag      480
```

-continued

```
Lys Leu Thr Glu Cys Leu Ala Gly Ala Ile Gly Ser Leu Gln Glu Glu
145                 150                 155                 160 ctg aac cag gaa aag ggg cag aag gag gtg ctg ctg cgg cgg tgc cag        528
Leu Asn Gln Glu Lys Gly Gln Lys Glu Val Leu Leu Arg Arg Cys Gln
                165                 170                 175 cag ctg cag gag cac ctg ggc ctg gcc gag acc cgt gcc gag ggc ctg        576
Gln Leu Gln Glu His Leu Gly Leu Ala Glu Thr Arg Ala Glu Gly Leu
            180                 185                 190 cac cag ctg gag gct gac cac agc cgc atg aag cgt gag gtt agc gca        624
His Gln Leu Glu Ala Asp His Ser Arg Met Lys Arg Glu Val Ser Ala
        195                 200                 205 cac ttc cat gag gtg ctg agg ctg aag gac gag atg ctc agc ctc tcg        672
His Phe His Glu Val Leu Arg Leu Lys Asp Glu Met Leu Ser Leu Ser
    210                 215                 220 ctg cac tat agc aat gcg ctg cag gag aag gag ctg gcc gcc tca cgc        720
Leu His Tyr Ser Asn Ala Leu Gln Glu Lys Glu Leu Ala Ala Ser Arg
225                 230                 235                 240 tgc cgc agc ctg cag gag gag ctg tat cta ctg aag cag gag ctg cag        768
Cys Arg Ser Leu Gln Glu Glu Leu Tyr Leu Leu Lys Gln Glu Leu Gln
                245                 250                 255 cga gcc aac atg gtt tcc tcc tgt gag ctg gaa ttg caa gag cag tcc        816
Arg Ala Asn Met Val Ser Ser Cys Glu Leu Glu Leu Gln Glu Gln Ser
            260                 265                 270 ctg agg aca gcc agc gac cag gag tcc ggg gat gag gag ctg aac cgc        864
Leu Arg Thr Ala Ser Asp Gln Glu Ser Gly Asp Glu Glu Leu Asn Arg
        275                 280                 285 ctg aag gag gag aat gag aaa ctg cgc tcg ctg act ttc agc ctg gcg        912
Leu Lys Glu Glu Asn Glu Lys Leu Arg Ser Leu Thr Phe Ser Leu Ala
    290                 295                 300 gag aag gac att ctg gag cag agc ctg gac gag gcg cgg ggg agc cga        960
Glu Lys Asp Ile Leu Glu Gln Ser Leu Asp Glu Ala Arg Gly Ser Arg
305                 310                 315                 320 cag gag ctg gtg gag cgc atc cac tcg ctg cgg gag cgg gcc gtg gct       1008
Gln Glu Leu Val Glu Arg Ile His Ser Leu Arg Glu Arg Ala Val Ala
                325                 330                 335 gcc gag agg cag cga gag cag gcc aga ccc tca gag ctg ctg agc ttc       1056
Ala Glu Arg Gln Arg Glu Gln Ala Arg Pro Ser Glu Leu Leu Ser Phe
            340                 345                 350 acg gtc cat gtg tcc cac tct gtc cag tac tgg gaa gag aag gaa cag       1104
Thr Val His Val Ser His Ser Val Gln Tyr Trp Glu Glu Lys Glu Gln
        355                 360                 365 acc ctg ctg cag ttc cag aag agt aag atg gcc tgc caa ctc tac agg       1152
Thr Leu Leu Gln Phe Gln Lys Ser Lys Met Ala Cys Gln Leu Tyr Arg
    370                 375                 380 gag aag gtg aat gcg ctg cag gcc cag gtg tgc gag ctg cag aag gag       1200
Glu Lys Val Asn Ala Leu Gln Ala Gln Val Cys Glu Leu Gln Lys Glu
385                 390                 395                 400 cga gac cag gcg tac tcc gcg agg gac agt gct cag agg gag att tcc       1248
Arg Asp Gln Ala Tyr Ser Ala Arg Asp Ser Ala Gln Arg Glu Ile Ser
                405                 410                 415 cag agc ctg gtg gag aag gac tcc ctc cgc agg cag gtg ttc gag ctg       1296
Gln Ser Leu Val Glu Lys Asp Ser Leu Arg Arg Gln Val Phe Glu Leu
            420                 425                 430 acg gac cag gtc tgc gag ctg cgc aca cag ctt cgc cag ctg cag gca       1344
Thr Asp Gln Val Cys Glu Leu Arg Thr Gln Leu Arg Gln Leu Gln Ala
        435                 440                 445 gag cct ccg ggt gtg ctc aag cag gaa gcc agg acc agg gag ccc tgt       1392
Glu Pro Pro Gly Val Leu Lys Gln Glu Ala Arg Thr Arg Glu Pro Cys
    450                 455                 460
```

-continued

| | | |
|---|---|---|
| cca cgg gag aag cag cgg ctg gtg cgg atg cat gcc atc tgc ccc aga<br>Pro Arg Glu Lys Gln Arg Leu Val Arg Met His Ala Ile Cys Pro Arg<br>465                            470                          475                          480 | 1440 |
| gac gac agc gac tgc agc ctc gtc agc tcc aca gag tct cag ctc ttg<br>Asp Asp Ser Asp Cys Ser Leu Val Ser Ser Thr Glu Ser Gln Leu Leu<br>                      485                          490                          495 | 1488 |
| tcg gac ctg agt gcc acg tcc agc cgc gag ctg gtg gac agc ttc cgc<br>Ser Asp Leu Ser Ala Thr Ser Ser Arg Glu Leu Val Asp Ser Phe Arg<br>            500                        505                          510 | 1536 |
| tcc agc agc ccc gcg ccc ccc agc cag cag tcc ctg tac aag cgg gtg<br>Ser Ser Ser Pro Ala Pro Pro Ser Gln Gln Ser Leu Tyr Lys Arg Val<br>                515                      520                        525 | 1584 |
| gcc gag gac ttc ggg gaa gaa ccc tgg tct ttc agc agc tgc ctg gag<br>Ala Glu Asp Phe Gly Glu Glu Pro Trp Ser Phe Ser Ser Cys Leu Glu<br>530                            535                          540 | 1632 |
| atc ccg gag gga gac ccg gga gcc ctg ccg gga gct aag gca ggc gac<br>Ile Pro Glu Gly Asp Pro Gly Ala Leu Pro Gly Ala Lys Ala Gly Asp<br>545                            550                          555                        560 | 1680 |
| cca cac ctg gat tat gag ctc cta gac acg gca gac ctt ccg cag ctg<br>Pro His Leu Asp Tyr Glu Leu Leu Asp Thr Ala Asp Leu Pro Gln Leu<br>                      565                          570                          575 | 1728 |
| gaa agc agc ctg cag cca gtc tcc cct gga agg ctt gat gtc tcg gag<br>Glu Ser Ser Leu Gln Pro Val Ser Pro Gly Arg Leu Asp Val Ser Glu<br>            580                        585                          590 | 1776 |
| agt gca caa gcc ggt cgt ctc ccg gcc tgc agc ggc gtc ctc atg cgg<br>Ser Ala Gln Ala Gly Arg Leu Pro Ala Cys Ser Gly Val Leu Met Arg<br>                595                      600                        605 | 1824 |
| cgg agg cca gcc cgc agg atc ctg agc cag gtc acc atg ctg gcg ttc<br>Arg Arg Pro Ala Arg Arg Ile Leu Ser Gln Val Thr Met Leu Ala Phe<br>610                            615                          620 | 1872 |
| cag ggg gat gca ttg ctg gag cag atc agc gtc atc ggc ggg aac ctc<br>Gln Gly Asp Ala Leu Leu Glu Gln Ile Ser Val Ile Gly Gly Asn Leu<br>625                            630                          635                        640 | 1920 |
| acg ggc atc ttc atc cac cgg gtc acc ccg ggc tcg gcg gcg gac cag<br>Thr Gly Ile Phe Ile His Arg Val Thr Pro Gly Ser Ala Ala Asp Gln<br>                      645                          650                          655 | 1968 |
| atg gcc ttg cgc ccg ggc acc cag att gtg atg gtt gat tac gaa gcc<br>Met Ala Leu Arg Pro Gly Thr Gln Ile Val Met Val Asp Tyr Glu Ala<br>660                            665                          670 | 2016 |
| tca gag ccc ttg ttc aag gca gtc ctg gag gac acg acc ctg gag gag<br>Ser Glu Pro Leu Phe Lys Ala Val Leu Glu Asp Thr Thr Leu Glu Glu<br>            675                        680                          685 | 2064 |
| gcc gtg ggg ctt ctc agg agg gtg gac ggc ttc tgc tgc ctg tct gtg<br>Ala Val Gly Leu Leu Arg Arg Val Asp Gly Phe Cys Cys Leu Ser Val<br>690                            695                          700 | 2112 |
| aag gtc aac acg gac ggt tat aag agg cta ctc cag gac ctg gag gcc<br>Lys Val Asn Thr Asp Gly Tyr Lys Arg Leu Leu Gln Asp Leu Glu Ala<br>705                            710                          715                        720 | 2160 |
| aaa gtg gcg acc tcg ggg gac tca ttc tac atc cgg gtc aac ctg gcc<br>Lys Val Ala Thr Ser Gly Asp Ser Phe Tyr Ile Arg Val Asn Leu Ala<br>                      725                          730                          735 | 2208 |
| atg gag ggc agg gcc aaa ggg gag ctg cag gtg cat tgc aac gag gtc<br>Met Glu Gly Arg Ala Lys Gly Glu Leu Gln Val His Cys Asn Glu Val<br>            740                        745                          750 | 2256 |
| ctg cac gtc acc gac acc atg ttc cag ggc tgc ggc tgc tgg cat gcc<br>Leu His Val Thr Asp Thr Met Phe Gln Gly Cys Gly Cys Trp His Ala<br>                755                      760                        765 | 2304 |
| cac cgc gtg aac tct tac acc atg aag gat act gcc gcg cac ggc acc<br>His Arg Val Asn Ser Tyr Thr Met Lys Asp Thr Ala Ala His Gly Thr<br>770                            775                          780 | 2352 |

```
                                              -continued atc ccc aac tac tcc agg gct cag cag cag ctc ata gcc ctc atc cag    2400
Ile Pro Asn Tyr Ser Arg Ala Gln Gln Gln Leu Ile Ala Leu Ile Gln
785             790                 795                 800 gac atg act cag cag tgc acc gtg acc cgc aag cca tct tct ggg gga    2448
Asp Met Thr Gln Gln Cys Thr Val Thr Arg Lys Pro Ser Ser Gly Gly
                805                 810                 815 cca cag aag ctg gtc cgc atc gtc agt atg gac aaa gcc aag gcc agc    2496
Pro Gln Lys Leu Val Arg Ile Val Ser Met Asp Lys Ala Lys Ala Ser
            820                 825                 830 cct ctg cgt ttg tcc ttt gac agg ggc cag ttg gac ccc agc agg atg    2544
Pro Leu Arg Leu Ser Phe Asp Arg Gly Gln Leu Asp Pro Ser Arg Met
        835                 840                 845 gag ggc tcc agc acg tgc ttc tgg gcc gag agc tgc ctc acc ctg gtg    2592
Glu Gly Ser Ser Thr Cys Phe Trp Ala Glu Ser Cys Leu Thr Leu Val
    850                 855                 860 ccc tat acc ctg gtg cgg ccc cat cga ccc gcc cgg ccc cgg cct gtg    2640
Pro Tyr Thr Leu Val Arg Pro His Arg Pro Ala Arg Pro Arg Pro Val
865                 870                 875                 880 ctc ctc gtg ccc agg gcg gtt ggg aag atc ctg agc gag aaa ctg tgc    2688
Leu Leu Val Pro Arg Ala Val Gly Lys Ile Leu Ser Glu Lys Leu Cys
                885                 890                 895 ctc ctc caa ggg ttt aag aag tgc ctg gca gag tac ttg agc cag gag    2736
Leu Leu Gln Gly Phe Lys Lys Cys Leu Ala Glu Tyr Leu Ser Gln Glu
            900                 905                 910 gag tat gag gcc tgg agc cag aga ggg gac atc atc cag gag gga gag    2784
Glu Tyr Glu Ala Trp Ser Gln Arg Gly Asp Ile Ile Gln Glu Gly Glu
        915                 920                 925 gtg tcc ggg ggc cgc tgc tgg gtg acc cgc cat gct gtg gag tcc ctc    2832
Val Ser Gly Gly Arg Cys Trp Val Thr Arg His Ala Val Glu Ser Leu
    930                 935                 940 atg gaa aag aac acc cat gcc ctc ctg gac gtc cag ctg gac agt gtc    2880
Met Glu Lys Asn Thr His Ala Leu Leu Asp Val Gln Leu Asp Ser Val
945                 950                 955                 960 tgc acc ctg cac agg atg gac atc ttc ccc atc gtc atc cac gtc tct    2928
Cys Thr Leu His Arg Met Asp Ile Phe Pro Ile Val Ile His Val Ser
                965                 970                 975 gtc aac gag aag atg gca aag aag ctc aag aag gga cta cag cgg ttg    2976
Val Asn Glu Lys Met Ala Lys Lys Leu Lys Lys Gly Leu Gln Arg Leu
            980                 985                 990 ggc acc tca gag gag cag ctc ctg gag gct gcg agg cag gag gag gga    3024
Gly Thr Ser Glu Glu Gln Leu Leu Glu Ala Ala Arg Gln Glu Glu Gly
        995                 1000                1005 gac ctg gac cgg gcg ccc tgt cta tac agc agc ctg gct cct gac ggc    3072
Asp Leu Asp Arg Ala Pro Cys Leu Tyr Ser Ser Leu Ala Pro Asp Gly
    1010                1015                1020 tgg agc gac ctg gac ggc ctg ctc agc tgt gtc cgc cag gcc atc gcc    3120
Trp Ser Asp Leu Asp Gly Leu Leu Ser Cys Val Arg Gln Ala Ile Ala
1025                1030                1035                1040 gac gag cag aag aag gtg caa cgc cga cgt cat cca aga att aac cca    3168
Asp Glu Gln Lys Lys Val Gln Arg Arg Arg His Pro Arg Ile Asn Pro
                1045                1050                1055 agc cag agg acg ggc atc gcc acc cag caa cgc cag tgt cac cga aga    3216
Ser Gln Arg Thr Gly Ile Ala Thr Gln Gln Arg Gln Cys His Arg Arg
            1060                1065                1070 att aac cca agg cag agg atg ggc att gcc acc cag caa cgc cag tgt    3264
Ile Asn Pro Arg Gln Arg Met Gly Ile Ala Thr Gln Gln Arg Gln Cys
        1075                1080                1085 cac cga aga att aac cca agc cag agg acg ggc atc acc acc cag caa    3312
His Arg Arg Ile Asn Pro Ser Gln Arg Thr Gly Ile Thr Thr Gln Gln
```

```
                1090              1095              1100
tgc cag tgt cac cga aga att aac cca agc cag agg acg ggc atc gcc    3360
Cys Gln Cys His Arg Arg Ile Asn Pro Ser Gln Arg Thr Gly Ile Ala
1105              1110              1115              1120 atg cct tca tct tcg gac act ctc aaa aaa gat aag ctt ctg ccc aga    3408
Met Pro Ser Ser Ser Asp Thr Leu Lys Lys Asp Lys Leu Leu Pro Arg
              1125              1130              1135 aac acc aca                                                        3417
Asn Thr Thr <210> SEQ ID NO 5
<211> LENGTH: 1138
<212> TYPE: PRT
<213> ORGANISM: Homo sapiens

<400> SEQUENCE: 5
```

| | | | | | | | | | | | | | | | |
|---|---|---|---|---|---|---|---|---|---|---|---|---|---|---|---|
| Gly | Glu | Leu | Cys | Arg | Arg | Asp | Ser | Ala | Leu | Thr | Ala | Leu | Asp | Glu | Glu |
| 1 | | | | 5 | | | | | 10 | | | | | 15 | |
| Thr | Leu | Trp | Glu | Met | Met | Glu | Ser | His | Arg | His | Arg | Ile | Val | Arg | Cys |
| | | | 20 | | | | | 25 | | | | | 30 | | |
| Ile | Cys | Pro | Ser | Arg | Leu | Thr | Pro | Tyr | Leu | Arg | Gln | Ala | Lys | Val | Leu |
| | | 35 | | | | | 40 | | | | | 45 | | | |
| Cys | Gln | Leu | Asp | Glu | Glu | Val | Leu | His | Ser | Pro | Arg | Leu | Thr | Asn |
| 50 | | | | | 55 | | | | | 60 | | | | | |
| Ser | Ala | Met | Arg | Ala | Gly | His | Leu | Leu | Asp | Leu | Leu | Lys | Thr | Arg | Gly |
| 65 | | | | 70 | | | | | 75 | | | | | 80 | |
| Lys | Asn | Gly | Ala | Ile | Ala | Phe | Leu | Glu | Ser | Leu | Lys | Phe | His | Asn | Pro |
| | | | | 85 | | | | | 90 | | | | | 95 | |
| Asp | Val | Tyr | Thr | Leu | Val | Thr | Gly | Leu | Gln | Pro | Asp | Val | Asp | Phe | Ser |
| | | | 100 | | | | | 105 | | | | | 110 | | |
| Asn | Phe | Ser | Gly | Glu | Ser | Ser | Asp | Phe | Asp | Gly | Leu | Ala | Gly | Thr | Ser |
| | | | 115 | | | | | 120 | | | | | 125 | | |
| Arg | Asn | Leu | Arg | Leu | Leu | Val | Thr | Pro | Gly | Leu | Met | Glu | Thr | Ser | Lys |
| | 130 | | | | | 135 | | | | | 140 | | | | |
| Leu | Thr | Glu | Cys | Leu | Ala | Gly | Ala | Ile | Gly | Ser | Leu | Gln | Glu | Glu | Leu |
| 145 | | | | | 150 | | | | | 155 | | | | | 160 |
| Asn | Gln | Glu | Lys | Gly | Gln | Lys | Glu | Val | Leu | Leu | Arg | Arg | Cys | Gln | Gln |
| | | | | 165 | | | | | 170 | | | | | 175 | |
| Leu | Gln | Glu | His | Leu | Gly | Leu | Ala | Glu | Thr | Arg | Ala | Glu | Gly | Leu | His |
| | | | 180 | | | | | 185 | | | | | 190 | | |
| Gln | Leu | Glu | Ala | Asp | His | Ser | Arg | Met | Lys | Arg | Glu | Val | Ser | Ala | His |
| | 195 | | | | | 200 | | | | | 205 | | | | |
| Phe | His | Glu | Val | Leu | Arg | Leu | Lys | Asp | Glu | Met | Leu | Ser | Leu | Ser | Leu |
| 210 | | | | | 215 | | | | | 220 | | | | | |
| His | Tyr | Ser | Asn | Ala | Leu | Gln | Glu | Lys | Glu | Leu | Ala | Ala | Ser | Arg | Cys |
| 225 | | | | | 230 | | | | | 235 | | | | | 240 |
| Arg | Ser | Leu | Gln | Glu | Glu | Leu | Tyr | Leu | Leu | Lys | Gln | Glu | Leu | Gln | Arg |
| | | | | 245 | | | | | 250 | | | | | 255 | |
| Ala | Asn | Met | Val | Ser | Ser | Cys | Glu | Leu | Glu | Leu | Gln | Glu | Gln | Ser | Leu |
| | | | 260 | | | | | 265 | | | | | 270 | | |
| Arg | Thr | Ala | Ser | Asp | Gln | Glu | Ser | Gly | Asp | Glu | Glu | Leu | Asn | Arg | Leu |
| | 275 | | | | | 280 | | | | | 285 | | | | |
| Lys | Glu | Glu | Asn | Glu | Lys | Leu | Arg | Ser | Leu | Thr | Phe | Ser | Leu | Ala | Glu |
| | 290 | | | | | 295 | | | | | 300 | | | | |
| Lys | Asp | Ile | Leu | Glu | Gln | Ser | Leu | Asp | Glu | Ala | Arg | Gly | Ser | Arg | Gln |

-continued

```
            305                 310                 315                 320
      Glu Leu Val Glu Arg Ile His Ser Leu Arg Glu Arg Ala Val Ala Ala
                      325                 330                 335
      Glu Arg Gln Arg Glu Gln Ala Arg Pro Ser Glu Leu Leu Ser Phe Thr
                      340                 345                 350
      Val His Val Ser His Ser Val Gln Tyr Trp Glu Glu Lys Glu Gln Thr
                      355                 360                 365
      Leu Leu Gln Phe Gln Lys Ser Lys Met Ala Cys Gln Leu Tyr Arg Glu
          370                 375                 380
      Lys Val Asn Ala Leu Gln Ala Gln Val Cys Glu Leu Gln Lys Glu Arg
      385                 390                 395                 400
      Asp Gln Ala Tyr Ser Ala Arg Asp Ser Ala Gln Arg Glu Ile Ser Gln
                      405                 410                 415
      Ser Leu Val Glu Lys Asp Ser Leu Arg Arg Gln Val Phe Glu Leu Thr
                      420                 425                 430
      Asp Gln Val Cys Glu Leu Arg Thr Gln Leu Arg Gln Leu Gln Ala Glu
                      435                 440                 445
      Pro Pro Gly Val Leu Lys Gln Glu Ala Arg Thr Arg Glu Pro Cys Pro
          450                 455                 460
      Arg Glu Lys Gln Arg Leu Val Arg Met His Ala Ile Cys Pro Arg Asp
      465                 470                 475                 480
      Asp Ser Asp Cys Ser Leu Val Ser Ser Thr Glu Ser Gln Leu Leu Ser
                      485                 490                 495
      Asp Leu Ser Ala Thr Ser Ser Arg Glu Leu Val Asp Ser Phe Arg Ser
                      500                 505                 510
      Ser Ser Pro Ala Pro Ser Gln Gln Ser Leu Tyr Lys Arg Val Ala
                      515                 520                 525
      Glu Asp Phe Gly Glu Pro Trp Ser Phe Ser Ser Cys Leu Glu Ile
          530                 535                 540
      Pro Glu Gly Asp Pro Gly Ala Leu Pro Gly Ala Lys Ala Gly Asp Pro
      545                 550                 555                 560
      His Leu Asp Tyr Glu Leu Leu Asp Thr Ala Asp Leu Pro Gln Leu Glu
                      565                 570                 575
      Ser Ser Leu Gln Pro Val Ser Pro Gly Arg Leu Asp Val Ser Glu Ser
                      580                 585                 590
      Ala Gln Ala Gly Arg Leu Pro Ala Cys Ser Gly Val Leu Met Arg Arg
                      595                 600                 605
      Arg Pro Ala Arg Arg Ile Leu Ser Gln Val Thr Met Leu Ala Phe Gln
          610                 615                 620
      Gly Asp Ala Leu Leu Glu Gln Ile Ser Val Ile Gly Gly Asn Leu Thr
      625                 630                 635                 640
      Gly Ile Phe Ile His Arg Val Thr Pro Gly Ser Ala Ala Asp Gln Met
                      645                 650                 655
      Ala Leu Arg Pro Gly Thr Gln Ile Val Met Val Asp Tyr Glu Ala Ser
                      660                 665                 670
      Glu Pro Leu Phe Lys Ala Val Leu Glu Asp Thr Thr Leu Glu Glu Ala
                      675                 680                 685
      Val Gly Leu Leu Arg Arg Val Asp Gly Phe Cys Cys Leu Ser Val Lys
          690                 695                 700
      Val Asn Thr Asp Gly Tyr Lys Arg Leu Leu Gln Asp Leu Glu Ala Lys
      705                 710                 715                 720
      Val Ala Thr Ser Gly Asp Ser Phe Tyr Ile Arg Val Asn Leu Ala Met
                      725                 730                 735
```

```
Glu Gly Arg Ala Lys Gly Glu Leu Gln Val His Cys Asn Glu Val Leu
            740                 745                 750

His Val Thr Asp Thr Met Phe Gln Gly Cys Gly Cys Trp His Ala His
            755                 760                 765

Arg Val Asn Ser Tyr Thr Met Lys Asp Thr Ala Ala His Gly Thr Ile
            770                 775                 780

Pro Asn Tyr Ser Arg Ala Gln Gln Leu Ile Ala Leu Ile Gln Asp
785                 790                 795                 800

Met Thr Gln Gln Cys Thr Val Thr Arg Lys Pro Ser Ser Gly Pro
                    805                 810                 815

Gln Lys Leu Val Arg Ile Val Ser Met Asp Lys Ala Lys Ala Ser Pro
            820                 825                 830

Leu Arg Leu Ser Phe Asp Arg Gly Gln Leu Asp Pro Ser Arg Met Glu
            835                 840                 845

Gly Ser Ser Thr Cys Phe Trp Ala Glu Ser Cys Leu Thr Leu Val Pro
            850                 855                 860

Tyr Thr Leu Val Arg Pro His Arg Pro Ala Arg Pro Arg Pro Val Leu
865                 870                 875                 880

Leu Val Pro Arg Ala Val Gly Lys Ile Leu Ser Glu Lys Leu Cys Leu
                    885                 890                 895

Leu Gln Gly Phe Lys Lys Cys Leu Ala Glu Tyr Leu Ser Gln Glu Glu
                    900                 905                 910

Tyr Glu Ala Trp Ser Gln Arg Gly Asp Ile Ile Gln Glu Gly Glu Val
                    915                 920                 925

Ser Gly Gly Arg Cys Trp Val Thr Arg His Ala Val Glu Ser Leu Met
            930                 935                 940

Glu Lys Asn Thr His Ala Leu Leu Asp Val Gln Leu Asp Ser Val Cys
945                 950                 955                 960

Thr Leu His Arg Met Asp Ile Phe Pro Ile Val Ile His Val Ser Val
                    965                 970                 975

Asn Glu Lys Met Ala Lys Lys Leu Lys Lys Gly Leu Gln Arg Leu Gly
                    980                 985                 990

Thr Ser Glu Glu Gln Leu Leu Glu Ala Ala Arg Gln Glu Glu Gly Asp
            995                 1000                1005

Leu Asp Arg Ala Pro Cys Leu Tyr Ser Ser Leu Ala Pro Asp Gly Trp
    1010                1015                1020

Ser Asp Leu Asp Gly Leu Leu Ser Cys Val Arg Gln Ala Ile Ala Asp
1025                1030                1035                1040

Glu Gln Lys Lys Val Gln Arg Arg His Pro Arg Ile Asn Pro Ser
            1045                1050                1055

Gln Arg Thr Gly Ile Ala Thr Gln Gln Arg Gln Cys His Arg Arg Ile
            1060                1065                1070

Asn Pro Arg Gln Arg Met Gly Ile Ala Thr Gln Arg Gln Cys His
    1075                1080                1085

Arg Arg Ile Asn Pro Ser Gln Arg Thr Gly Ile Thr Thr Gln Gln Cys
    1090                1095                1100

Gln Cys His Arg Arg Ile Asn Pro Ser Gln Arg Thr Gly Ile Ala Met
1105                1110                1115                1120

Pro Ser Ser Ser Asp Thr Leu Lys Lys Asp Lys Leu Leu Pro Arg Asn
            1125                1130                1135

Thr Thr
```

-continued

```
<210> SEQ ID NO 6
<211> LENGTH: 90
<212> TYPE: PRT
<213> ORGANISM: Artificial Sequence
<220> FEATURE:
<223> OTHER INFORMATION: consensus sequence

<400> SEQUENCE: 6

Ala Glu Asp Asp Arg Arg Leu Leu Arg Lys Asn Arg Leu Glu Leu Leu
 1               5                  10                  15

Gly Glu Leu Thr Leu Ser Gly Leu Leu Asp His Leu Leu Glu Lys Asn
             20                  25                  30

Val Leu Thr Glu Glu Glu Glu Lys Ile Lys Ala Lys Asn Thr Thr
         35                  40                  45

Arg Arg Asp Lys Ala Arg Glu Leu Ile Asp Ser Val Gln Lys Lys Gly
 50                  55                  60

Asn Gln Ala Phe Gly Ile Phe Leu Gln Ala Leu Arg Glu Thr Asp Gly
 65                  70                  75                  80

Glu Leu Leu Ala Asp Leu Leu Leu Asp Glu
                 85                  90

<210> SEQ ID NO 7
<211> LENGTH: 83
<212> TYPE: PRT
<213> ORGANISM: Artificial Sequence
<220> FEATURE:
<223> OTHER INFORMATION: consensus sequence

<400> SEQUENCE: 7

Glu Ile Thr Leu Glu Lys Glu Val Lys Arg Gly Gly Leu Gly Phe Ser
 1               5                  10                  15

Ile Lys Gly Gly Ser Asp Lys Gly Ile Val Val Ser Glu Val Leu Pro
             20                  25                  30

Gly Ser Gly Ala Ala Glu Ala Gly Gly Arg Leu Lys Glu Gly Asp Val
         35                  40                  45

Ile Leu Ser Val Asn Gly Gln Asp Val Glu Asn Met Ser His Glu Arg
 50                  55                  60

Ala Val Leu Ala Ile Lys Gly Ser Gly Gly Glu Val Thr Leu Thr Val
 65                  70                  75                  80

Leu Arg Asp

<210> SEQ ID NO 8
<211> LENGTH: 58
<212> TYPE: PRT
<213> ORGANISM: Artificial Sequence
<220> FEATURE:
<223> OTHER INFORMATION: consensus sequence

<400> SEQUENCE: 8

Glu Tyr Val Val Ala Leu Tyr Asp Tyr Glu Ala Gln Asn Glu Asp Glu
 1               5                  10                  15

Leu Ser Phe Lys Lys Gly Asp Ile Ile Thr Val Leu Glu Lys Ser Asp
             20                  25                  30

Asp Gly Trp Trp Glu Gly Glu Leu Asn Arg Thr Gly Lys Glu Gly Leu
         35                  40                  45

Phe Pro Ser Asn Tyr Val Glu Glu Ile Glu
 50                  55

<210> SEQ ID NO 9
<211> LENGTH: 108
```

```
<212> TYPE: PRT
<213> ORGANISM: Artificial Sequence
<220> FEATURE:
<223> OTHER INFORMATION: consensus sequence

<400> SEQUENCE: 9

Thr Arg Pro Val Pro Arg Pro Gly Glu Val Asp Gly Lys Asp Tyr His
1               5                   10                  15

Phe Val Ser Ser Arg Glu Glu Met Glu Lys Asp Ile Ala Ala Asn Glu
            20                  25                  30

Phe Leu Glu Tyr Gly Glu Phe Gln Gly Asn Tyr Tyr Gly Thr Ser Leu
                35                  40                  45

Glu Thr Val Arg Gln Val Ala Lys Gln Gly Lys Ile Cys Ile Leu Asp
        50                  55                  60

Val Glu Pro Gln Gly Val Lys Arg Leu Arg Thr Ala Glu Leu Ser Asn
65                  70                  75                  80

Pro Ile Val Val Phe Ile Ala Pro Pro Ser Leu Gln Glu Leu Glu Lys
                85                  90                  95

Arg Leu Glu Gly Arg Asn Lys Glu Ser Glu Glu Ser
                100                 105

<210> SEQ ID NO 10
<211> LENGTH: 105
<212> TYPE: PRT
<213> ORGANISM: Artificial Sequence
<220> FEATURE:
<223> OTHER INFORMATION: consensus sequence

<400> SEQUENCE: 10

Asp Ser Tyr Gln Lys Ser Ser Gly Asn Ser Ser Leu Trp Glu Ser Asn
1               5                   10                  15

Tyr Gln Asn Trp Gln Gln Glu Ala Ala Lys Leu Lys Ala Gln Ile Glu
            20                  25                  30

Asn Leu Gln Asn Asn Arg Asn Gln Arg His Leu Leu Gly Glu Asp Leu
            35                  40                  45

Gly Ser Leu Ser Leu Lys Glu Leu Gln Gln Leu Glu Gln Gln Leu Glu
        50                  55                  60

Lys Gly Leu Lys His Ile Arg Ser Arg Lys Asn Gln Leu Leu Leu Asp
65                  70                  75                  80

Gln Ile Glu Glu Leu Gln Lys Lys Glu Arg Glu Leu Gln Glu Glu Asn
                85                  90                  95

Lys Ala Leu Arg Lys Lys Ile Glu Glu
                100                 105
```

MOLECULES OF THE CARD-RELATED PROTEIN FAMILY AND USES THEREOF

RELATED APPLICATION INFORMATION

This application claims priority from provisional application Ser. No. 60/181,159, filed Feb. 9, 2000, the entire content of which is incorporated herein by reference.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppresser genes, can lead to an arrest of cellular proliferation.

A particular type of cell death called apoptosis occurs in differentiated cells when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as C. elegans, to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Apoptotic signaling is dependent on protein-protein interactions. At least three different protein-protein interaction domains, the death domain, the death effector domain and the caspase recruitment domain (CARD), have been identified within proteins involved in apoptosis. A fourth protein-protein interaction domain, the death recruiting domain (DRD) was recently identified in murine FLASH (Imai et al. (1999) *Nature* 398:777–85).

Many caspases and proteins that interact with caspases possess a CARD domain. Hofmann et al. ((1997) *TIBS* 22:155) and others have postulated that certain apoptotic proteins bind to each other via their CARD domains and that different subtypes of CARD domains may confer binding specificity, regulating the activity of various caspases, for example.

Nuclear factor-kB (NF-kB) is a transcription factor that is expressed in many cell types and activates genes that have NF-kB sites in their promoters. Molecules that regulate NF-kB activation play a critical role in both apoptosis and inflammation. Inactive NF-kB resides in the cytoplasm complexed with the regulatory protein IkB. NF-kB binding to IkB causes NF-kB to remain in the cytoplasm. NF-kB activating stimuli activate specific IkB kinases that phosphorylate IkB leading to its degradation. Once liberated from IkB, NF-kB translocates to the nucleus and activates genes that have NF-kB sites in their promoters.

At least two dozen stimuli that activate NF-kB are known, including cytokines, protein kinase C activators, oxidants, viruses, and immune system stimuli. NK-kB is stimulated via signaling through the tumor necrosis factor family receptors (TNFRs) and the interleukin-1/Toll receptor. Tumor necrosis factor family members bind to their cognate receptors, including Fas (CD95/APO-1), TRAMP (DR3/WSL-1/AIR/LARD), CD37, CD30, CD40, TNFR1 and TNFR2, and regulate apoptosis, cell proliferation, and proinflammatory responses. For example, the proinflammatory cytokines TNF-a and IL-1 induce NF-kB activation by binding their cell-surface receptors and activating the NF-kB-inducing kinase, NIK. In the case of TNF-a, binding to TNF-R1 induces aggregation of its death domain and assembly of a signaling complex containing TRADD, TRAF2, and RIP. Binding of IL-1 to its receptor, IL-1R, induces aggregation of the receptor and assembly of a signaling complex which includes AcP, MyD88, IRAK1, IRAK2, and TRAF6. Both the TNF-R1 complex and the IL-1R complex trigger activation of NIK. Activated NIK phosphorylates the IkB kinases IkB-a and IkB-b which phosphorylate IkB, leading to its degradation and, as a consequence, the activation of NF-kB.

Fas, a cell surface receptor that is a member of the TNFR family, can induce apoptosis upon binding with its ligand, FasL (CD95L). Fas interacts with FADD (MORT) via death domains present in both proteins. When bound to Fas, FADD interacts with caspase-8 (FLICE/MACH/Mch5) through death effector domains present in both proteins. The complex of Fas, FADD and caspase-8 is referred to as the death-inducing signaling complex (DISC). Recently, FLASH, a protein having a DRD as well as a CED-4-like domain, has been identified as a component of DISC that is required for caspase-8 activation during Fas-mediated apoptosis (Imai et al. (1999) *Nature* 398:777–85). In the DISC, caspase-8 undergoes oligomerization-dependent autoproteolysis, leading to activation. Activated caspase-8 cleaves several effector caspases, including caspase-3, caspase-6, and caspase-7, by proteolytic cleavage. These effector caspases cleave various death substrates involved in the morphological changes and DNA fragmentation that is central to apoptosis.

Transient expression of FLASH activates caspase-8. However, a truncated form of FLASH lacking either its DRD or CED-4-like domain does not allow activation of caspase-8 or Fas-mediated apoptosis. Thus, it appears that FLASH is involved in both Fas- and TNF-induced apoptosis mediated by activated caspase-8 (Imal et al. (1999) *Nature* 398:777–85).

Bcl10 (mE10/CIPER/CLAP/c-CARMEN) is a CARD domain containing pro-apoptotic protein that induces NF-kB activation (Koseki et al. (1999) *J. Biol. Chem.* 274:9955–61; Yan et al. (1999) *J. Biol. Chem.* 274:10287–92; Thome et al. (1999) *J. Biol Chem.* 274:9962–68; Srinivasula et al. (1999) *J. Biol. Chem.* 274:17946–54)). Bcl10 activates NF-kB by acting upstream of NIK and IkB kinase (Srinivasula et al., supra). Significantly, Bcl10 is involved in t(1;14)(p22;q23) of MALT B cell lymphoma (Willis et al. (1999) *Cell* 96:35–45; Zhang et al. (1999) *Nat. Genet.* 22:63–8). Bcl10 expressed in MALT lymphoma exhibits a frameshift mutation that causes truncation of Bcl10 distal to its CARD domain. The truncated form of Bcl10 activates NF-kB, but does not induce apoptosis (Willis et al. (1999) *Cell* 96:35–45). Expression of NF-kB is associated with suppression of apoptosis and increased cell survival in certain systems. Thus, mutant Bcl10 may promote continued cell proliferation by two different mechanisms. Bcl10 mutations similar to that observed in MALT lymphoma occur in many other tumor types, suggesting that Bcl10 may be commonly involved in malignancy.

Murine FLASH is a protein involved in Fas-mediated activation of caspase-8 during apoptosis (Imani et al. (1999) *Nature* 398:777–85). Transient expression of murine FLASH activates caspase-8. It appears that the DRD domain (amino acids 1584–1751) and the CED-4-like domain (amino acids 939–1191) of murine FLASH are required for activation of caspase-8.

NF-kB and the NF-kB pathway have been implicated in mediating chronic inflammation in inflammatory diseases such as asthma, ulcerative colitis, rheumatoid arthritis (Barnes & Epstein (1997) *New England Journal of Medicine* 336:1066) and inhibiting NF-kB or NF-kB pathways may be an effective way of treating these diseases. Binding sites for the transcription factor NF-kB are present in the promoter regions of the genes of many of the proinflammatory cytokines, chemokines, enzymes, immune receptors, and adhesion molecules important in inducing acute inflammatory responses associated with critical illnesses. Because increased activation of NF-kB can lead to enhanced expression of proinflammatory mediators, NF-kB activation may be an important event in the development of, for example, multiple organ dysfunction associated with infection, blood loss, and ischemia-reperfusion injury (Abraham (2000) *Crit Care Med* 28(4 Suppl):N100–4).

NF-kB and the NF-kB pathway have also been implicated in atherosclerosis (Navab et al. (1995) *American Journal of Cardiology* 76:18C), especially in mediating fatty streak formation, and inhibiting NF-kB or NF-kB pathways may be an effective therapy for atherosclerosis. Among the genes activated by NF-kB are cIAP-1, cIAP-2, TRAF1, and TRAF2, all of which have been shown to protect cells from TNF-A induced cell death (Wang et al. (1998) *Science* 281:1680–83).

SUMMARY OF THE INVENTION

The invention features nucleic acid molecules encoding CARD-14 proteins. These proteins, like many others having a CARD domain, play roles in apoptotic and inflammatory signaling pathways. CARD-14 participates in the network of interactions that modulate caspase activity. Upon activation, CARD-14 likely binds and activates a CARD containing protein via a CARD-CARD interaction leading to a modulation of apoptotic, inflammatory, and/or stress related pathways (e.g., NF-kB activation).

CARD-14 molecules are useful as modulating agents in regulating a variety of cellular processes including cell growth and cell death. In one aspect, this invention provides isolated nucleic acid molecules encoding CARD-14 proteins or biologically active portions thereof, as well as nucleic acid fragments suitable as primers or hybridization probes for the detection of CARD-14 encoding nucleic acids.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, or abnormal activity of a caspase by administering a compound that modulates the expression of CARD-14 (at the DNA, mRNA or protein level, e.g., by altering mRNA splicing) or by altering the activity of CARD-14. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. CARD-14 and compounds that modulate the expression or activity of CARD-14 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, autoimmune disorders can be caused by an undesirably low levels of apoptosis. Accordingly, CARD-14 and modulators of CARD-14 activity or expression can be used to treat autoimmune disorders (e.g., systemic lupus erythematosis, immune-mediated glomerulonephritis, and arthritis).

Many diseases are associated with an undesirably high rate of apoptosis. CARD-14 and modulators of CARD-14 expression or activity can be used to treat or diagnose such disorders. For example, populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis. A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Proteins containing a CARD domain are thought to be involved in various inflammatory disorders. In addition, NF-kB and the NF-kB pathway have been implicated in the induction of inflammatory responses via the activation of genes encoding proinflammatory and immunoregulatory mediators. The role of CARD-14 described herein in inducing NF-kB activity suggests that CARD-14 acts as an upstream regulator of NF-kB in NF-kB-mediated inflammatory pathways. Accordingly, CARD-14 polypeptides, nucleic acids and modulators of CARD-14 expression or activity can be used to treat immune disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

In addition to the aforementioned disorders, CARD-14 polypeptides, nucleic acids, and modulators of CARD-14 expression or activity can be used to treat disorders of cell signaling and disorders of tissues in which CARD-14 is expressed.

The invention features a nucleic acid molecule which is at least 45% (or 55%, 65%, 75%, 85%, 95%, or 98%) identical to the nucleotide sequence shown in SEQ ID NO:1; SEQ ID NO:3, complement thereof.

The invention features a nucleic acid molecule which includes a fragment of at least 150 (300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, or 3900) nucleotides of the nucleotide sequence shown in SEQ ID NO:1; SEQ ID NO:3, or a complement thereof.

In an embodiment, a CARD-14 nucleic acid molecule has the nucleotide sequence shown in SEQ ID NO:1 or SEQ ID NO:3.

Also within the invention is a nucleic acid molecule which encodes a fragment of a polypeptide having the amino acid sequence of SEQ ID NO:2.

The invention includes a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 or SEQ ID NO:3.

In general, an allelic variant of a gene will be readily identifiable as mapping to the same chromosomal location as said gene.

The invention also includes a nucleic acid molecule encoding a naturally occurring polypeptide, wherein the nucleic acid hybridizes to a nucleic acid molecule consisting of SEQ ID NO:3 under stringent conditions (e.g., hybridization in 6× sodium chloride/sodium citrate (SSC) at about 60° C., followed by one or more washes in 0.2× SSC, 0.1% SDS at 65° C.), and wherein the nucleic acid encodes a polypeptide of 1001–1007 amino acids in length, preferably 1004 amino acids, having a molecular weight of approximately 113 kD prior to post-translational modifications. Thus, the invention encompasses a nucleic acid molecule which includes the sequence of the protein coding region of a naturally occurring mRNA (or the corresponding cDNA sequence) that is expressed in a human cell.

Also within the invention are: an isolated CARD-14 protein having an amino acid sequence that is at least about 65%, preferably 75%, 85%, 95%, or 98% identical to the amino acid sequence of SEQ ID NO:2; an isolated CARD-14 protein having an amino acid sequence that is at least about 65%, preferably 75%, 85%, 95%, or 98% identical to the CARD domain of SEQ ID NO:2 (e.g., about amino acid residues 10–116 of SEQ ID NO:2); an isolated CARD-14 protein having an amino acid sequence that is at least about 65%, preferably 75%, 85%, 95%, or 98% identical to the coiled-coil domain of SEQ ID NO:2 (e.g., about amino acid residues 126–420 of SEQ ID NO:2); an isolated CARD-14 protein having an amino acid sequence that is at least about 65%, preferably 75%, 85%, 95%, or 98% identical to the PDZ domain of SEQ ID NO:2 (e.g., about amino acid residues 568–660 of SEQ ID NO:2); an isolated CARD-14 protein having an amino acid sequence that is at least about 65%, preferably 75%, 85%, 95%, or 98% identical to the SH3 domain of SEQ ID NO:2 (e.g., about amino acid residues 676–745 of SEQ ID NO:2); and an isolated CARD-14 protein having an amino acid sequence that is at least about 65%, preferably 75%, 85%, 95%, or 98% identical to the guanylate kinase (GUK) domain of SEQ ID NO:2 (e.g., about amino acid residues 826–1004 of SEQ ID NO:2).

Also within the invention are: an isolated CARD-14 protein which is encoded by a nucleic acid molecule having a nucleotide sequence that is at least about 65%, preferably 75%, 85%, or 95% identical to SEQ ID NO:1 or SEQ ID NO:3; an isolated CARD-14 protein which is encoded by a nucleic acid molecule having a nucleotide sequence at least about 65% preferably 75%, 85%, or 95% identical to the CARD domain encoding portion of SEQ ID NO:1; an isolated CARD-14 protein which is encoded by a nucleic acid molecule having a nucleotide sequence at least about 65% preferably 75%, 85%, or 95% identical to the coiled-coil domain encoding portion of SEQ ID NO:1; an isolated CARD-14 protein which is encoded by a nucleic acid molecule having a nucleotide sequence at least about 65% preferably 75%, 85%, or 95% identical to the PDZ domain encoding portion of SEQ ID NO:1; an isolated CARD-14 protein which is encoded by a nucleic acid molecule having a nucleotide sequence at least about 65% preferably 75%, 85%, or 95% identical to the SH3 domain encoding portion of SEQ ID NO:1; an isolated CARD-14 protein which is encoded by a nucleic acid molecule having a nucleotide sequence at least about 65% preferably 75%, 85%, or 95% identical to the guanylate kinase (GUK) domain encoding portion of SEQ ID NO:1; and an isolated CARD-14 protein which is encoded by a nucleic acid molecule having a nucleotide sequence which hybridizes under stringent hybridization conditions to a nucleic acid molecule having the nucleotide sequence of SEQ ID NO:1.

The CARD-14 polypeptides, nucleic acids, and antibodies of the invention may be useful for mapping the location of the CARD-14 gene as well as the location of genes associated with the following diseases: neuritis with brachial predilection; tylosis with esophageal cancer; cataract, congenital, cerulean type, 1; and malignant hyperthermia susceptibility 2, all of which map to chromosome 17 in the region of the CARD-14 gene.

Another embodiment of the invention features CARD-14 nucleic acid molecules which specifically detect CARD-14 nucleic acid molecules, relative to nucleic acid molecules encoding other members of the CARD superfamily. For example, in one embodiment, a CARD-14 nucleic acid molecule hybridizes under stringent conditions to a nucleic acid molecule comprising the nucleotide sequence of SEQ ID NO:1, SEQ ID NO:3, or a complement thereof. In another embodiment, the CARD-14 nucleic acid molecule is at least 300 (350, 400, 450, 500, 550, 600, 650, 700, 800, 900, 1000, 1200, 1400,1600,1800, 2000, 2200, 2400, 2600, 2800, 3000, 3200, 3400, 3600, 3800, or 3900) nucleotides in length and hybridizes under stringent conditions to a nucleic acid molecule comprising the nucleotide sequence shown in SEQ ID NO:1, SEQ ID NO:3, or a complement thereof. In another embodiment, an isolated CARD-14 nucleic acid molecule comprises the CARD domain encoding portion of SEQ ID NO:1 or a complement thereof. In yet another embodiment, the invention provides an isolated nucleic acid molecule which is antisense to the coding strand of a CARD-14 nucleic acid.

Another aspect of the invention provides a vector, e.g., a recombinant expression vector, comprising a CARD-14 nucleic acid molecule of the invention. In another embodiment the invention provides a host cell containing such a vector. The invention also provides a method for producing CARD-14 protein by culturing, in a suitable medium, a host cell of the invention containing a recombinant expression vector such that a CARD-14 protein is produced.

Another aspect of this invention features isolated or recombinant CARD-14 proteins and polypeptides. Preferred CARD-14 proteins and polypeptides possess at least one biological activity possessed by naturally occurring human CARD-14, e.g., (1) the ability to form protein:protein interactions with proteins in the apoptotic signaling pathway; (2) the ability to form CARD-CARD interactions with proteins in the apoptotic signaling pathway, e.g., Bcl-10; (3) the ability to bind a CARD-14 ligand; and (4) the ability to bind to an intracellular target. Other activities include: (1) modulation of cellular proliferation; (2) modulation of cellular differentiation; (3) modulation of cellular death; (4) modulation of the NF-KB pathway; and (5) modulation of stress-responsive signaling pathways.

The CARD-14 proteins of the present invention, or biologically active portions thereof, can be operatively linked to a non-CARD-14 polypeptide (e.g., heterologous amino acid sequences) to form CARD-14 fusion proteins, respectively. The invention further features antibodies that specifically bind CARD-14 proteins, such as monoclonal or polyclonal antibodies. In addition, the CARD-14 proteins or biologically active portions thereof can be incorporated into pharmaceutical compositions, which optionally include pharmaceutically acceptable carriers.

In another aspect, the present invention provides a method for detecting the presence of CARD-14 activity or expression in a biological sample by contacting the biological sample with an agent capable of detecting an indicator of CARD-14 activity such that the presence of CARD-14 activity is detected in the biological sample.

In another aspect, the invention provides a method for modulating CARD-14 activity comprising contacting a cell with an agent that modulates (inhibits or stimulates) CARD-14 activity or expression such that CARD-14 activity or expression in the cell is modulated. Examples of CARD-14 activity include the ability of CARD-14 to bind to Bcl-10, stimulate the phosphorylation of Bcl-10, and stimulate the activation of NF-kB. In one embodiment, the agent is an antibody that specifically binds to CARD-14 protein. In another embodiment, the agent modulates (increases or decreases) expression of CARD-14 by modulating transcription of a CARD-14 gene, splicing of a CARD-14 mRNA, or translation of a CARD-14 mRNA. In yet another embodiment, the agent is a nucleic acid molecule having a nucleotide sequence that is antisense to the coding strand of the CARD-14 mRNA or the CARD-14 gene.

In one embodiment, the methods of the present invention are used to treat a subject having a disorder characterized by aberrant CARD-14 protein or nucleic acid expression or activity or related to CARD-14 expression or activity by administering an agent which is a CARD-14 modulator to the subject. In one embodiment, the CARD-14 modulator is a CARD-14 protein. In another embodiment the CARD-14 modulator is a CARD-14 nucleic acid molecule. In other embodiments, the CARD-14 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-14 protein; (ii) mis-regulation of a gene encoding a CARD-14 protein; (iii) aberrant RNA splicing; and (iv) aberrant post-translational modification of a CARD-14 protein, wherein a wild-type form of the gene encodes a protein with a CARD-14 activity.

In another aspect, the invention provides a method for identifying a compound that binds to or modulates the activity of a CARD-14 protein. In general, such methods entail measuring a biological activity of a CARD-14 protein in the presence and absence of a test compound and identifying those compounds which alter the activity of the CARD-14 protein.

In another aspect, the invention provides a method for identifying a compound that modulates (increases or decreases) the ability of CARD-14 to bind to Bcl-10. In general, the method entails measuring the ability of CARD-14 to bind to Bcl-10 in the presence and absence of a test compound or test compounds, and identifying the compound or compounds that modulate the ability of CARD-14 to bind to Bcl-10.

In another aspect, the invention provides a method for identifying a compound that modulates (increases or decreases) the ability of CARD-14 to stimulate the phosphorylation of Bcl-10. In general, the method entails measuring the ability of CARD-14 to stimulate the phosphorylation of Bcl-10 in the presence and absence of a test compound or test compounds, and identifying the compound or compounds that modulate the ability of CARD-14 to stimulate the phosphorylation of Bcl-10.

In another aspect, the invention provides a method for identifying a compound that modulates (increases or decreases) the ability of CARD-14 stimulate the activation of NF-kB. In general, the method entails measuring the ability of CARD-14 stimulate the activation of NF-kB in the presence and absence of a test compound or test compounds, and identifying the compound or compounds that modulate the ability of CARD-14 stimulate the activation of NF-kB.

The invention also features methods for identifying a compound which modulates the expression of CARD-14 by measuring the expression of CARD-14 in the presence and absence of a compound.

The invention also features methods for treating disorders associated with inappropriate apoptosis by modulating the expression or activity of CARD-14.

Other features and advantages of the invention will be apparent from the following detailed description and claims.

BRIEF DESCRIPTION OF THE DRAWINGS

FIGS. 1A–1E depict the cDNA sequence (SEQ ID NO:1) and the predicted amino acid sequence (SEQ ID NO:2) of human CARD-14. The open reading frame of CARD-14 extends from nucleotide 207 to nucleotide 3218 of SEQ ID NO:1 (SEQ ID NO:3).

FIGS. 2A–2C depict a predicted nucleotide sequence (SEQ ID NO:4) and the predicted amino acid sequence (SEQ ID NO:5) of human CARD-14, based upon a CARD-14 sequence derived from a genomic clone.

FIG. 5A depicts an alignment of amino acids 16–107 of human CARD-14 (amino acid residues 16–107 of SEQ ID NO:2) with a CARD domain (SEQ ID NO:6) derived from a hidden Markov model.

FIG. 5B depicts an alignment of amino acids 568–659 of human CARD-14 (amino acid residues 568–659 of SEQ ID NO:2) with a PDZ domain (SEQ ID NO:7) derived from a hidden Markov model.

FIG. 5C depicts an alignment of amino acids 679–744 of human CARD-14 (amino acid residues 679–744 of SEQ ID NO:2) with an SH3 domain (SEQ ID NO:8) derived from a hidden Markov model.

FIG. 5D depicts an alignment of amino acids 856–948 of human CARD-14 (amino acid residues 856–948 of SEQ ID NO:2) with a guanylate kinase (GUK) domain (SEQ ID NO:9) derived from a hidden Markov model.

FIG. 5E depicts an alignment of amino acids 239–325 of human CARD-14 (amino acid residues 239–325 of SEQ ID NO:2) with a K-box region (SEQ ID NO:10) derived from a hidden Markov model.

DETAILED DESCRIPTION OF THE INVENTION

Figure 3:
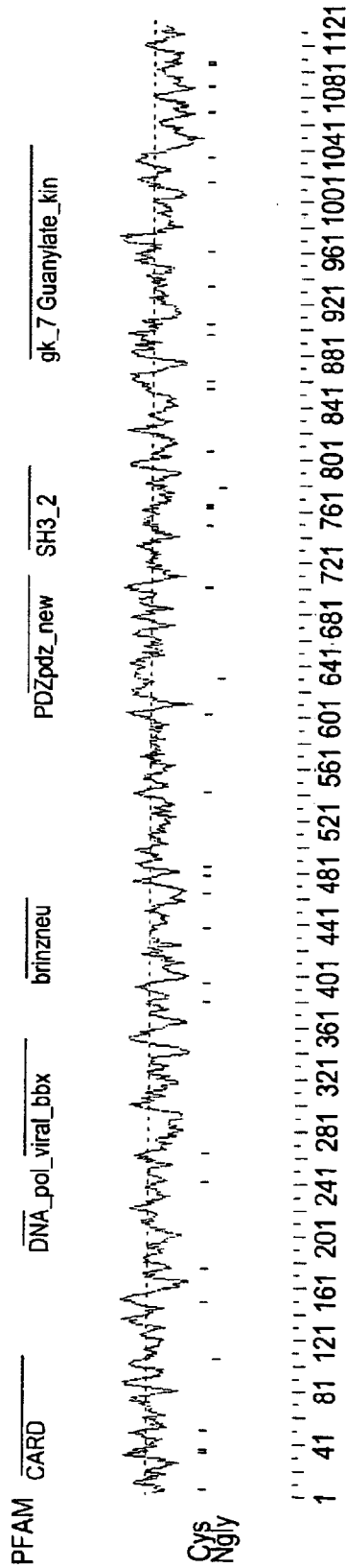
FIG. 3 depicts a hydropathy plot of CARD-14 (SEQ ID NO:2). Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The present invention is based, in part, on the identification of a cDNA sequence encoding a human CARD-14 protein. A nucleotide sequence encoding a human CARD-14 protein is shown in FIGS. 1A–1E (SEQ ID NO:1; SEQ ID NO:3 includes the open reading frame only). A predicted amino acid sequence of CARD-14 protein is also shown in FIGS. 1A–1E (SEQ ID NO:2).

Identification and Characterization of Human CARD-14

A DNA encoding human CARD-14 was identified by a search of the publicly available High Throughput Genome sequencing (HTG) nucleotide database (for information on the HTG database, see http://www.ncbi.nlm.nih.gov/HTGS/index.html; not incorporated by reference) using the CARD domain of CARD-9 (amino acids 7–98; U.S. application Ser. No. 60/168,780, filed Dec. 3, 1999). Two exons encoding contiguous portions of a novel CARD having similarity to the CARD of CARD-9 were identified in a 189,377 nucleotide BAC clone (GenBank™ Accession Number AC015559) derived from chromosome 17. GENSCAN analysis was performed to identify potential adjacent exons. Based on an analysis of the GENSCAN results, 21 exons were assembled to generate a predicted open reading frame encoding a CARD-containing protein identified as CARD-14.

FIGS. 2A–2C depict a nucleotide sequence (SEQ ID NO:4) assembled from the BAC clone which includes a predicted open reading frame encoding a 1139 amino acid protein (SEQ ID NO:5).

A predicted exon and intron structure of the genomic sequence of CARD-14 is described in Tables 1 and 2. Table 1 lists the positions of predicted CARD-14 exons in the BAC clone (GenBank™ Accession Number AC015559; hereby incorporated by reference). Table 1 also details the positions in SEQ ID NO:4 (predicted open reading frame) and the encoded portions of SEQ ID NO:5 (predicted amino acid sequence) that correspond to the individual exons. Amino acids encoded by codons that are divided between two exons are shown as being encoded by both of the exons (see amino acid sequence of SEQ ID NO:5).

TABLE 1

Predicted Exons of the CARD-14 Gene

| Exon Designation | Position in Accession Number AC015559 | Position in SEQ ID NO: 4 | Encoded Portion of SEQ ID NO:5 |
|---|---|---|---|
| 1 | 161938–162148 | 1–211 | 1–71 |
| 2 | 163152–163335 | 212–415 | 71–139 |
| 3 | 164412–164737 | 416–741 | 139–247 |
| 4 | 168876–169043 | 742–909 | 248–303 |
| 5 | 170252–170371 | 910–1029 | 304–343 |
| 6 | 171219–171398 | 1030–1209 | 344–403 |
| 7 | 171822–171971 | 1210–1359 | 404–453 |
| 8 | 173002–173118 | 1360–1476 | 454–492 |
| 9 | 175688–175830 | 1477–1619 | 493–540 |
| 10 | 176055–176149 | 1620–1714 | 540–572 |
| 11 | 178596–178659 | 1715–1778 | 572–593 |
| 12 | 178866–179088 | 1779–2001 | 593–667 |
| 13 | 180954–181080 | 2002–2128 | 668–710 |
| 14 | 181390–181630 | 2129–2369 | 710–790 |
| 15 | 183032–183095 | 2370–2433 | 790–811 |
| 16 | 183437–183551 | 2434–2548 | 812–850 |
| 17 | 184246–184416 | 2549–2719 | 850–907 |
| 18 | 184742–184863 | 2720–2841 | 907–947 |
| 19 | 186181–186296 | 2842–2957 | 948–986 |
| 20 | 187349–187529 | 2958–3138 | 986–1046 |
| 21 | 188726–189004 | 3139–3417 | 1047–1139 |

Table 2 lists predicted intron positions in the CARD-14 gene (bold residues in Table 2 indicate RNA splicing junctions). The consensus splicing sequences of both the donor and acceptor splice site each comprise sequences that are located in both an intron and an exon. Mutations in the noncoding, intronic sequence of CARD-14 may result in alterations in CARD-14 expression. For example, a mutation that causes either the destruction of a splicing site described in Table 2 or the creation of an aberrant splicing site at a position in a CARD-14 intron (e.g., at a site not used for splicing in the wild type gene) may cause improper splicing of the gene product. This could ultimately result in the translation of a mutant CARD-14 protein that may have an altered activity with respect to the wild type protein product. A mutation in an intron may thus be disease-causing by resulting in the expression of a CARD-14 molecule that either acquires or loses one or more activities possessed by the wild type CARD-14.

TABLE 2

Predicted Introns of the CARD-14 gene

| Intron designation | Position in Accession Number AC015559 | Donor Site Sequence | Acceptor Site Sequence |
|---|---|---|---|
| i | 162149–163151 | GTGA | CAAG |
| ii | 163356–164411 | GTGC | ACAG |
| iii | 164738–168875 | GTAG | ACAG |
| iv | 169044–170251 | GTAG | CCAG |
| v | 170372–171218 | GTGC | TAAG |
| vi | 171399–171821 | GTAC | ACAG |
| vii | 171972–173001 | GTGA | GCAG |
| viii | 173119–175687 | GTAC | CCAG |
| ix | 175831–176054 | GTAG | GCAG |
| x | 176150–178595 | GTGA | CCAG |
| xi | 178660–178865 | GTAA | GCAG |
| xii | 179089–180953 | GTGA | TCAG |
| xiii | 181081–181389 | GTAC | TCAG |
| xiv | 181631–183031 | GTGA | GCAG |

TABLE 2-continued

Predicted Introns of the CARD-14 gene

| Intron designation | Position in Accession Number AC015559 | Donor Site Sequence | Acceptor Site Sequence |
|---|---|---|---|
| xv | 183096–183436 | GTGA | TTAG |
| xvi | 183552–184245 | GTGA | ACAG |
| xvii | 184417–184741 | GTAT | GTAG |
| xviii | 184864–186180 | GTGA | AAAG |
| xix | 186297–187348 | GTAG | GCAG |
| xx | 187530–188725 | GTGT | CCAG |

The map position of the CARD-14 gene was determined by performing a BLAST search using BAC clone Gen-Bank™ Accession Number AC015559 against the MAPEST database. This search identified a clone (TIGR-A005039) located on human chromosome 17 near D17S784, with which a portion of the BAC clone shares 93% identity over a stretch of 397 nucleotides.

Several diseases or inherited traits map to the same region of chromosome 17 as the CARD-14 gene, suggesting a potential role for CARD-14 in a disease pathology. These diseases include: neuritis with brachial predilection ("NABP" maps to 17q25 and is characterized by recurrent attacks of pain, weakness, and sometimes muscle wasting in the arms and hands; OMIM No. 162100); tylosis with esophageal cancer ("TOC" maps to 17q24 and the tylosis is characterized by hyperkeratosis on the palms and soles and later life onset of esophageal cancer; OMIM No. 148500); cataract, congenital, cerulean type, 1 ("CCA1" maps to 17q24 and is characterized by peripheral bluish and white opacifications organized in concentric layers with occasional central lesions arranged radially; OMIM No. 115660); and malignant hyperthermia susceptibility 2 ("MHS2" maps to 17q11.2-q24; OMIM No. 154275). The OMIM (Online Mendelian Inheritance in Man) database is a catalog of human genes and genetic disorders developed for the World Wide Web by the National Center for Biotechnology Information. The database can be found at http://www.ncbi.nlm.nih./gov/omim/ and contains textual information, pictures, and reference information. The entire content of the OMIM reference numbers cited above are incorporated by reference.

Identification of a CARD-14 cDNA

The CARD-14 sequence assembled from the BAC clone was used to further characterize the CARD-14 cDNA sequence. A search of the Incyte (Palo Alto, Calif.) Life Gold Templates cDNA database was performed using the CARD-14 sequence represented in SEQ ID NO:4. This search identified a cDNA fragment (clone number 130727) that corresponds to the 5' UTR portion of the CARD-14 cDNA. Clone number 130727 was obtained and sequenced in its entirety. The sequence of this clone contains the cDNA sequence of CARD-14 as represented in SEQ ID NO:1.

The CARD-14 cDNA sequence (SEQ ID NO:1) differs somewhat from the sequence predicted by the assembly of the predicted CARD-14 exons of the BAC clone (SEQ ID NO:4). Where the CARD-14 sequences depicted in SEQ ID NO:1 and SEQ ID NO:4 differ, SEQ ID NO:1 corresponds to the CARD-14 cDNA sequence.

FIGS. 1A–1E depict the sequence of a 3931 nucleotide cDNA (SEQ ID NO:1) which includes a predicted open reading frame (SEQ ID NO:3; nucleotides 207–3218 of SEQ ID NO:1) encoding a 1004 amino acid human CARD-14 protein (SEQ ID NO:2). Human CARD-14 is predicted to be an intracellular protein.

The predicted amino acid sequence of human CARD-14 was compared to amino acid sequences of known proteins and various motifs were identified. The 1004 amino acid CARD-14 protein includes three N-glycosylation sites (e.g., about amino acid residues 114–117, 589–592, and 737–740 of SEQ ID NO:2); two cAMP- and cGMP-dependent protein kinase phosphorylation sites (e.g., about amino acid residues 6–9 and 760–763 of SEQ ID NO:2); 16 protein kinase C phosphorylation sites (e.g., about amino acid residues 25–27, 60–62, 91–93, 121–123, 250–252, 307–309, 366–368, 384–386, 463–465, 470–472, 653–655, 725–727, 759–761, 842–844, 868–870, and 1002–1004 of SEQ ID NO:2); 27 casein kinase II phosphorylation sites (e.g., about amino acid residues 12–15, 18–21, 134–137, 165–168, 221–224, 240–243, 253–256, 259–262, 280–283, 290–293, 297–300, 307–310, 366–369, 378–381, 449–452, 463–466, 501–504, 602–605, 634–637, 674–677, 725–728, 796–799, 860–863, 893–896, 926–929, 944–947, and 976–979 of SEQ ID NO:2); two tyrosine kinase phosphorylation sites (e.g., about amino acid residues 220–227 and 359–365 of SEQ ID NO:2); nine N-myristoylation sites (e.g., about amino acid residues 117–122, 130–135, 161–166, 511–516, 587–592, 714–719, 733–738, 800–805, and 980–985 of SEQ ID NO:2); an RGD cell attachment sequence (e.g., about amino acid residues 870–872 of SEQ ID NO:2); a leucine zipper pattern (e.g., about amino acid residues 385–406 of SEQ ID NO:2); and two peroxisomal targeting signals (e.g., about amino acid residues 785–793 and 941–949 of SEQ ID NO:2).

FIG. 3 depicts a hydropathy plot of CARD-14. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

Figure 4:
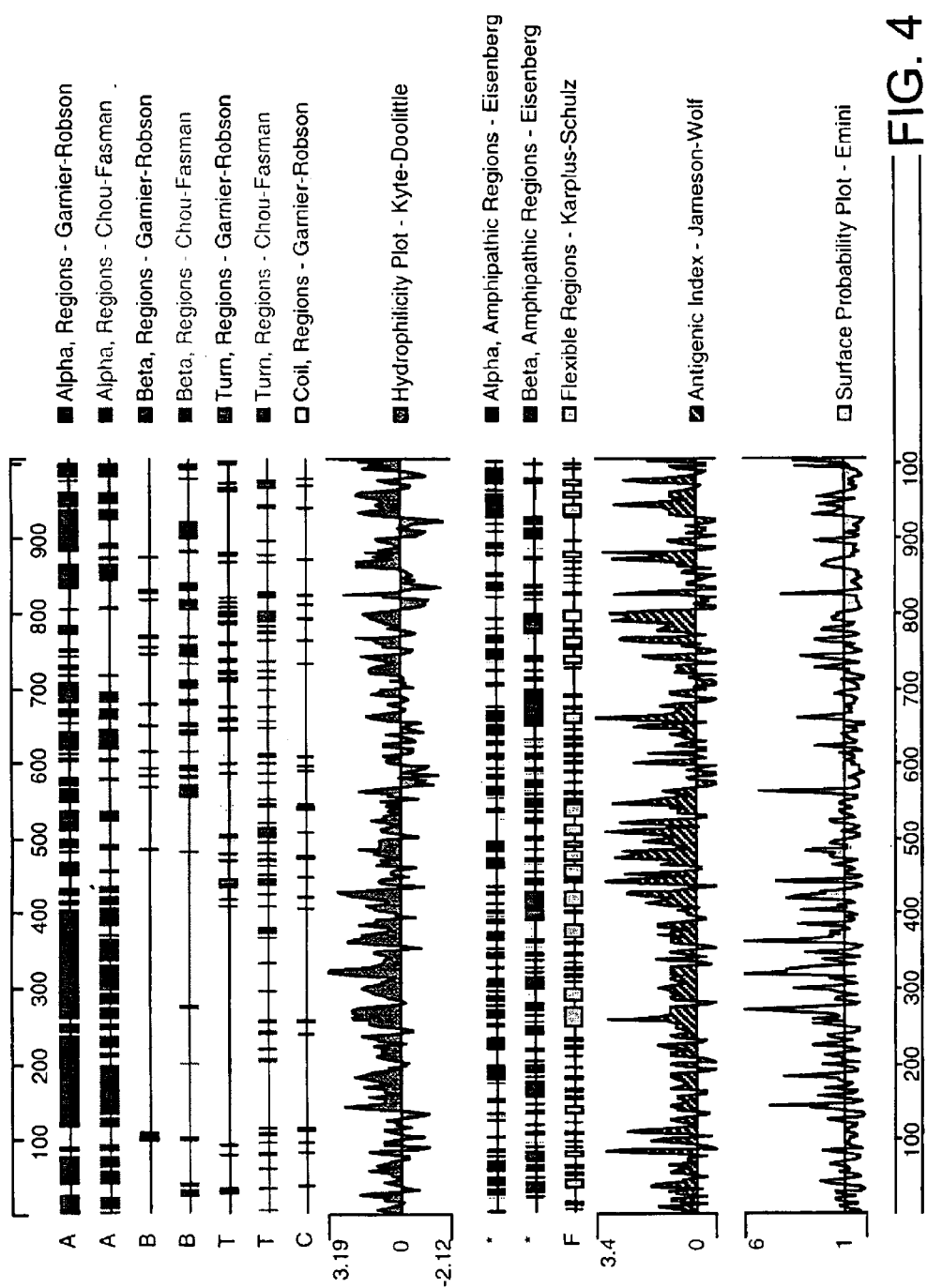
FIG. 4 depicts a plot showing the predicted structural features of CARD-14 (SEQ ID NO:2). This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of CARD-14 is presented in FIG. 4. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted CARD-14 amino acid sequence showed it to contain several potential functional domains: a CARD domain (e.g., about amino acid residues 10–116 of SEQ ID NO:2); a coiled-coil domain (e.g., about amino acid residues 126–420 of SEQ ID NO:2); a PDZ domain (e.g., about amino acid residues 568–660 of SEQ ID NO:2); an SH3 domain (e.g., about amino acid residues 676–745 of SEQ ID NO:2); and a guanylate kinase (GUK) domain (e.g., about amino acid residues 826–1004 of SEQ ID NO:2). These domains were identified by homology searching using consensus domains derived from hidden Markov models (HMMs). HMMs can be used to do multiple sequence alignment and very sensitive database searching, using statistical descriptions of a sequence family's consensus. For more information on HMM searches, see, e.g., http://hmmer.wustl.edu/ (not incorporated by reference).

FIG. 5A depicts an alignment of amino acids 16–107 of human CARD-14 (amino acid residues 16–107 of SEQ ID NO:2) with a CARD domain (SEQ ID NO:6) derived from a HMM.

FIG. 5B depicts an alignment of amino acids 568–659 of human CARD-14 (amino acid residues 568–659 of SEQ ID NO:2) with a consensus PDZ domain (SEQ ID NO:7) derived from a HMM.

FIG. 5C depicts an alignment of amino acids 679–744 of human CARD-14 (amino acid residues 679–744 of SEQ ID NO:2) with a consensus SH3 domain (SEQ ID NO:8) derived from a HMM.

FIG. 5D depicts an alignment of amino acids 856–948 of human CARD-14 (amino acid residues 856–948 of SEQ ID NO:2) with a consensus guanylate kinase (GUK) domain (SEQ ID NO:9) derived from a HMM.

FIG. 5E depicts an alignment of amino acids 239–325 of human CARD-14 (amino acid residues 239–325 of SEQ ID NO:2) with a consensus K-box region (SEQ ID NO:10) derived from a HMM.

In the alignments of FIGS. 5A–5E a single letter amino acid designation at a position on the line between the CARD-14 sequence and the HMM-generated consensus domain sequence indicates an exact match between the two. A "+" in this middle line indicates a conservative substitution at the particular residue of CARD-14. Amino acid residues located in the domains identified by the HMM search may be important for the appropriate functioning of the CARD-14 protein. For this reason, amino acid substitutions with respect to the sequence of SEQ ID NO:2 that are outside of the domains homologous to HMM consensus domains may be less detrimental to the activity of the CARD-14 protein.

CARD-14 Tissue Distribution

Expression of CARD-14 in various human tissues was evaluated using a human multiple tissue expression (MTE™) array obtained from Clontech Laboratories (Palo Alto, Calif.). The MTE™ array contains polyA RNA from 76 human tissues arrayed on one nylon membrane. The CARD domain encoding portion of the CARD-14 cDNA was used to screen the MTE™ array. Hybridization was performed under high stringency hybridization conditions.

High level expression of CARD-14 was detected in the esophagus and the placenta. Moderate expression of CARD-14 was detected in the following tissues: trachea; testes; prostate; mammary gland; salivary gland; fetal thymus; fetal spleen; substantia nigra; and spinal chord.

In addition to the array screen described above, high level CARD-14 expression was also detected by Northern analysis in the placenta and in the HeLa S3 cancer cell line. Little or no CARD-14 expression was detected in several primary cell types (brain, heart, muscle, colon, thymus, spleen, kidney, liver, intestine, lung, and peripheral blood lymphocytes) and several cell lines (HL-60, K-562, Molt-4, Raji, SW480, A549, and G431). The molecular weight of the CARD-14 transcript detected by the Northern analysis was approximately 4.4 kilobases.

Identification of an Interaction Between CARD-14 and Bcl-10

To identify the binding partners of CARD-14, a mammalian two-hybrid analysis was performed using the CARD domains of 15 known proteins. For mammalian two-hybrid assays, 293T cells in 6-well plates (35-mm wells) were transfected with the following plasmids: 750 ng of pCMV-CARD-14/AD, 750 ng of pCMV-BD fused to individual CARD domains, 250 ng of pFR-Luc firefly reporter (Stratagene), and 250 ng of pRL-TK renilla reporter (Promega). pCMV-CARD-14/AD plasmid encodes amino acids 1–118 of CARD-14. pCMV-CARD/BD plasmids were constructed by inserting individual CARD domains into pCMV-BD (Stratagene): Bcl-10 (residues 1–104), ARC (residues 1–110), RICK (residues 417–540), CARD-4 (residues 1–119), ASC (residues 92–195), caspase-1

(residues 1–110), caspase-2 (residues 1–122), caspase-4 (residues 1–108caspase-9 (residues 1–111), murine caspase-111 (residues 1–122), murine caspase-12 (residues 1–121), IAP-1 (residues 423–543), IAP-2 (residues 450–557), Apaf-1 (residues 1–108), and RAIDD (residues 1–108). Cells were harvested 24 hours after transfection and firefly luciferase activity was determined using the Dual-Luciferase Reporter Assay System (Promega). In addition, renilla luciferase activity was determined and used to normalize transfection efficiencies.

Figure 6:
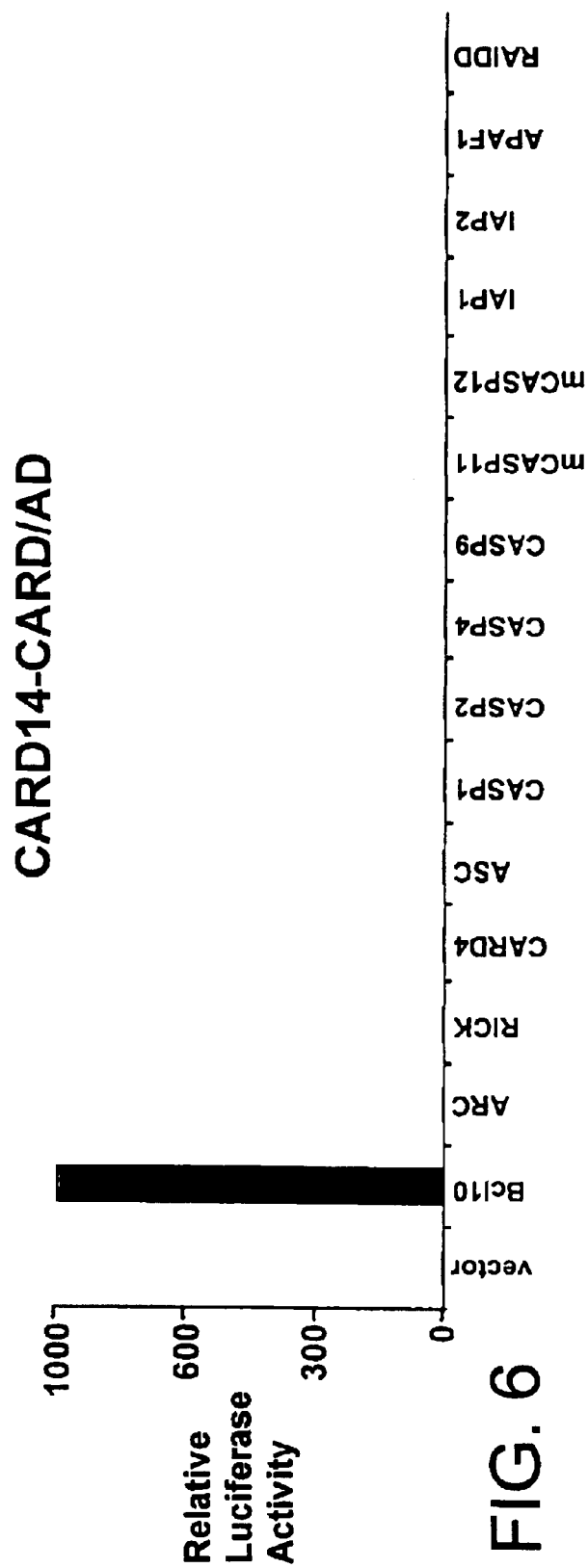
FIG. 6 depicts the interaction of the CARD domain of CARD-14 with the CARD domain of Bcl-10 in a mammalian two-hybrid assay.

The CARD of CARD-14 interacted with the CARD of Bcl10 resulting in a 999-fold increase in relative luciferase activity (FIG. 6). Co-expression of CARD-14-CARD with other CARD domains failed to activate luciferase expression, indicating that the CARD of CARD-14 interacts selectively with the CARD of Bcl-10 compared to other CARD domains tested. These data suggest that CARD-14 is a signaling partner of Bcl-10.

Figure 7:
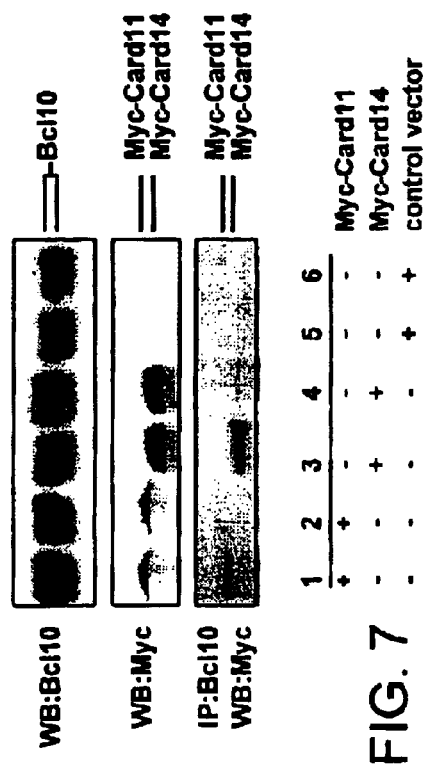
FIG. 7 depicts the results of experiments demonstrating that CARD-14 interacts with Bcl-10 in mammalian cells. 293T cells were transfected with the indicated expression constructs. Cell extracts were immunoprecipitated with either Bcl-10 antibodies (lanes 1, 3, and 5) or control T7 monoclonal antibodies (lanes 2, 4, and 6) and immunoblotted (WB) with anti-Myc antibodies to detect epitope tagged CARD-14.

The interaction between CARD-14 and Bcl-10 was also examined by overexpressing CARD-14 in cells and performing co-immunoprecipitation assays. These assays were performed as follows. Plasmids expressing CARD-14 with C-terminal Myc epitopes were constructed using pCMV-Tag 5A (Stratagene Corp., La Jolla, Calif.). 293T cells transfected with the plasmids were lysed in 50 mM Tris, pH 8.0, 120 mM NaCl, 1 mM EDTA, 0.5% Nonidet P-40 buffer and incubated with a Bcl-10 monoclonal antibody. The immune complexes were precipitated with protein G-Sepharose (Amersham Pharmacia Bio), washed extensively, and then subjected to SDS-polyacrylamide gel electrophoresis and immunoblotted with polyclonal anti-Myc antibodies (Santa Cruz Biotechnology, Inc.). Expression of Myc-tagged CARD-14 co-precipitated endogenous Bcl-10, confirming that CARD-14 interacts with Bcl-10 (FIG. 7, lane 3).

The interaction of radiolabeled CARD-14 with GST-Bcl-10 in vitro was also examined. Bcl-10 wild type and L41R mutant were expressed in DH5 alpha bacteria as GST fusion proteins and equal amounts of protein were immobilized on glutathione-sepharose (Amersham-Pharmacia). An equal amount of CARD-14 protein, labeled with $^{35}$S-methionine, was incubated with the protein bound sepharose beads in 100 μl of binding buffer (50 mM Tris-Cl pH 7.6, 120 mM NaCl, 0.5% Brij and protease inhibitors) for three hours. The beads were washed four times with the same buffer and boiled in SDS sample buffer. The proteins were then resolved on a 10% SDS gel and visualized by autoradiography. CARD-14 was found to associate directly with Bcl-10 through the N terminal CARD domain of CARD-14. Confirming the importance of the Bcl-10 CARD domain, radiolabeled CARD-14 did not associate with a variant of Bcl-10 with a point mutation (L41R) that disrupts CARD-mediated homodimerization.

To further confirm the interaction between CARD-14 and Bcl-10, co-localization experiments were performed with full-length CARD-14. In these studies, Rat-1 cells were transfected in PDL-coated glass chamber slides (BioCoat, Becton-Dickinson Labware) with plasmids expressing HA-tagged Bcl10 and Myc-tagged CARD-14 using FuGENE-6 (Roche Molecular Biochemicals) for 20 hours. Cells were fixed in 4% paraformaldehyde, permeabilized and blocked in buffer containing 0.4% Triton X-100, and sequentially incubated with primary and secondary antibodies: rabbit anti-HA polyclonal Y-11 (Santa Cruz Biotechnology), mouse anti-Myc monoclonal 9E10 (Oncogene Research Products), Alexa-488 Goat anti-mouse IgG (Molecular Probes) and Alexa-594 Goat anti-rabbit IgG (Molecular Probes). No cross-reactivity was observed between any of the antibodies. Images were acquired using a Nikon T200 microscope with a 60× oil objective and an Orca100 digital camera (Hammamatsu, Inc.) driven by MetaMorph software (Universal Imaging Corp.). Final images were prepared using Adobe PhotoShop.

When these two proteins were co-expressed in the same cell, some of the CARD-14 was found to co-localize with the Bcl-10. This finding is consistent with an intracellular interaction between CARD-14 and Bcl-10, and suggests that CARD-14 may be recruited to a cytoplasmic signaling complex with Bcl-10. To test whether the CARD domain of CARD-14 was required for this interaction, the localization of a CARD-14 truncation mutant lacking the N-terminal CARD (CARD-14/DCARD) was examined. When expressed alone, CARD-14/DCARD displayed a similar cellular localization pattern to that of full-length CARD-14. When co-expressed with Bcl-10, however, CARD-14/DCARD was not found to co-localize with Bcl-10. Deletion of the C-terminal PDZ/SH3/GUK domain resulted in co-localization with Bcl-10, indicating that the CARD and coiled-coil domains are sufficient for the interaction between CARD-14 and Bcl-10, and that this interaction requires an intact CARD domain.

Bcl-10 Phosphorylation

Figure 8:
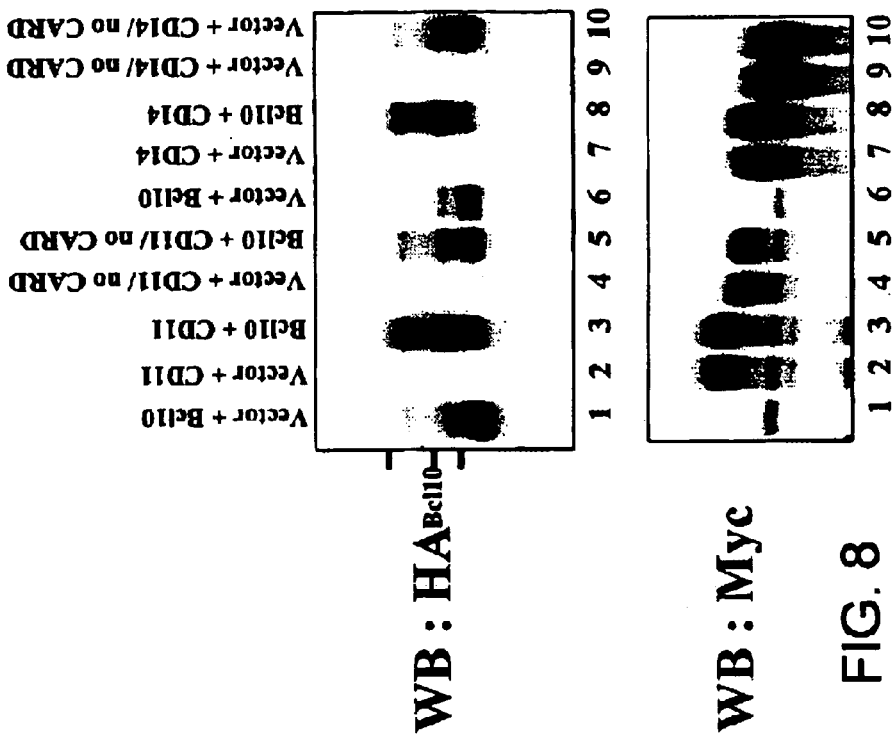
FIG. 8 depicts the results of an experiment demonstrating that CARD-14 stimulates Bcl-10 phosphorylation. 293T cells were transfected with expression constructs encoding HA-Bcl-10 and Myc-tagged CARD-14. Cell lysates were collected and immunoblotted (WB) with HA and Myc antibodies to detect Bcl-10 (upper panel) and CARD-14 (lower panel).

Bcl-10 migrates in SDS gels as a triplet ranging in size from 29 to 32 kDa due to phosphorylation of its C-terminal domain (Srinivasula et al. (1999) *J. Biol. Chem.* 274:17946; Koseki et al. (1999) *J. Biol. Chem.* 274:9955–61). Treatment of cell lysates with calf intestinal alkaline phosphatase eliminates the slower migrating forms demonstrating that the fastest migrating band represents unphosphorylated Bcl-10. Since phosphorylation can play a critical role in signal transduction, studies were performed to determine whether co-expression of CARD-14 induces the phosphorylation of Bcl-10 (FIG. 8, upper panel). When expressed alone, HA-tagged Bcl-10 is primarily unphosphorylated (FIG. 8, lane 1, lower band). However, co-expression of CARD-14 markedly increased the amount of phosphorylated $Bcl_{10}$ represented by the slower migrating bands (FIG. 8, lane 8, middle and upper bands). The induction of Bcl-10 phosphorylation is dependent on the N-terminal CARD of CARD-14 since co-expression of a truncated mutants lacking this domain has no effect on Bcl-10 phosphorylation levels (FIG. 8, lane 10). Immunoblot analysis revealed that the Myc-tagged truncation mutants were expressed at levels similar to wild type protein, suggesting that loss of function is not due to reduced levels of expression (FIG. 8, lower panel). Taken together, these data suggest that CARD-14 induces phosphorylation of Bcl-10 via its N-terminal CARD domain.

CARD-14 is a specific regulator of Bcl-10 function. The finding that CARD-14 binds to Bcl-10 through a CARD/CARD interaction suggests that this molecule functions as upstream activator of Bcl-10. Thus, CARD-14 is a member of a class of CARD proteins that may function to transduce upstream stimuli to the activation of Bcl-10 and NF-kB. In response to upstream signals, the coiled-coil domains could mediate self-association of CARD-14, resulting in the aggregation and activation of Bcl-10. Bcl-10 might then engage and oligomerize IKKg resulting in the activation of the IKK complex and NF-kB (Inohara et al. 1999 *J. Biol. Chem.* 274:14566; Poyet et al., 1999). Thus, CARD-14 could function in a manner analogous to Apaf-1 and CARD-4 that function as upstream regulators to induce oligomerization and activation of their respective downstream CARD binding partners. The data showing that CARD-14 induces the phosphorylation of Bcl-10 suggests that signal transduction may involve the participation of a serine/threonine kinase. The C-terminal PDZ/SH3/GUK domains of CARD-14 may function in an analogous manner to the C-terminal LRR domain of CARD-4 and the WD-40 domain of Apaf-1 to regulate protein activation by upstream signals. PDZ/SH3/GUK domains identify MAGUK family members, a class of proteins that associate with the plasma membrane (Fanning and Anderson, 1999 Curr Opin Cell Biol 11:432–9). Interestingly, the PDZ domain found in many MAGUK proteins has been shown to interact with the intracellular domains of specific receptors. Thus, CARD-14 may function as a scaffolding protein to assemble a multi-protein complex at the intracellular domain of a receptor that signals the activation of NF-kB.

revealed that the mutant proteins were expressed at levels similar to wild type protein, indicating that loss of function was not due to reduced levels of expression. In contrast, the C-terminal PDZ, SH3 and GUK domains were not required for NF-kB signaling since deletion of these domains had no effect on the ability of CARD-14 to induce NF-kB activity. These results suggest that the CARD domain plays an important role in NF-kB activation and that the combination of the CARD domain and coiled coil domain may be sufficient to induce NF-kB activation. The PDZlSH3/GUK domain may function as a regulator of NF-kB activation by CARD-14.

TABLE 3

Summary of Human CARD-14 Sequence Information

| Source of CARD-14 Sequence | Predicted cDNA | Predicted Protein | Predicted ORF | Figure |
|---|---|---|---|---|
| cDNA sequence | SEQ ID NO:1 | SEQ ID NO:2 | SEQ ID NO:3 | FIGS. 1A–1E |
| genomic sequence | SEQ ID NO:4 | SEQ ID NO:5 | SEQ ID NO:4 | FIGS. 2A–2C |

These observations suggest that the presence of CARD-14 may lead to the activation of a kinase that phophorylates Bcl-10. Thus, agonists and antagonists of CARD-14 are expected to modulate Bcl-10 activation and regulate the NF-κB signaling pathway. CARD-14 and/or splice variants thereof may be either positive or negative regulators of Bcl-10 function. Thus, these proteins are potential targets for regulating inflammation, cancer, NF-κB signaling, and apoptosis in human disease.

NF-kB Activation by CARD-14 and CARD-14 Deletion Mutants

Figure 9A:
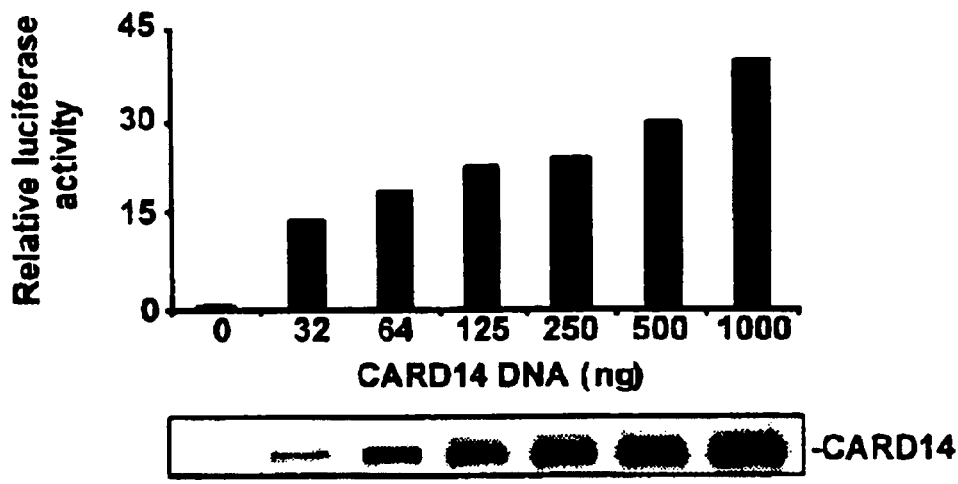
FIG. 9A depicts the results of an experiment demonstrating that CARD-14 activates NF-κB in a concentration-dependent manner.

The binding of CARD-14 to Bcl-10 described above suggests that CARD-14-Bcl-10 interactions may be part of a signaling pathway involved in apoptosis and NF-κB activation. Consistent with this signal transduction model, CARD-14 was shown to be an inducer of NF-κB activation. Expression of CARD-14 in 293T cells resulted in a 20–40 fold increase in NF-κB activity, compared to empty vector (FIG. 9A). NF-kB signaling occurred through the IKK complex since dominant-negative versions of IKK-g and IKK-b blocked the ability of CARD-14 to induce NF-kB activity.

The NF-κB activity assay was performed by co-transfecting an NF-κB reporter plasmid with a construct encoding CARD-14. In the reporter plasmid, the luciferase gene was placed under the control of the NF-κB promoter. Relative luciferase activity was determined at the end of the experiment to assess NF-κB pathway activation by CARD-14. For the NF-kB assays, 293T cells were transfected with the following plasmids: 900 ng of pNF-kB luciferase reporter (Stratagene), 100 ng of pRL-TK renilla reporter (Promega) and 1000 ng of indicated expression plasmids. Cells were harvested 24 hours after transfection, and firefly luciferase activity was determined using the Dual-Luciferase Reporter Assay System (Promega). In addition, renilla luciferase activity was determined and used to normalize transfection efficiencies.

Figure 9C:
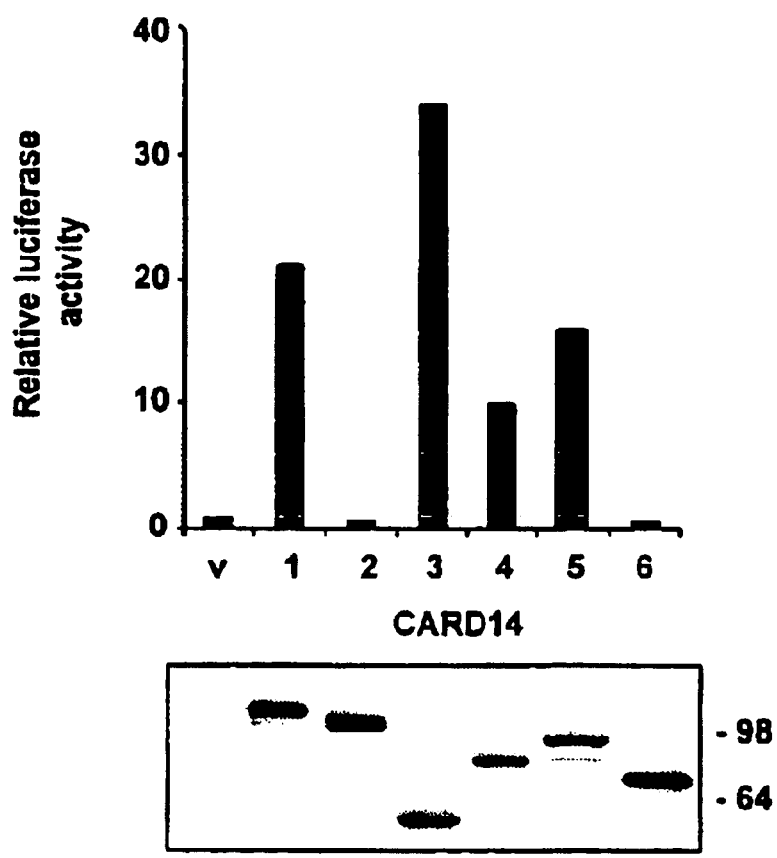
FIG. 9C depicts the induction of NF-κB activity by CARD-14 deletion mutants.
Figure 9B:
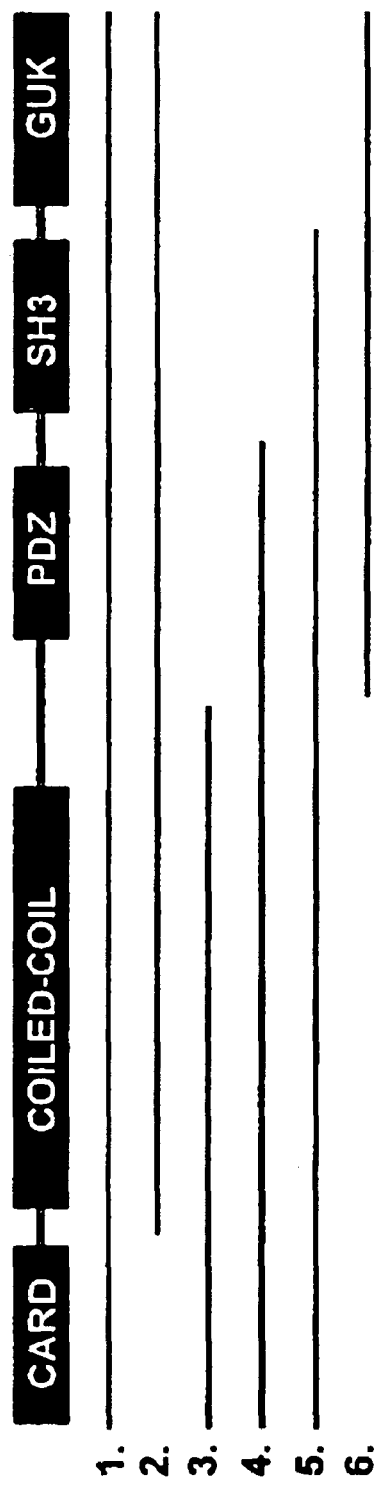
FIG. 9B is a schematic depiction of deletion mutants of CARD-14 used to map domains involved in the induction of NF-κB activity. Bars indicate domains expressed: construct 1 (CARD-14, residues 1–1004), construct 2 (CARD-14, residues 119–1004), construct 3 (CARD-14, residues 1–436), construct 4 (CARD-14, residues 1–669), construct 5 (CARD-14, residues 1–807), and construct 6 (CARD-14, residues 437–1004).

To determine the role of individual CARD-14 domains in NF-kB signaling, a series of N- and C-terminal truncation mutants of CARD-14 were constructed (FIG. 9B). The N-terminal CARD of CARD-14 was essential for NF-kB signaling since deletion of this domain eliminated the induction of NF-kB activity (FIG. 9C). Immunoblot analysis

TABLE 4

Summary of Domains of CARD-14

| Domain | Location |
|---|---|
| CARD | about amino acid residues 10–116 of SEQ ID NO:2 |
| Coiled Coil | about amino acid residues 126–420 of SEQ ID NO:2 |
| PDZ | about amino acid residues 568–660 of SEQ ID NO:2 |
| K-Box | about amino acid residues 239–325 of SEQ ID NO:2 |
| SH3 | about amino acid residues 676–745 of SEQ ID NO:2 |
| Guanylate Kinase | about amino acid residues 826–1004 of SEQ ID NO:2 |

A region, the CARD domain, of human CARD-14 protein (amino acids 10–116 of SEQ ID NO:2) bears some similarity to the CARD domains of CARD-3, CARD-4, CARD-5, CARD-6, CARD-7, CARD-8, CARD-9, CARD-10, CARD-11, CARD-12, CARD-13, and CARD-15. Detailed information concerning CARD-3, CARD-4, CARD-5, CARD-6, CARD-7, CARD-8, CARD-9, CARD-10, CARD-11, CARD-12, CARD-13, and CARD-15, can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, 60/161, 822, filed Oct. 27, 1999, U.S. application Ser. No. 60/180, 021, filed Feb. 3, 2000, U.S. application Ser. No. 09/573, 641, filed May 17, 2000, U.S. application Ser. No. 60/168, 780 filed Dec. 3, 1999, U.S. application Ser. No. 09/507,533 filed Feb. 18, 2000, U.S. application Ser. No. 09/513,904 filed Feb. 25, 2000, and U.S. application Ser. No. 09/728, 260 filed Dec. 1, 2000. The entire content of each of these applications is incorporated herein by reference.

Membrane-Associated Protein Interactions

Protein-protein interactions are required for the proper assembly of membrane-associated protein complexes and for the localization of these complexes to the appropriate membrane domain. These membrane-associated complexes can include, e.g., transmembrane receptors, ion channels, cell adhesion molecules, and cytosolic signaling elements. A class of proteins known as membrane-associated guanylate kinases (MAGUKs) play an important role in coupling the activity of transmembrane receptors to downstream signaling molecules. Members of the MAGUK protein family contain a PDZ domain, an SH3 domain, and a guanylate kinase (GUK) domain. MAGUK proteins have been found to be associated with the plasma membrane, including the discrete focal structures that comprise the highly ordered synapses. Studies of MAGUKs suggest that they function as scaffolding proteins and that the PDZ domains are used to tether transmembrane proteins in specific structural domains within the plasma membrane (Fanning and Anderson (1999) *Current Opinion in Cell Biology* 11:432).

A C-terminal region of human CARD-14 (about amino acid residues 568–1004 of SEQ ID NO:2) contains a series of domains found in members of the MAGUK protein family. All three of the domains of MAGUK family members are present in CARD-14: a PDZ domain (e.g., about amino acid residues 568–660 of SEQ ID NO:2); an SH3 domain (e.g., about amino acid residues 676–745 of SEQ ID NO:2); and a guanylate kinase (GUK) domain (e.g., about amino acid residues 826–1004 of SEQ ID NO:2).

CARD-14, like CARD-10 and CARD-11, contains both a CARD domain and a MAGUK-homology region. CARD-10 and CARD-11 are described in U.S. application Ser. No. 09/507,533 filed Feb. 18, 2000, and U.S. application Ser. No. 09/513,904 filed Feb. 25, 2000. The C-terminal MAGUK-homology region of CARD-14 (about amino acid residues 568–1004 of SEQ ID NO:2) likely functions as a site of protein-protein interaction that leads to a conformational change and/or activation of CARD-14 by upstream signaling proteins. CARD-14 is likely membrane-associated via a PDZ interaction with a receptor. CARD-14 may function to transmit apoptosis/NF-κB signals from a receptor leading to the activation of Bcl-10. The likely role of CARD-14 in apoptotic pathways makes it a therapeutic target to block apoptosis and NF-κB signaling.

CARD-14 is a member of a family of molecules (the CARD-14 family) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a CARD-14 protein includes a CARD domain having at least about 65%, preferably at least about 75%, and more preferably about 85%, 95%, or 98% amino acid sequence identity to the CARD domain of SEQ ID NO:2.

In another embodiment, a CARD-14 protein includes a coiled-coil domain having at least about 65%, preferably at least about 75%, and more preferably about 85%, 95%, or 98% amino acid sequence identity to the coiled-coil domain of SEQ ID NO:2.

In another embodiment, a CARD-14 protein includes a PDZ domain having at least about 65%, preferably at least about 75%, and more preferably about 85%, 95%, or 98% amino acid sequence identity to the PDZ domain of SEQ ID NO:2.

In another embodiment, a CARD-14 protein includes an SH3 domain having at least about 65%, preferably at least about 75%, and more preferably about 85%, 95%, or 98% amino acid sequence identity to the SH3 domain of SEQ ID NO:2.

In another embodiment, a CARD-14 protein includes a guanylate kinase (GUK) domain having at least about 65%, preferably at least about 75%, and more preferably about 85%, 95%, or 98% amino acid sequence identity to the guanylate kinase (GUK) domain of SEQ ID NO:2.

Preferred CARD-14 polypeptides of the present invention include an amino acid sequence sufficiently identical to one or more of the following domains: a CARD domain; a coiled-coil domain; a PDZ domain; a SH3 domain; or a guanylate kinase (GUK) domain.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-14 activity", "biological activity of CARD-14" or "functional activity of CARD-14", refers to an activity exerted by a CARD-14 protein, polypeptide or nucleic acid molecule on a CARD-14 responsive cell as determined in vivo, or in vitro, according to standard techniques. CARD-14 may act as a pro-apoptotic protein or an anti-apoptotic protein (i.e., it might act to decrease or increase apoptosis). A CARD-14 activity can be a direct activity, such as an association with or an enzymatic activity on a second protein or an indirect activity, such as a cellular signaling activity mediated by interaction of the CARD-14 protein with a second protein.

In one embodiment, a CARD-14 activity can include at least one or more of the following activities: (i) the ability to interact with proteins in an apoptotic signaling pathway (ii) the ability to interact with a CARD-14; (iii) the ability to interact with an intracellular target protein; (iv) the ability to interact with Bcl-10; (v) the ability to modulate phosphorylation of Bcl-10; (vi) the ability to interact, directly or indirectly, with one or more proteins having a CARD domain, e.g., a caspase, or an IAP (e.g., IAP-1 or IAP-2); (vii) the ability to modulate the activity of a caspase, e.g., caspase-9; (viii) the ability to modulate the activity of NF-kB; (ix) the ability to interact with a membrane, e.g., a plasma membrane; (x) the ability to modulate Apaf-1; (xi) the ability to interact directly or indirectly with a Bcl-2 family member; (xii) the ability to modulate the activity of a stress activated kinase (e.g., JNK/p38); (xiii) the ability to modulate phosphorylation of CHOP (GADD 153); and (xiv) the ability to interact with a heat shock protein, e.g., an interaction of the coiled-coil domain of CARD-14 with a heat shock protein. CARD-14 nucleic acid and polypeptides as well as modulators of activity of expression of CARD-14 might be used to modulate an Apaf-1 signaling pathway. CARD-14 may modulate the activity of a neurotrophin receptor and thus modulate apoptosis of neuronal cells. Accordingly, CARD-14 nucleic acids and polypeptides as well as modulators of CARD-14 activity or expression can be used to modulate apoptosis of neurons (e.g., for treatment of neurological disorders, particularly neurodegenerative disorders).

Accordingly, another embodiment of the invention features isolated CARD-14 proteins and polypeptides having a CARD-14 activity.

Various aspects of the invention are described in further detail in the following subsections.

I. Isolated Nucleic Acid Molecules

One aspect of the invention pertains to isolated nucleic acid molecules that encode CARD-14 proteins or biologically active portions thereof, as well as nucleic acid molecules sufficient for use as hybridization probes to identify CARD-14-encoding nucleic acids (e.g., CARD-14 mRNA) and fragments for use as PCR primers for the amplification or mutation of CARD-14 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated CARD-14 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1; SEQ ID NO:3, or a complement of any of these nucleotide sequences, can be isolated using standard molecular biology techniques and the sequence information provided herein. Using all or portion of the nucleic acid sequences of SEQ ID NO:1; SEQ ID NO:3, CARD-14 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-14 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, or portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-14, for example, a fragment which can be used as a probe or primer or a fragment encoding a biologically active portion of CARD-14. The nucleotide sequence determined from the cloning of the CARD-14 gene allows for the generation of probes and primers designed for use in identifying and/or cloning CARD-14 homologues in other cell types, e.g., from other tissues, as well as CARD-14 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or antisense sequence of SEQ ID NO:1, SEQ ID NO:3, or of a naturally occurring mutant of one of SEQ ID NO:1 or SEQ ID NO:3.

Probes based on the CARD-14 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-14 proteins of the present invention, identifying cells or tissue which mis-express a CARD-14 protein, such as by measuring a level of a CARD-14-encoding nucleic acid in a sample of cells from a subject, e.g., detecting CARD-14 mRNA levels or determining whether a genomic CARD-14 gene has been mutated or deleted.

A nucleic acid fragment encoding a "biologically active portion" of CARD-14 can be prepared by isolating a portion of SEQ ID NO:1 or SEQ ID NO:3, which encodes a polypeptide having a CARD-14 biological activity, expressing the encoded portion of CARD-14 protein (e.g., by recombinant expression in vitro) and assessing the activity of the encoded portion of CARD-14. For example, a nucleic acid fragment encoding a biologically active portion of CARD-14 includes a CARD domain.

The invention further encompasses nucleic acid molecules that differ from the nucleotide sequence of SEQ ID NO:1 or SEQ ID NO:3, due to degeneracy of the genetic code and thus encode the same CARD-14 protein as that encoded by the nucleotide sequence shown in SEQ ID NO:1 or SEQ ID NO:3.

In addition to the CARD-14 nucleotide sequence shown in SEQ ID NO:1; and SEQ ID NO:3, it will be appreciated by those skilled in the art that DNA sequence polymorphisms that lead to changes in the amino acid sequences of CARD-14 may exist within a population (e.g., the human population). Such genetic polymorphism in the CARD-14 gene may exist among individuals within a population due to natural allelic variation. As used herein, the terms "gene" and "recombinant gene" refer to nucleic acid molecules comprising an open reading frame encoding a CARD-14 protein, preferably a mammalian CARD-14 protein. Such natural allelic variations can typically result in 15% variance in the nucleotide sequence of the CARD-14 gene. Any and all such nucleotide variations and resulting amino acid polymorphisms in CARD-14 that are the result of natural allelic variation and that do not alter the functional activity of CARD-14 are intended to be within the scope of the invention. Thus, e.g., 1%, 2%, 3%, 4%, or 5% of the amino acids in CARD-14 (e.g., 1, 2, 3, 4, 5, 6, 8, 10, 15, 20, 25, 30, 35, 40, 45, 50, or 55 amino acids) are replaced by another amino acid, preferably by conservative substitution.

Moreover, nucleic acid molecules encoding CARD-14 proteins from other species (CARD-14 orthologs/homologues), which have a nucleotide sequence which differs from that of a CARD-14 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1200, 1400, 1600, 1800, 2000, 2200, 2400, 2600, 2800, 3000, 3200, 3400, 3600, 3800, or 3900) nucleotides in length and hybridizes under stringent conditions to the nucleic acid molecule comprising the nucleotide sequence, preferably the coding sequence, of SEQ ID NO:1, or SEQ ID NO:3.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2× SSC, 0.1% SDS at 50–65° C. (e.g., 50° C. or 60° C. or 65°) Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturallyoccurring allelic variants of the CARD-14 sequence that may exist in the population, the skilled artisan will further appreciate that changes can be introduced by mutation into the nucleotide sequence of SEQ ID NO:1, or SEQ ID NO:3, thereby leading to changes in the amino acid sequence of the encoded protein without altering the functional ability of the protein. For example, one can make nucleotide substitutions leading to amino acid substitutions at "nonessential" amino acid residues. A "nonessential" amino acid residue is a residue that can be altered from the wildtype sequence of CARD-14 protein without altering the biological activity, whereas an "essential" amino acid residue is required for bioloqical activity. For example, amino acid residues that are conserved among the CARD-14, proteins of various species are predicted to be particularly unamenable to alteration.

For example, preferred CARD-14 proteins of the present invention contain at least one CARD domain. Additionally, a CARD-14 protein also contains at least one coiled-coil domain, at least one PDZ domain, at least one SH3 domain, and at least one guanylate kinase (GUK) domain. Such conserved domains are less likely to be amenable to mutation. Other amino acid residues, however, (e.g., those that are not conserved or only semi-conserved among CARD-14 of various species) may not be essential for activity and thus are likely to be amenable to alteration.

Accordingly, another aspect of the invention pertains to nucleic acid molecules encoding CARD-14 proteins that contain changes in amino acid residues that are not essential for activity. Such CARD-14 proteins differ in amino acid sequence from SEQ ID NO:2, and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2. An isolated nucleic acid molecule encoding a CARD-14 protein having a sequence which differs from that of SEQ ID NO:1, or SEQ ID NO:3, can be created by introducing one or more nucleotide substitutions, additions or deletions into the nucleotide sequence of CARD-14 (SEQ ID NO:1, or SEQ ID NO:3) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted nonessential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and aromatic side chains (e.g., tyrosine, phenylalanine, tryptophan, histidine). Thus, a predicted nonessential amino acid residue in CARD-14 is preferably replaced with another amino acid residue from the same side chain family. Alternatively, mutations can be introduced randomly along all or part of a CARD-14 coding sequence, such as by saturation mutagenesis, and the resultant mutants can be screened for CARD-14 biological activity to identify mutants that retain activity. Following mutagenesis, the encoded protein can be expressed recombinantly and the activity of the protein can be determined.

In an embodiment, a mutant CARD-14 protein can be assayed for: (1) the ability to form protein:protein interactions with proteins in the apoptotic signaling pathway; (2) the ability to bind a CARD-14 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-14 coding strand, or to only a portion thereof, e.g., all or part of the protein coding region (or open reading frame). An antisense nucleic acid molecule can be antisense to a noncoding region of the coding strand of a nucleotide sequence encoding CARD-14. The noncoding regions ("5' and 3' untranslated regions") are the 5' and 3' sequences that flank the coding region and are not translated into amino acids. Given the coding strand sequences encoding CARD-14 disclosed herein, antisense nucleic acids of the invention can be designed according to the rules of Watson and Crick base pairing. The antisense nucleic acid molecule can be complementary to the entire coding region of CARD-14 mRNA, but more preferably is an oligonucleotide which is antisense to only a portion of the coding or noncoding region of CARD-14 mRNA. For example, the antisense oligonucleotide can be complementary to the region surrounding the translation start site of CARD-14 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-14 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-14 mRNA transcripts to thereby inhibit translation of CARD-14 mRNA. A ribozyme having specificity for a CARD-14-encoding nucleic acid can be designed based upon the nucleotide sequence of a CARD-14 cDNA disclosed herein. For example, a derivative of a Tetrahymena L-19 IVS RNA can be constructed in which the nucleotide sequence of the active site is complementary to the nucleotide sequence to be cleaved in a CARD-14-encoding mRNA. See, e.g., Cech et al. U.S. Pat. No. 4,987,071; and Cech et al. U.S. Pat. No. 5,116,742. Alternatively, CARD-14 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, CARD-14 gene expression can be inhibited by targeting nucleotide sequences complementary to the regulatory region of the CARD-14 (e.g., the CARD-14 promoter and/or enhancers) to form triple helical structures that prevent transcription of the CARD-14 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of CARD-14 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-14 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of CARD-14 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-14 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-14 Proteins and Anti-CARD-14 Antibodies.

One aspect of the invention pertains to isolated CARD-14 proteins, and biologically active portions thereof, as well as polypeptide fragments suitable for use as immunogens to raise anti-CARD-14 antibodies. In one embodiment, native CARD-14 proteins can be isolated from cells or tissue sources by an appropriate purification scheme using standard protein purification techniques. In another embodiment, CARD-14 proteins are produced by recombinant DNA techniques. Alternative to recombinant expression, a CARD-14 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-14 protein is derived, or substantially free from chemical precursors or other chemicals when chemically synthesized. The language "substantially free of cellular material" includes preparations of CARD-14 protein in which the protein is separated from cellular components of the cells from which it is isolated or recombinantly produced. Thus, CARD-14 protein that is substantially free of cellular material includes preparations of CARD-14 protein having less than about 30%, 20%, 10%, or 5% (by dry weight) of non-CARD-14 protein (also referred to herein as a "contaminating protein"). When the CARD-14 protein or biologically active portion thereof is recombinantly produced, it is also preferably substantially free of culture medium, i.e., culture medium represents less than about 20%, 10%, or 5% of the volume of the protein preparation. When CARD-14 protein is produced by chemical synthesis, it is preferably substantially free of chemical precursors or other chemicals, i.e., it is separated from chemical precursors or other chemicals which are involved in the synthesis of the protein. Accordingly such preparations of CARD-14 protein have less than about 30%, 20%, 10%, 5% (by dry weight) of chemical precursors or non-CARD-14 chemicals.

Biologically active portions of a CARD-14 protein include peptides comprising amino acid sequences sufficiently identical to or derived from the amino acid sequence of the CARD-14 protein (e.g., the amino acid sequence shown in SEQ ID NO:2), which include less amino acids than the full length CARD-14 protein, and exhibit at least one activity of a CARD-14 protein. Typically, biologically active portions comprise a domain or motif with at least one activity of the CARD-14 protein. A biologically active portion of a CARD-14 protein can be a polypeptide which is, for example, 10, 25, 50, 100, 150, 200, 250, 300 or more amino acids in length. Preferred biologically active polypeptides include one or more identified CARD-14 structural domains, e.g., the CARD domain, the coiled-coil domain, the PDZ domain, the SH3 domain, or the guanylate kinase (GUK) domain.

Moreover, other biologically active portions, in which other regions of the protein are deleted, can be prepared by recombinant techniques and evaluated for one or more of the functional activities of a native CARD-14 protein.

The CARD-14 protein has the amino acid sequence of SEQ ID NO:2. Other useful CARD-14 proteins are substantially identical to SEQ ID NO:2 and retain the functional activity of the protein of SEQ ID NO:2, yet differ in amino acid sequence due to natural allelic variation or mutagenesis.

A useful CARD-14 protein is a protein which includes an amino acid sequence at least about 45%, preferably 55%, 65%, 75%, 85%, 95%, or 99% identical to the amino acid sequence of SEQ ID NO:2, and retains the functional activity of the CARD-14 protein of SEQ ID NO:2

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity =# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-14 nucleic acid molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used.

Another preferred example of a mathematical algorithm utilized for the comparison of sequences is the Needleman and Wunsch (J. Mol. Biol. (1970) 48:444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

The invention also provides CARD-14 chimeric or fusion proteins. As used herein, a CARD-14 "chimeric protein" or "fusion protein" comprises a CARD-14 polypeptide operatively linked to a non-CARD-14 polypeptide. A "CARD-14 polypeptide" refers to a polypeptide having an amino acid sequence corresponding to all or a portion (preferably a biologically active portion) of a CARD-14, whereas a "non-CARD-14 polypeptide" refers to a polypeptide having an amino acid sequence corresponding to a protein which is not substantially identical to the CARD-14 protein, e.g., a protein which is different from the CARD-14 proteins and which is derived from the same or a different organism. Within the fusion protein, the term "operatively linked" is intended to indicate that the CARD-14 polypeptide and the non-CARD-14 polypeptide are fused in-frame to each other. The heterologous polypeptide can be fused to the N-terminus or C-terminus of the CARD-14 polypeptide.

One useful fusion protein is a GST fusion protein in which the CARD-14 sequences are fused to the C-terminus of the GST sequences. Such fusion proteins can facilitate the purification of recombinant CARD-14. In another embodiment, the fusion protein contains a signal sequence from another protein. In certain host cells (e.g., mammalian host cells), expression and/or secretion of CARD-14 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a CARD-14-immunoglobulin fusion protein in which all or part of CARD-14 is fused to sequences derived from a member of the immunoglobulin protein family. The CARD-14-immunoglobulin fusion proteins of the invention can be incorporated into pharmaceutical compositions and administered to a subject to inhibit an interaction between a CARD-14 ligand and a CARD-14 protein on the surface of a cell, to thereby suppress CARD-14-mediated signal transduction in vivo. The CARD-14-immunoglobulin fusion proteins can be used to affect the bioavailability of a CARD-14 cognate ligand. Inhibition of the CARD-14 ligand/ CARD-14 interaction may be useful therapeutically for both the treatment of proliferative and differentiative disorders, as well as modulating (e.g., promoting or inhibiting) cell survival. Moreover, the CARD-14-immunoglobulin fusion proteins of the invention can be used as immunogens to produce anti-CARD-14 antibodies in a subject, to purify CARD-14 ligands and in screening assays to identify molecules which inhibit the interaction of CARD-14 with a CARD-14 ligand.

Preferably, a CARD-14 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-14-encoding nucleic acid can be cloned into such an expression vector such that the fusion moiety is linked in-frame to the CARD-14 protein.

The present invention also pertains to variants of the CARD-14 proteins which function as either CARD-14 agonists (mimetics) or as CARD-14 antagonists. Variants of the CARD-14 proteins can be generated by mutagenesis, e.g., discrete point mutation or truncation of the CARD-14 proteins. An agonist of the CARD-14 protein can retain substantially the same, or a subset, of the biological activities of the naturally occurring form of the CARD-14 protein. An antagonist of the CARD-14 protein can inhibit one or more of the activities of the naturally occurring form of the CARD-14 protein by, for example, competitively binding to a downstream or upstream member of a cellular signaling cascade which includes the CARD-14 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-14 proteins.

Variants of the CARD-14 protein which function as either CARD-14 agonists (mimetics) or as CARD-14 antagonists can be identified by screening combinatorial libraries of mutants, e.g., truncation mutants of the CARD-14 protein for CARD-14 protein agonist or antagonist activity. In one embodiment, a variegated library of CARD-14 variants is generated by combinatorial mutagenesis at the nucleic acid level and is encoded by a variegated gene library. A variegated library of CARD-14 variants can be produced by, for example, enzymatically ligating a mixture of synthetic oligonucleotides into gene sequences such that a degenerate set of potential CARD-14 sequences is expressible as individual polypeptides, or alternatively, as a set of larger fusion proteins (e.g., for phage display) containing the set of CARD-14 sequences therein. There are a variety of methods which can be used to produce libraries of potential CARD-14 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-14 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-14, include fragments comprising or consisting of a domain or subdomain described herein, e.g., a CARD domain, a coiled-coil domain, a PDZ domain, a SH3 domain, or a guanylate kinase (GUK) domain.

In addition, libraries of fragments of the CARD-14 protein coding sequence can be used to generate a variegated population of CARD-14 fragments for screening and subsequent selection of variants of a CARD-14 protein. In one embodiment, a library of coding sequence fragments can be generated by treating a double stranded PCR fragment of a CARD-14 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-14 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-14 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-14 variants (Arkin and Yourvan (1992) Proc. Natl. Acad. Sci. USA 89:7811–7815; Delgrave et al. (1993) Protein Engineering 6(3):327–331).

An isolated CARD-14 protein, or a portion or fragment thereof, can be used as an immunogen to generate antibodies that bind CARD-14 using standard techniques for polyclonal and monoclonal antibody preparation. The full-length CARD-14 protein can be used or, alternatively, the invention provides antigenic peptide fragments of CARD-14 for use as immunogens. The antigenic peptide of CARD-14 comprises at least 8 (preferably 10, 15, 20, or 30) amino acid residues of the amino acid sequence shown in SEQ ID NO:2 and encompasses an epitope of CARD-14 such that an antibody raised against the peptide forms a specific immune complex with CARD-14.

Useful antibodies include antibodies which bind to a domain or subdomain of CARD-14 described herein (e.g., a CARD domain, a coiled-coil domain, a PDZ domain, a SH3 domain, or a guanylate kinase (GUK) domain).

Preferred epitopes encompassed by the antigenic peptide are regions of CARD-14 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIG. 4).

A CARD-14 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-14 protein or a chemically synthesized CARD-14 polypeptide. The preparation can further include an adjuvant, such as Freund's complete or incomplete adjuvant, or similar immunostimulatory agent. Immunization of a suitable subject with an immunogenic CARD-14 preparation induces a polyclonal anti-CARD-14 antibody response.

Accordingly, another aspect of the invention pertains to anti-CARD-14 antibodies. The term "antibody" as used herein refers to immunoglobulin molecules and immunologically active portions of immunoglobulin molecules, i.e., molecules that contain an antigen binding site which specifically binds an antigen, such as CARD-14. A molecule which specifically binds to CARD-14 is a molecule which binds CARD-14, but does not substantially bind other molecules in a sample, e.g., a biological sample, which naturally contains CARD-14. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-14. The term "monoclonal antibody" or "monoclonal antibody composition", as used herein, refers to a population of antibody molecules that contain only one species of an antigen binding site capable of immunoreacting with a particular epitope of CARD-14. A monoclonal antibody composition thus typically displays a single binding affinity for a particular CARD-14 protein with which it immunoreacts.

Polyclonal anti-CARD-14 antibodies can be prepared as described above by immunizing a suitable subject with a CARD-14 immunogen. The anti-CARD-14 antibody titer in the immunized subject can be monitored over time by standard techniques, such as with an enzyme linked immunosorbent assay (ELISA) using immobilized CARD-14. If desired, the antibody molecules directed against CARD-14 can be isolated from the mammal (e.g., from the blood) and further purified by well-known techniques, such as protein A chromatography to obtain the IgG fraction. At an appropriate time after immunization, e.g., when the anti-CARD-14 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-14 immunogen as described above, and the culture supernatants of the resulting hybridoma cells are screened to identify a hybridoma producing a monoclonal antibody that binds CARD-14.

Any of the many well known protocols used for fusing lymphocytes and immortalized cell lines can be applied for the purpose of generating an anti-CARD-14 monoclonal antibody (see, e.g., Current Protocols in Immunology, supra; Galfre et al. (1977) Nature 266:55052; R.H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-14, e.g., using a standard ELISA assay.

As an alternative to preparing monoclonal antibody-secreting hybridomas, a monoclonal anti-CARD-14 antibody can be identified and isolated by screening a recombinant combinatorial immunoglobulin library (e.g., an antibody phage display library) with CARD-14 to thereby isolate immunoglobulin library members that bind CARD-14. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-CARD-14 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-CARD-14 antibody (e.g., monoclonal antibody) can be used to isolate CARD-14 by standard techniques, such as affinity chromatography or immunoprecipitation. An anti-CARD-14 antibody can facilitate the purification of natural CARD-14 from cells and of recombinantly produced CARD-14 expressed in host cells. Moreover, an anti-CARD-14 antibody can be used to detect CARD-14 protein (e.g., in a cellular lysate or cell supernatant) in order to evaluate the abundance and pattern of expression of the CARD-14 protein. Anti-CARD-14 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243–56 (Alan R. Liss, Inc. 1985); Hellstrom et al., "Antibodies for Drug Delivery", in Controlled Drug Delivery (2nd Ed.), Robinson et al. (eds.), pp. 623–53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475–506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303–16 (Academic Press 1985), and Thorpe et al., "The Preparation and Cytotoxic Properties of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a CARD-14 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a CARD-14 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a CARD-14 polypeptide of the present invention wherein the composition comprises a polypeptide or polynucleotide of CARD-14. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as Word-Perfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially available software for conducting search means are and can be used in the computer-based systems of the present invention. Examples of such software includes, but is not limited to, MacPattern (EMBL), BLASTIN and BLASTX (NCBIA).

For example, software which implements the BLAST (Altschul et al. (1990) J. of Mol. Biol. 215:403–410) and BLAZE (Brutlag et al. (1993) Comp. Chem. 17:203–207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding CARD-14 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-14 proteins, mutant forms of CARD-14, fusion proteins, etc.).

The recombinant expression vectors of the invention can be designed for expression of CARD-14 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al. (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident e prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the CARD-14 expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall (1993) Yeast 9:1299–1308), pYPGE15 (Brunelli and Pall (1993) Yeast 9:1309–1318), pACTII (Dr. S. E. Elledge, Baylor College of Medicine), and picZ (InVitrogen Corp, San Diego, Calif.).

Alternatively, CARD-14 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-14 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-14 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, an isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-14 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARD-14 protein. Accordingly, the invention further provides methods for producing CARD-14 protein using the host cells of the invention. In one embodiment, the method comprises culturing the host cell of the invention (into which a recombinant expression vector or isolated nucleic acid molecule encoding CARD-14 has been introduced) in a suitable medium such that CARD-14 protein is produced. In another embodiment, the method further comprises isolating CARD-14 from the medium or the host cell.

CARD-14 nucleic acid molecules can be used in viral gene delivery systems for gene therapy, e.g., adenoviral or retroviral gene delivery systems.

CARD-14 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) Nonviral Vectors for Gene Therapy, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by bioballistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site. For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the Heios™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyethyleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) BioTechniques 28:304–315).

The host cells of the invention can also be used to produce nonhuman transgenic animals. For example, in one embodiment, a host cell of the invention is a fertilized oocyte or an embryonic stem cell into which CARD-14-coding sequences have been introduced. Such host cells can then be used to create non-human transgenic animals in which exogenous CARD-14 sequences have been introduced into their genome or homologous recombinant animals in which endogenous CARD-14 sequences have been altered. Such animals are useful for studying the function and/or activity of CARD-14 and for identifying and/or evaluating modulators of CARD-14 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-14 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-14 encoding nucleic acid into the male pronuclei of a fertilized oocyte, e.g., by microinjection, retroviral infection, and allowing the oocyte to develop in a pseudopregnant female foster animal. The CARD-14 cDNA sequence, e.g., that of SEQ ID NO:1, or SEQ ID NO:3 can be introduced as a transgene into the genome of a nonhuman animal. Alternatively, a nonhuman homolog or ortholog of the human CARD-14 gene, such as a mouse CARD-14 gene, can be isolated based on hybridization to the human CARD-14 cDNA and used as a transgene. Intronic sequences and polyadenylation signals can also be included in the transgene to increase the efficiency of expression of the transgene. A tissue-specific regulatory sequence(s) can be operably linked to the CARD-14 transgene to direct expression of CARD-14 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-14 transgene in its genome and/or expression of CARD-14 mRNA in tissues or cells of the animals. A transgenic founder animal can then be used to breed additional animals carrying the transgene. Moreover, transgenic animals carrying a transgene encoding CARD-14 can further be bred to other transgenic animals carrying other transgenes.

To create an homologous recombinant animal, a vector is prepared which contains at least a portion of a CARD-14 gene (e.g., a human or a non-human homolog of the CARD-14 gene, e.g., a murine CARD-14 gene) into which a deletion, addition or substitution has been introduced to thereby alter, e.g., functionally disrupt, the CARD-14 gene. In an embodiment, the vector is designed such that, upon homologous recombination, the endogenous CARD-14 gene is functionally disrupted (i.e., no longer encodes a functional protein; also referred to as a "knock out" vector). Alternatively, the vector can be designed such that, upon homologous recombination, the endogenous CARD-14 gene is mutated or otherwise altered but still encodes functional protein (e.g., the upstream regulatory region can be altered to thereby alter the expression of the endogenous CARD-14 protein). In the homologous recombination vector, the altered portion of the CARD-14 gene is flanked at its 5' and 3' ends by additional nucleic acid of the CARD-14 gene to allow for homologous recombination to occur between the exogenous CARD-14 gene carried by the vector and an endogenous CARD-14 gene in an embryonic stem cell. The additional flanking CARD-14 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-14 gene has homologously recombined with the endogenous CARD-14 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous CARD-14 gene within a cell line or microorganism may be modified by inserting a heterologous DNA regulatory element into the genome of a stable cell line or cloned microorganism such that the inserted regulatory element is operatively linked with the endogenous CARD-14 gene. For example, an endogenous CARD-14 which is normally "transcriptionally silent," i.e. a CARD-14 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous CARD-14 gene may be activated by insertion of a promiscuous regulatory element that works across cell types.

A heterologous regulatory element may be inserted into a stable cell line or cloned microorganism, such that it is operatively linked with an endogenous CARD-14 gene, using techniques, such as targeted homologous recombination, which are well known to those of skill in the art, and described e.g., in Chappel, U.S. Pat. No. 5,272,071; PCT publication No. WO 91/06667, published May 16, 1991.

V. Pharmaceutical Compositions

The CARD-14 nucleic acid molecules, CARD-14 proteins, and anti-CARD-14 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-14 protein or anti-CARD-14 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304–315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-14 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-14 protein (e.g., via a recombinant expression vector in a host cell in gene therapy applications), to detect CARD-14 mRNA (e.g., in a biological sample) or a genetic lesion in a CARD-14 gene, and to modulate CARD-14 activity. In addition, the CARD-14 proteins can be used to screen drugs or compounds which modulate the CARD-14 activity or expression as well as to treat disorders characterized by insufficient or excessive production of CARD-14 protein or production of CARD-14 protein forms which have decreased or aberrant activity compared to CARD-14 wild type protein. In addition, the anti-CARD-14 antibodies of the invention can be used to detect and isolate CARD-14 proteins and modulate CARD-14 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-14 proteins or biologically active portions thereof or have a stimulatory or inhibitory effect on, for example, CARD-14 expression or CARD-14 activity. Examples of a biologically active portions of human CARD-14 include: amino acids 10–116 encoding a CARD domain; amino acids 126–420 encoding a coiled-coil domain; amino acids 568–660 encoding a PDZ domain; amino acids 676–745 encoding a SH3 domain; and amino acids 826–1004 encoding a GUK domain.

Among the screening assays provided by the invention are screening to identify molecules that prevent the dimerization of CARD-14 and screening to identify molecules which block the binding of a CARD containing polypeptide, e.g., Bcl-10, to CARD-14. Screening assays, e.g., dimerization assays, can employ full-length CARD-14 or a portion of CARD-14, e.g., the CARD domain, the coiled-coil domain, the PDZ domain, the SH3 domain, or the GUK domain.

Screening assays can be used to identify molecules which modulate a CARD-14 mediated increase in transcription of genes having an AP-I or NF-κB binding site. For example, expression of a reporter gene under the control of NF-κB (or AP-1) is measured in the presence and absence of a candidate molecule and in the presence and absence of CARD-14 to identify those molecules which alter expression of the reporter in a CARD-14 dependent manner. In addition, screening assays can be used to identify molecules that modulate a CARD-14 mediated increase in CHOP phosphorylation. For example, CHOP phosphorylation is measured in the presence and absence of a candidate molecule and in the presence and absence of CARD-14. Phosphorylation of CHOP can be measured using an antibody which binds to phosphorylated CHOP, but not to non-phosphorylated CHOP.

Screening assays can also be used to identify molecules that modulate activity mediated by a domain of CARD-14. For example, enzymatic activity mediated by the guanylate kinase domain (GUK) of CARD-14 may be measured by a GTP binding assay. Test compounds or agents may be evaluated for their ability to either increase or decrease the GTP-binding ability of the GUK domain of CARD-14.

Screening assays can also be used to identify molecules that modulate a CARD-14 mediated increase in phosphorylation of Bcl-10. For example, Bcl-10 phosphorylation is measured in the presence and absence of a candidate molecule and in the presence and absence of CARD-14. Phosphorylation of Bcl-10 can be measured using an antibody that binds to phosphorylated Bcl-10, but not to non-phosphorylated Bcl-10.

In one embodiment, the invention provides assays for screening candidate or test compounds which bind to or modulate the activity of a CARD-14 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of CARD-14 or a biologically active portion thereof can be accomplished, for example, by determining the ability of the CARD-14 protein to bind to or interact with a CARD-14 target molecule. As used herein, a "target molecule" is a molecule with which a CARD-14 protein binds or interacts in nature, for example, a molecule associated with the internal surface of a cell membrane or a cytoplasmic molecule. A CARD-14 target molecule can be a non-CARD-14 molecule or a CARD-14 protein or polypeptide of the present invention. In one embodiment, a CARD-14 target molecule is a component of an apoptotic signal transduction pathway. The target, for example, can be a second intracellular protein which has catalytic activity or a protein which facilitates the association of downstream signaling molecules with CARD-14.

Determining the ability of the test compound to modulate the activity of CARD-14 or a biologically active portion thereof can be accomplished, for example, by determining the ability of the CARD-14 protein to bind to or interact with any of the specific proteins listed in the previous paragraph as CARD-14 target molecules. In another embodiment, CARD-14 target molecules include all proteins that bind to a CARD-14 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the CARD-14 protein to bind to or interact with a CARD-14 target molecule can be accomplished by one of the methods described above for determining direct binding. In an embodiment, determining the ability of the CARD-14 protein to bind to or interact with a CARD-14 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a CARD-14-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by CARD-14 expression can be identified by expressing CARD-14 in a cell line and conducting a transcriptional profiling experiment wherein the mRNA expression patterns of the cell line transformed with an empty expression vector and the cell line transformed with a CARD-14 expression vector are compared. The promoters of genes induced by CARD-14 expression can be operatively linked to reporter genes suitable for screening such as luciferase, secreted alkaline phosphatase, or beta-galactosidase and the resulting constructs could be introduced into appropriate expression vectors. A recombinant cell line containing CARD-14 and transfected with an expression vector containing a CARD-14 responsive promoter operatively linked to a reporter gene can be used to identify test compounds that modulate CARD-14 activity by assaying the expression of the reporter gene in response to contacting the recombinant cell line with test compounds. CARD-14 agonists can be identified as increasing the expression of the reporter gene and CARD-14 antagonists can be identified as decreasing the expression of the reporter gene.

In another embodiment of the invention, the ability of a test compound to modulate the activity of CARD-14, or biologically active portions thereof can be determined by assaying the ability of the test compound to modulate CARD-14-dependent pathways or processes where the CARD-14 target proteins that mediate the CARD-14 effect are known or unknown. Potential CARD-14-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-14-dependent pathways or processes could be assayed by standard cell-based or cell free assays appropriate for the specific pathway or process under study. In another embodiment, cells cotransfected with CARD-14 and a NF-kB luciferase reporter gene could be contacted with a test compound and test compounds that block CARD-14 activity could be identified by their reduction of CARD-14-dependent NF-kB pathway luciferase reporter gene expression. Test compounds that agonize CARD-14 would be expected to increase reporter gene expression. In another embodiment, CARD-14 could be expressed in a cell line and the recombinant CARD-14-expressing cell line could be contacted with a test compound. Test compounds that inhibit CARD-14 activity could be identified by their reduction of CARD-14-depended NF-kB pathway stimulation as measured by the assay of a NF-kB pathway reporter gene, NF-kB nuclear localization, IκB phosphorylation or proteolysis, or other standard assays for NF-kB pathway activation known to those skilled in the art.

In yet another embodiment, an assay of the present invention is a cell-free assay comprising contacting a CARD-14 protein or biologically active portion thereof with a test compound and determining the ability of the test compound to bind to the CARD-14 protein or biologically active portion thereof. Binding of the test compound to the CARD-14 protein can be determined either directly or indirectly as described above. In one embodiment, a competitive binding assay includes contacting the CARD-14 protein or biologically active portion thereof with a compound known to bind CARD-14 to form an assay mixture, contacting the assay mixture with a test compound, and determining the ability of the test compound to interact with a CARD-14 protein, wherein determining the ability of the test compound to interact with a CARD-14 protein comprises determining the ability of the test compound to preferentially bind to CARD-14 or biologically active portion thereof as compared to the known binding compound.

In another embodiment, an assay is a cell-free assay comprising contacting CARD-14 protein or biologically active portion thereof with a test compound and determining the ability of the test compound to modulate (e.g., stimulate or inhibit) the activity of the CARD-14 protein or biologically active portion thereof. Determining the ability of the test compound to modulate the activity of CARD-14 can be accomplished, for example, by determining the ability of the CARD-14 protein to bind to or interact with a CARD-14 target molecule, e.g., Bcl10, by one of the methods described above for determining direct binding. In an alternative embodiment, determining the ability of the test compound to modulate the activity of CARD-14 can be accomplished by determining the ability of the CARD-14 protein to further modulate a CARD-14 target molecule. For example, the catalytic/enzymatic activity of the target molecule on an appropriate substrate can be determined as previously described.

In yet another embodiment, the cell-free assay comprises contacting the CARD-14 protein or biologically active portion thereof with a known compound which binds CARD-14 to form an assay mixture, contacting the assay mixture with a test compound, and determining the ability of the test compound to interact with a CARD-14 protein, wherein determining the ability of the test compound to interact with a CARD-14 protein comprises determining the ability of the CARD-14 protein to preferentially bind to or modulate the activity of a CARD-14 target molecule. The cell-free assays of the present invention are amenable to use of either the soluble form or a membrane-associated form of CARD-14. A membrane-associated form of CARD-14 refers to CARD-14 that interacts with a membrane-bound target molecule. In the case of cell-free assays comprising the membrane-associated form of CARD-14, it may be desirable to utilize a solubilizing agent such that the membrane-associated form of CARD-14 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

A variety of methods can be used to identify compounds which inhibit an interaction between CARD-14 and a protein to which it binds, e.g. Bcl-10. Among these methods is the reverse two-hybrid screen (Huang and Schreiber (1997) Proc. Natl. Acad. Sci USA 94:13396–401; Vidal et al. and (1996) Proc. Natl. Acad. Sci. USA 93:10315–20; and Vidal et al. (1996) Proc. Natl. Acad. Sci. USA 93:10321–6). To create a high throughput assay, the reverse two hybrid screen can be combined with nanodroplet technology (Huang and Schreiber (1997) supra; and Borchardt et al. (1997) Chem. and Biol. 4:961–68). Nanodroplet technology employs 100–200 nl droplets which contain cells, defined media, and beads to which are attached test compounds. The screening can take place in the nanodroplets, and the test compounds can be attached to the beads so that their release can be controlled photochemically.

A scintillation proximity assay can be used to identify molecules which modulate the interaction between two molecules, e.g., Bcl-10 and CARD-14. In a scintillation proximity assay designed to measure the interaction between two proteins, one of the two proteins is radioactively labeled, e.g., tritiated, and the other protein is not. The two interacting proteins are incubated in the presence and absence of a test compound. The unlabeled protein is captured by a solid support material, e.g., a bead, impregnated with a fluorescer. The fraction of the radiolabeled protein that binds to the captured unlabeled protein is in close enough proximity to the solid support material to activate the fluorescer to produce light energy. The vast majority of the radiolabeled protein that does not bind to the unlabeled protein is too far from the solid support material to activate the fluorescer. Thus, the level of light energy produced by the fluorescer is indicative of the amount of radiolabeled protein bound to the unlabeled protein captured by the solid support material. Scintillation proximity assays are described in U.S. Pat. No. 4,568,649.

In more than one embodiment of the above assay methods of the present invention, it may be desirable to immobilize either CARD-14 or its target molecule to facilitate separation of complexed from uncomplexed forms of one or both of the proteins, as well as to accommodate automation of the assay. Binding of a test compound to CARD-14, or interaction of CARD-14 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CARD-14 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-14 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-14 binding or activity determined using standard techniques. In an alternative embodiment, MYC or HA epitope tag CARD-14 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-14 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-14 binding or activity determined using standard techniques.

Other techniques for immobilizing proteins on matrices can also be used in the screening assays of the invention. For example, CARD-14 or its target molecule can be immobilized utilizing conjugation of biotin and streptavidin. Biotinylated CARD-14 target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-14 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-14 or target molecule, as well as enzyme-linked assays which rely on detecting an enzymatic activity associated with the CARD-14 or a target molecule.

In another embodiment, modulators of CARD-14 expression are identified in a method in which a cell is contacted with a candidate compound and the expression of the CARD-14 promoter, mRNA or protein in the cell is determined. The level of expression of CARD-14 mRNA or protein in the presence of the candidate compound is compared to the level of expression of CARD-14 mRNA or protein in the absence of the candidate compound. The candidate compound can then be identified as a modulator of CARD-14 expression based on this comparison. For example, when expression of CARD-14 mRNA or protein is greater (statistically significantly greater) in the presence of the candidate compound than in its absence, the candidate compound is identified as a stimulator of CARD-14 mRNA or protein expression. Alternatively, when expression of CARD-14 mRNA or protein is less (statistically significantly less) in the presence of the candidate compound than in its absence, the candidate compound is identified as an inhibitor of CARD-14 mRNA or protein expression. The level of CARD-14 mRNA or protein expression in the cells can be determined by methods described herein for detecting CARD-14 mRNA or protein. The activity of the CARD-14 promoter can be assayed by linking the CARD-14 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the CARD-14 proteins can be used as "bait proteins" in a two-hybrid assay (for a discussion of a mammalian two-hybrid assay, see e.g., Hosfield and Chang (1999) *Strategies Newsletter* 2(2) :62–65) or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-14 ("CARD-14-binding proteins" or "CARD-14-bp") and modulate CARD-14 activity. Such CARD-14-binding proteins are also likely to be involved in the propagation of signals by the CARD-14 proteins as, for example, upstream or downstream elements of the CARD-14 pathway.

The two-hybrid system is based on the modular nature of most transcription factors, which consist of separable DNA-binding and activation domains. Briefly, the assay utilizes two different DNA constructs. In one construct, the gene that codes for CARD-14 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CARD-14-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-14.

In an embodiment of the invention, the ability of a test compound to modulate the activity of CARD-14, or a biologically active portion thereof can be determined by assaying the ability of the test compound to block the binding of CARD-14 to its target proteins in a yeast or mammalian two-hybrid system assay. This assay could be automated for high throughput drug screening purposes. In another embodiment of the invention, CARD-14 and a target protein could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a CARD-14 physical interaction with a target protein would result in induction of a reporter gene in contrast to the normal two-hybrid system where inhibition of CARD-14 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to CARD-14. CARD-14 interactors could be configured into two-hybrid system baits and used in two-hybrid screens to identify additional members of the CARD-14 pathway. The interactors of CARD-14 interactors identified in this way could be useful targets for therapeutic intervention in CARD-14 related diseases and pathologies and an assay of their enzymatic or binding activity could be useful for the identification of test compounds that modulate CARD-14 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-14 nucleic acid molecules described herein or fragments thereof, can be used to map the location of CARD-14 genes on a chromosome. The mapping of the CARD-14 sequences to chromosomes is an important first step in correlating these sequences with genes associated with disease.

Briefly, CARD-14 genes can be mapped to chromosomes by preparing PCR primers (preferably 15–25 bp in length) from the CARD-14 sequences. Computer analysis of CARD-14 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-14 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-14 sequences to design oligonucleotide primers, sublocalization can be achieved with panels of fragments from specific chromosomes. Other mapping strategies which can similarly be used to map a CARD-14 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-14 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A CARD-14 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of the CARD-14 polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

2. Tissue Typing

The CARD-14 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-14 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-14 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of CARD-14 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from CARD-14 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of CARD-14 are particularly appropriate for this use as greater numbers of polymorphisms occur in the noncoding regions, making it easier to differentiate individuals using this technique. Examples of polynucleotide reagents include the CARD-14 sequences or portions thereof, e.g., fragments derived from the noncoding regions of CARD-14 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-14 probes can be used to identify tissue by species and/or by organ type.

In a similar fashion, these reagents, e.g., CARD-14 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-14 protein and/or nucleic acid expression as well as CARD-14 activity, in the context of a biological sample (e.g., blood, serum, cells, tissue) to thereby determine whether an individual is afflicted with a disease or disorder, or is at risk of developing a disorder, associated with aberrant CARD-14 expression or activity. The invention also provides for prognostic (or predictive) assays for determining whether an individual is at risk of developing a disorder associated with CARD-14 protein, nucleic acid expression or activity. For example, mutations in a CARD-14 gene can be assayed in a biological sample. Such assays can be used for prognostic or predictive purpose to thereby prophylactically treat an individual prior to the onset of a disorder characterized by or associated with CARD-14 protein, nucleic acid expression or activity.

Another aspect of the invention provides methods for determining CARD-14 protein, nucleic acid expression or CARD-14 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-14 in clinical trials.

These and other agents are described in further detail in the following sections.

1. Diagnostic Assays

An exemplary method for detecting the presence or absence of CARD-14 in a biological sample involves obtaining a biological sample from a test subject and contacting the biological sample with a compound or an agent capable of detecting CARD-14 protein or nucleic acid (e.g., mRNA, genomic DNA) that encodes CARD-14 protein such that the presence of CARD-14 is detected in the biological sample. An agent for detecting CARD-14 mRNA or genomic DNA is a labeled nucleic acid probe capable of hybridizing to CARD-14 mRNA or genomic DNA. The nucleic acid probe can be, for example, a full-length CARD-14 nucleic acid, such as the nucleic acid of SEQ ID NO:1 or a portion thereof, such as an oligonucleotide of at least 15, 30, 50, 100, 250, 500, 750, 1000, 1250, 1500, 1750, 2000, 2250, 2500, 2750, 3000, 3250, 3500, 3750, or 3900 nucleotides in length and sufficient to specifically hybridize under stringent conditions to mRNA or genomic DNA. Other suitable probes for use in the diagnostic assays of the invention are described herein.

An agent for detecting CARD-14 protein can be an antibody capable of binding to CARD-14 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-14 mRNA, protein, or genomic DNA in a biological sample in vitro as well as in vivo. For example, in vitro techniques for detection of CARD-14 mRNA include Northern hybridizations and in situ hybridizations. In vitro techniques for detection of CARD-14 protein include enzyme linked immunosorbent assays (ELISAs), Western blots, immunoprecipitations and immunofluorescence. In vitro techniques for detection of CARD-14 genomic DNA include Southern hybridizations.

Furthermore, in vivo techniques for detection of CARD-14 protein include introducing into a subject a labeled anti-CARD-14 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting CARD-14 protein, mRNA, or genomic DNA, such that the presence of CARD-14 protein, mRNA or genomic DNA is detected in the biological sample, and comparing the presence of CARD-14 protein, mRNA or genomic DNA in the control sample with the presence of CARD-14 protein, mRNA or genomic DNA in the test sample.

The invention also encompasses kits for detecting the presence of CARD-14 in a biological sample (a test sample). Such kits can be used to determine if a subject is suffering from or is at increased risk of developing a disorder associated with aberrant expression of CARD-14 (e.g., an immunological disorder). For example, the kit can comprise a labeled compound or agent capable of detecting CARD-14 protein or mRNA in a biological sample and means for determining the amount of CARD-14 in the sample (e.g., an anti-CARD-14 antibody or an oligonucleotide probe which binds to DNA encoding CARD-14, e.g., SEQ ID NO:1 or SEQ ID NO:3). Kits may also include instruction for observing that the tested subject is suffering from or is at risk of developing a disorder associated with aberrant expression of CARD-14 if the amount of CARD-14 protein or mRNA is above or below a normal level.

For antibody-based kits, the kit may comprise, for example: (1) a first antibody (e.g., attached to a solid support) which binds to CARD-14 protein; and, optionally, (2) a second, different antibody which binds to CARD-14 protein or the first antibody and is conjugated to a detectable agent. For oligonucleotide-based kits, the kit may comprise, for example: (1) a oligonucleotide, e.g., a detectably labeled oligonucleotide, which hybridizes to a CARD-14 nucleic acid sequence or (2) a pair of primers useful for amplifying a CARD-14 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-14.

2. Prognostic Assays

The methods described herein can furthermore be utilized as diagnostic or prognostic assays to identify subjects having or at risk of developing a disease or disorder associated with aberrant CARD-14 expression or activity. For example, the assays described herein, such as the preceding diagnostic assays or the following assays, can be utilized to identify a subject having or at risk of developing a disorder associated with CARD-14 protein, nucleic acid expression or activity. Alternatively, the prognostic assays can be utilized to identify a subject having or at risk for developing such a disease or disorder. Thus, the present invention provides a method in which a test sample is obtained from a subject and CARD-14 protein or nucleic acid (e.g., mRNA, genomic DNA) is detected, wherein the presence of CARD-14 protein or nucleic acid is diagnostic for a subject having or at risk of developing a disease or disorder associated with aberrant CARD-14 expression or activity. As used herein, a "test sample" refers to a biological sample obtained from a subject of interest. For example, a test sample can be a biological fluid (e.g., serum), cell sample, or tissue. Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-14 expression or activity. For example, such methods can be used to determine whether a subject can be effectively treated with a specific agent or class of agents (e.g., agents of a type which decrease CARD-14 activity). Thus, the present invention provides methods for determining whether a subject can be effectively treated with an agent for a disorder associated with aberrant CARD-14 expression or activity in which a test sample is obtained and CARD-14 protein or nucleic acid is detected (e.g., wherein the presence of CARD-14 protein or nucleic acid is diagnostic for a subject that can be administered the agent to treat a disorder associated with aberrant CARD-14 expression or activity).

The methods of the invention can also be used to detect genetic lesions or mutations in a CARD-14 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-14-protein, or the mis-expression of the CARD-14 gene. For example, such genetic lesions can be detected by ascertaining the existence of at least one of 1) a deletion of one or more nucleotides from a CARD-14 gene; 2) an addition of one or more nucleotides to a CARD-14 gene; 3) a substitution of one or more nucleotides of a CARD-14 gene; 4) a chromosomal rearrangement of a CARD-14 gene; 5) an alteration in the level of a messenger RNA transcript of a CARD-14 gene; 6) aberrant modification of a CARD-14 gene, such as of the methylation pattern of the genomic DNA; 7) the presence of a non-wild type splicing pattern of a messenger RNA transcript of a CARD-14 gene (e.g., caused by a mutation in a splice donor or splice acceptor site); 8) a non-wild type level of a CARD-14-protein; 9) allelic loss of a CARD-14 gene; and 10) inappropriate post-translational modification of a CARD-14-protein. As described herein, there are a large number of assay techniques known in the art which can be used for detecting lesions in a CARD-14 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-14 gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-14 gene under conditions such that hybridization and amplification of the CARD-14-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-14 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in CARD-14 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-14 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-14 gene and detect mutations by comparing the sequence of the sample CARD-14 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-14 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type CARD-14 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-14 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-14 sequence, e.g., a wild-type CARD-14 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-14 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control CARD-14 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-14 gene.

Furthermore, any cell type or tissue, preferably peripheral blood leukocytes, in which CARD-14 is expressed may be utilized in the prognostic assays described herein.

3. Pharmacogenomics

Agents, or modulators which have a stimulatory or inhibitory effect on CARD-14 activity (e.g., CARD-14 gene expression) as identified by a screening assay described herein can be administered to individuals to treat (prophylactically or therapeutically) disorders (e.g., an immunological disorder) associated with aberrant CARD-14 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-14 protein, expression of CARD-14 nucleic acid, or mutation content of CARD-14 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytoclrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of CARD-14 protein, expression of CARD-14 nucleic acid, or mutation content of CARD-14 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-14 modulator, such as a modulator identified by one of the exemplary screening assays described herein.

4. Monitoring of Effects During Clinical Trials

Monitoring the influence of agents (e.g., drugs, compounds) on the expression or activity of CARD-14 (e.g., the ability to modulate aberrant cell proliferation and/or differentiation) can be applied not only in basic drug screening, but also in clinical trials. For example, the effectiveness of an agent determined by a screening assay as described herein to increase CARD-14 gene expression, protein levels, or upregulate CARD-14 activity, can be monitored in clinical trails of subjects exhibiting decreased CARD-14 gene expression, protein levels, or downregulated CARD-14 activity. Alternatively, the effectiveness of an agent determined by a screening assay to decrease CARD-14 gene expression, protein levels, or downregulated CARD-14 activity, can be monitored in clinical trials of subjects exhibiting increased CARD-14 gene expression, protein levels, or upregulated CARD-14 activity. In such clinical trials, the expression or activity of CARD-14 and, preferably, other genes that have been implicated in, for example, a cellular proliferation disorder can be used as a "read out" or markers of the immune responsiveness of a particular cell.

For example, and not by way of limitation, genes, including CARD-14, that are modulated in cells by treatment with an agent (e.g., compound, drug or small molecule) which modulates CARD-14 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-14 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-14 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-14 protein, mRNA, or genomic DNA in the preadministration sample; (iii) obtaining one or more post-administration samples from the subject; (iv) detecting the level of expression or activity of the CARD-14 protein, mRNA, or genomic DNA in the post-administration samples; (v) comparing the level of expression or activity of the CARD-14 protein, mRNA, or genomic DNA in the pre-administration sample with the CARD-14 protein, mRNA, or genomic DNA in the post administration sample or samples; and (vi) altering the administration of the agent to the subject accordingly. For example, increased administration of the agent may be desirable to increase the expression or activity of CARD-14 to higher levels than detected, i.e., to increase the effectiveness of the agent. Alternatively, decreased administration of the agent may be desirable to decrease expression or activity of CARD-14 to lower levels than detected, i.e., to decrease the effectiveness of the agent.

5. Transcriptional Profiling

The CARD-14 nucleic acid molecules described herein, including small oligonucleotides, can be used in transcriptionally profiling. For example, these nucleic acids can be used to examine the expression of CARD-14 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-14, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-14 expression or activity, examples of which are provided herein.

1. Prophylactic Methods

In one aspect, the invention provides a method for preventing in a subject, a disease or condition associated with an aberrant CARD-14 expression or activity, by administering to the subject an agent which modulates CARD-14 expression or at least one CARD-14 activity. Subjects at risk for a disease which is caused or contributed to by aberrant CARD-14 expression or activity can be identified by, for example, any or a combination of diagnostic or prognostic assays as described herein. Administration of a prophylactic agent can occur prior to the manifestation of symptoms characteristic of the CARD-14 aberrancy, such that a disease or disorder is prevented or, alternatively, delayed in its progression. Depending on the type of CARD-14 aberrancy, for example, a CARD-14 agonist or CARD-14 antagonist agent can be used for treating the subject. The appropriate agent can be determined based on screening assays described herein.

2. Therapeutic Methods

Another aspect of the invention pertains to methods of modulating CARD-14 expression or activity for therapeutic purposes. The modulatory method of the invention involves contacting a cell with an agent that modulates one or more of the activities of CARD-14 protein activity associated with the cell. An agent that modulates CARD-14 protein activity can be an agent as described herein, such as a nucleic acid or a protein, a naturally-occurring cognate ligand of a CARD-14 protein, a peptide, a CARD-14 peptidomimetic, or other small molecule. In one embodiment, the agent stimulates one or more of the biological activities of CARD-14 protein. Examples of such stimulatory agents include active CARD-14 protein and a nucleic acid molecule encoding CARD-14 that has been introduced into the cell. In another embodiment, the agent inhibits one or more of the biological activities of CARD-14 protein. Examples of such inhibitory agents include antisense CARD-14 nucleic acid molecules and anti-CARD-14 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a CARD-14 protein or nucleic acid molecule or a disorder related to CARD-14 expression or activity. In one embodiment, the method involves administering an agent (e.g., an agent identified by a screening assay described herein), or combination of agents that modulates (e.g., upregulates or downregulates) CARD-14 expression or activity. In another embodiment, the method involves administering a CARD-14 protein or nucleic acid molecule as therapy to compensate for reduced or aberrant CARD-14 expression or activity. Stimulation of CARD-14 activity is desirable in situations in which CARD-14 is abnormally downregulated and/or in which increased CARD-14 activity is likely to have a beneficial effect. Conversely, inhibition of CARD-14 activity is desirable in situations in which CARD-14 is abnormally upregulated, e.g., in myocardial infarction, and/or in which decreased CARD-14 activity is likely to have a beneficial effect.

The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising the amino acid sequence of SEQ ID NO:2.

2. (Original) The isolated polypeptide of claim 1, wherein the polypeptide consists of the amino acid sequence of SEQ ID NO:2.

3. An isolated polypeptide consisting of a fragment of the amino acid sequence of SEQ ID NO:2, wherein said fragment comprises amino acids 10–116 of SEQ ID NO:2.

4. An isolated polypeptide consisting of a fragment of the amino acid sequence of SEQ ID NO:2, wherein said fragment comprises amino acids 826–1004 of SEQ ID NO:2.

5. An isolated polypeptide comprising an amino acid sequence that is at least 85% identical to the sequence of SEQ ID NO:2, wherein the polypeptide binds to Bcl-10.

6. The polypeptide of claim 5, wherein the amino acid sequence is at least 95% identical to the sequence of SEQ ID NO:2.

7. The polypeptide of claim 5, wherein the amino acid sequence is at least 98% identical to the sequence of SEQ ID NO:2.

8. An isolated polypeptide comprising an amino acid sequence that is at least 85% identical to the sequence of SEQ ID NO:2, wherein the polypeptide activates NF-kB.

9. The polypeptide of claim 8, wherein the amino acid sequence is at least 95% identical to the sequence of SEQ ID NO:2.

10. The polypeptide of claim 8, wherein the amino acid sequence is at least 98% identical to the sequence of SEQ ID NO:2.

11. The polypeptide of claim 1 linked by a peptide bond to a heterologous polypeptide.

12. The polypeptide of claim 3 linked by a peptide bond to a heterologous polypeptide.

13. The polypeptide of claim 4 linked by a peptide bond to a heterologous polypeptide.

14. An isolated polypeptide comprising an amino acid sequence that is at least 85% identical to the sequence of SEQ ID NO:2, wherein the polypeptide stimulates Bcl-10 phosphorylation.

15. The polypeptide of claim 14, wherein the amino acid sequence is at least 95% identical to the sequence of SEQ ID NO:2.

16. The polypeptide of claim 14, wherein the amino acid sequence is at least 98% identical to the sequence of SEQ ID NO:2.

* * * * *